US011427563B2

(12) United States Patent
deLong et al.

(10) Patent No.: US 11,427,563 B2
(45) Date of Patent: Aug. 30, 2022

(54) ARYL CYCLOPROPYL-AMINO-ISOQUINOLINYL AMIDE COMPOUNDS

(71) Applicant: Aerie Pharmaceuticals, Inc., Bedminster, NJ (US)

(72) Inventors: Mitchell A. deLong, Chapel Hill, NC (US); Jill M. Sturdivant, Chapel Hill, NC (US); Cynthia L. Lichorowic, Raleigh, NC (US); Andriy Kornilov, Ypsilanti, MI (US)

(73) Assignee: Aerie Pharmaceuticals, Inc., Bedminster, NJ (US)

( * ) Notice: Subject to any disclaimer, the term of this patent is extended or adjusted under 35 U.S.C. 154(b) by 0 days.

(21) Appl. No.: 16/570,849

(22) Filed: Sep. 13, 2019

(65) Prior Publication Data

US 2020/0102290 A1    Apr. 2, 2020

Related U.S. Application Data

(60) Provisional application No. 62/731,609, filed on Sep. 14, 2018, provisional application No. 62/738,962, filed on Sep. 28, 2018.

(51) Int. Cl.

| *C07D 401/14* | (2006.01) |
|---|---|
| *C07D 417/12* | (2006.01) |
| *C07D 401/12* | (2006.01) |
| *A61P 27/06* | (2006.01) |
| *C07D 413/12* | (2006.01) |
| *C07D 405/12* | (2006.01) |
| *C07D 417/14* | (2006.01) |

(52) U.S. Cl.
CPC ............ *C07D 401/14* (2013.01); *A61P 27/06* (2018.01); *C07D 401/12* (2013.01); *C07D 405/12* (2013.01); *C07D 413/12* (2013.01); *C07D 417/12* (2013.01); *C07D 417/14* (2013.01)

(58) Field of Classification Search
CPC .. C07D 401/14; C07D 401/12; C07D 405/12; C07D 413/12
USPC ...................................................... 546/143
See application file for complete search history.

(56) References Cited

U.S. PATENT DOCUMENTS

| 4,146,637 A | 3/1979 | Metz et al. |
|---|---|---|
| 4,337,256 A | 6/1982 | Yasushi et al. |
| 4,456,757 A | 6/1984 | Hidaka et al. |
| 4,709,032 A | 11/1987 | Hidaka et al. |
| 4,911,928 A | 3/1990 | Wallach |
| 4,954,512 A | 9/1990 | Oguro et al. |
| 5,508,288 A | 4/1996 | Forbes et al. |
| 5,519,036 A | 5/1996 | Himmelsbach et al. |
| 5,770,759 A | 1/1998 | Ueno et al. |
| 5,798,380 A | 8/1998 | Kaufman et al. |
| 5,889,052 A | 3/1999 | Klimko et al. |
| 5,891,646 A | 4/1999 | Barak et al. |
| 5,977,173 A | 11/1999 | Wos et al. |
| 5,994,397 A | 11/1999 | Selliah et al. |
| 6,025,392 A | 2/2000 | Selliah et al. |
| 6,030,999 A | 2/2000 | Stjernschantz et al. |
| 6,037,364 A | 3/2000 | Burk |
| 6,037,368 A | 3/2000 | Selliah et al. |
| 6,048,895 A | 4/2000 | Wos et al. |
| 6,110,693 A | 8/2000 | Barak et al. |
| 6,110,912 A | 8/2000 | Kaufman et al. |
| 6,362,177 B1 | 3/2002 | Shiota et al. |
| 6,586,425 B2 | 7/2003 | Kaufman et al. |
| 6,699,891 B1 | 3/2004 | Kawaanishi et al. |
| 6,787,534 B2 | 9/2004 | Haneda |
| 7,268,143 B2 | 9/2007 | Jagtap et al. |
| 7,329,684 B2 | 2/2008 | Mjalli et al. |
| 7,345,158 B2 | 3/2008 | Egashira et al. |
| 7,361,678 B2 | 4/2008 | Mjalli et al. |
| 7,374,891 B2 | 5/2008 | Shahbaz |
| 7,378,498 B2 | 5/2008 | Worley et al. |
| 7,470,787 B2 | 12/2008 | deLong et al. |
| 7,671,205 B2 | 3/2010 | deLong et al. |
| 8,034,943 B2 | 10/2011 | deLong et al. |
| 8,129,411 B2 | 3/2012 | Ehara et al. |
| 8,278,294 B2 | 10/2012 | Plettenburg et al. |
| 8,357,699 B2 | 1/2013 | deLong et al. |
| 8,394,826 B2 | 3/2013 | deLong et al. |
| 8,450,344 B2 | 5/2013 | deLong et al. |
| 8,455,513 B2 * | 6/2013 | deLong ..................... A61P 1/04 514/307 |

(Continued)

FOREIGN PATENT DOCUMENTS

| EP | 0109023 | 5/1984 |
|---|---|---|
| EP | 0232569 | 8/1987 |

(Continued)

OTHER PUBLICATIONS

Bhatia et al. A review on Bioisosterism (Year: 2011).*

(Continued)

*Primary Examiner* — D Margaret M Seaman

(74) *Attorney, Agent, or Firm* — K&L Gates LLP; Louis C. Cullman; Benjamin D. Heuberger

(57) ABSTRACT

Provided herein are amino isoquinolinyl amide and sulfonamide compounds that affect the function of kinases and other proteins in a cell and that are useful as therapeutic agents. In particular, these compounds are useful in the treatment of eye diseases such as glaucoma and retinal diseases, as anti-inflammatory agents, for the treatment of cardiovascular diseases, and for diseases characterized by abnormal growth, such as cancers.

32 Claims, No Drawings

Specification includes a Sequence Listing.

(56) References Cited

U.S. PATENT DOCUMENTS

| | | | |
|---|---|---|---|
| 8,455,514 B2 | 6/2013 | deLong et al. | |
| 8,455,647 B2 | 6/2013 | deLong et al. | |
| 8,716,310 B2 | 5/2014 | deLong et al. | |
| 8,759,388 B2 | 7/2014 | deLong et al. | |
| 8,809,326 B2 | 8/2014 | Bosanac et al. | |
| 8,871,757 B2 | 10/2014 | deLong et al. | |
| 8,921,392 B2 | 12/2014 | deLong et al. | |
| 9,096,569 B2 | 8/2015 | deLong et al. | |
| 9,255,101 B2 | 2/2016 | Berrebi-Bertrand et al. | |
| 9,365,518 B2 * | 6/2016 | deLong | A61P 13/12 |
| 9,415,043 B2 | 8/2016 | Kopczynski | |
| 9,643,927 B1 | 5/2017 | Sturdivant et al. | |
| 9,884,840 B2 | 2/2018 | deLong et al. | |
| 10,112,920 B2 | 10/2018 | deLong et al. | |
| 10,174,017 B2 | 1/2019 | deLong et al. | |
| 10,654,844 B2 | 5/2020 | deLong et al. | |
| 10,858,339 B2 * | 12/2020 | deLong | C07D 217/24 |
| 10,882,840 B2 | 1/2021 | deLong et al. | |
| 10,899,714 B2 | 1/2021 | deLong et al. | |
| 2004/0091946 A1 | 5/2004 | Oakley et al. | |
| 2004/0157859 A1 | 8/2004 | Wu et al. | |
| 2004/0176462 A1 | 9/2004 | Kawanishi et al. | |
| 2005/0032125 A1 | 2/2005 | Oakley et al. | |
| 2005/0176712 A1 | 8/2005 | Wakabayashi et al. | |
| 2005/0245509 A1 | 11/2005 | Nakajima et al. | |
| 2005/0282805 A1 | 12/2005 | Hangeland et al. | |
| 2006/0270670 A1 | 11/2006 | Chew et al. | |
| 2007/0111983 A1 | 5/2007 | Fong | |
| 2007/0123561 A1 | 5/2007 | Lee et al. | |
| 2007/0129404 A1 | 6/2007 | Hagihara et al. | |
| 2007/0135499 A1 | 6/2007 | deLong et al. | |
| 2007/0149473 A1 | 6/2007 | Chatterton et al. | |
| 2007/0149548 A1 | 6/2007 | Hellberg et al. | |
| 2007/0167444 A1 | 7/2007 | Kuramochi et al. | |
| 2007/0238741 A1 | 10/2007 | Nagarathnam et al. | |
| 2008/0021026 A1 | 1/2008 | Kahraman et al. | |
| 2008/0021217 A1 | 1/2008 | Borchardt | |
| 2008/0058384 A1 | 3/2008 | Lee et al. | |
| 2008/0096238 A1 | 4/2008 | Sharif et al. | |
| 2008/0125427 A1 | 5/2008 | Sehon et al. | |
| 2008/0139595 A1 | 6/2008 | Schirok et al. | |
| 2008/0153799 A1 | 6/2008 | Laurent et al. | |
| 2008/0153813 A1 | 6/2008 | Chen et al. | |
| 2008/0161297 A1 | 7/2008 | Bosanac et al. | |
| 2008/0194584 A1 | 8/2008 | Birault et al. | |
| 2008/0275029 A1 | 11/2008 | Berdini et al. | |
| 2008/0287516 A1 | 11/2008 | Wu et al. | |
| 2009/0005321 A1 | 1/2009 | Zimmer et al. | |
| 2009/0069371 A1 | 3/2009 | deLong et al. | |
| 2009/0143381 A1 | 6/2009 | Ruah et al. | |
| 2009/0186917 A1 | 7/2009 | deLong et al. | |
| 2010/0004239 A1 | 1/2010 | Tang et al. | |
| 2010/0056568 A1 | 3/2010 | Plettenburg et al. | |
| 2010/0063025 A1 | 3/2010 | Plettenburg et al. | |
| 2010/0093790 A1 | 4/2010 | deLong et al. | |
| 2010/0105650 A1 | 4/2010 | Plettenburg et al. | |
| 2010/0144713 A1 | 6/2010 | deLong et al. | |
| 2011/0015204 A1 | 1/2011 | Bencsik et al. | |
| 2011/0039893 A1 | 2/2011 | Kori et al. | |
| 2012/0135984 A1 | 5/2012 | deLong et al. | |
| 2012/0196916 A1 | 8/2012 | deLong et al. | |
| 2013/0137721 A1 | 5/2013 | deLong et al. | |
| 2013/0296363 A1 | 11/2013 | Faroni et al. | |
| 2013/0310370 A1 | 11/2013 | Mizuno | |
| 2013/0318457 A1 | 11/2013 | Bjorklund | |
| 2014/0187617 A1 | 7/2014 | deLong et al. | |
| 2014/0275160 A1 | 9/2014 | Kopczynski | |
| 2014/0275161 A1 | 9/2014 | Kopczynski | |
| 2014/0288086 A1 | 9/2014 | Cui et al. | |
| 2014/0357652 A1 | 12/2014 | Bosanac et al. | |
| 2015/0119419 A1 | 4/2015 | deLong et al. | |
| 2015/0175534 A1 | 6/2015 | Harvey et al. | |
| 2015/0175549 A1 | 6/2015 | deLong et al. | |
| 2015/0266881 A1 | 9/2015 | Tomita et al. | |
| 2015/0297581 A1 | 10/2015 | Bosanac et al. | |
| 2015/0299159 A1 | 10/2015 | deLong et al. | |
| 2016/0016951 A1 | 1/2016 | Schiemann et al. | |
| 2016/0243102 A1 | 8/2016 | Bosanac et al. | |
| 2016/0243105 A1 | 8/2016 | Kopczynski et al. | |
| 2016/0272589 A1 | 9/2016 | deLong et al. | |
| 2016/0280656 A1 | 9/2016 | deLong et al. | |
| 2016/0346269 A1 | 12/2016 | Kopczynski et al. | |
| 2017/0000819 A1 | 1/2017 | Capriotti et al. | |
| 2017/0233381 A1 | 8/2017 | deLong et al. | |
| 2017/0281613 A1 | 10/2017 | Kopczynski et al. | |
| 2018/0050990 A1 | 2/2018 | Sturdivant et al. | |
| 2018/0055833 A1 | 3/2018 | Lin et al. | |
| 2018/0186746 A1 | 7/2018 | deLong et al. | |
| 2018/0244666 A1 | 8/2018 | deLong et al. | |
| 2018/0327381 A1 | 11/2018 | deLong et al. | |
| 2018/0333405 A1 | 11/2018 | Kopczynski et al. | |
| 2018/0344724 A1 | 12/2018 | Kopczynski et al. | |
| 2019/0127346 A1 | 5/2019 | deLong et al. | |
| 2019/0322625 A1 | 10/2019 | deLong et al. | |
| 2020/0129498 A1 | 4/2020 | Kopczynski et al. | |
| 2020/0131171 A1 | 4/2020 | deLong et al. | |
| 2020/0140407 A1 | 5/2020 | deLong et al. | |
| 2020/0276179 A1 | 9/2020 | Kopczynski et al. | |
| 2021/0002253 A1 * | 1/2021 | deLong | C07C 69/76 |

FOREIGN PATENT DOCUMENTS

| | | |
|---|---|---|
| EP | 0389995 | 10/1990 |
| EP | 0482939 | 4/1992 |
| EP | 1541151 | 6/2005 |
| EP | 1550660 | 7/2005 |
| JP | 2005227441 | 8/2005 |
| JP | 2007236388 | 9/2007 |
| JP | 2007246466 | 9/2007 |
| WO | 1993/018028 | 9/1993 |
| WO | 1995/019964 | 7/1995 |
| WO | 1996/010407 | 4/1996 |
| WO | 1997/023223 | 7/1997 |
| WO | 1998/012175 | 3/1998 |
| WO | 1998/020880 | 5/1998 |
| WO | 1998/020881 | 5/1998 |
| WO | 1998/021180 | 5/1998 |
| WO | 1998/021181 | 5/1998 |
| WO | 1998/021182 | 5/1998 |
| WO | 1998/039293 | 9/1998 |
| WO | 1988/050024 | 11/1998 |
| WO | 1998/057930 | 12/1998 |
| WO | 1998/057942 | 12/1998 |
| WO | 1999/002165 | 1/1999 |
| WO | 1999/012895 | 3/1999 |
| WO | 1999/012896 | 3/1999 |
| WO | 1999/012898 | 3/1999 |
| WO | 1999/025358 | 5/1999 |
| WO | 1999/026629 | 6/1999 |
| WO | 1999/032441 | 7/1999 |
| WO | 2000/003736 | 1/2000 |
| WO | 2000/003980 | 1/2000 |
| WO | 2000/071508 | 11/2000 |
| WO | 2000/076970 | 12/2000 |
| WO | 2001/037826 | 5/2001 |
| WO | 2001/047891 | 7/2001 |
| WO | 2001/053268 | 7/2001 |
| WO | 2001/053274 | 7/2001 |
| WO | 2001/056607 | 8/2001 |
| WO | 2002/022576 | 3/2002 |
| WO | 2002/032864 | 4/2002 |
| WO | 2002/085857 | 10/2002 |
| WO | 2002/085859 | 10/2002 |
| WO | 2003/064397 | 8/2003 |
| WO | 2003/068749 | 8/2003 |
| WO | 2003/073999 | 9/2003 |
| WO | 2003/080578 | 10/2003 |
| WO | 2004/029045 | 4/2004 |
| WO | 2004/078747 | 9/2004 |
| WO | 2005/020921 | 3/2005 |
| WO | 2005/035503 | 4/2005 |
| WO | 2005/037257 | 4/2005 |
| WO | 2006/041119 | 4/2006 |
| WO | 2006/051290 | 5/2006 |

(56) References Cited

FOREIGN PATENT DOCUMENTS

| | | |
|---|---|---|
| WO | 2006/062982 | 6/2006 |
| WO | 2006/076706 | 7/2006 |
| WO | 2007/008926 | 1/2007 |
| WO | 2007/008942 | 1/2007 |
| WO | 2007/060028 | 5/2007 |
| WO | 2007/065916 | 6/2007 |
| WO | 2007/076360 | 7/2007 |
| WO | 2007/076367 | 7/2007 |
| WO | 2007/100880 | 9/2007 |
| WO | 2007/0142323 | 12/2007 |
| WO | 2008/011557 | 1/2008 |
| WO | 2008/011560 | 1/2008 |
| WO | 2008/016016 | 2/2008 |
| WO | 2008/036459 | 3/2008 |
| WO | 2008/036540 | 3/2008 |
| WO | 2008/049000 | 4/2008 |
| WO | 2008/049919 | 5/2008 |
| WO | 2008/054999 | 5/2008 |
| WO | 2008/077057 | 6/2008 |
| WO | 2008/077550 | 7/2008 |
| WO | 2008/077551 | 7/2008 |
| WO | 2008/077552 | 7/2008 |
| WO | 2008/077553 | 7/2008 |
| WO | 2008/077554 | 7/2008 |
| WO | 2008/077555 | 7/2008 |
| WO | 2008/077556 | 7/2008 |
| WO | 2008/079880 | 7/2008 |
| WO | 2008/079945 | 7/2008 |
| WO | 2008/086269 | 7/2008 |
| WO | 2008/124665 | 10/2008 |
| WO | 2009/091898 | 7/2009 |
| WO | 2010/011853 | 1/2010 |
| WO | 2010/019903 | 2/2010 |
| WO | 2010/126626 | 11/2010 |
| WO | 2010/127329 | 11/2010 |
| WO | 2010/127330 | 11/2010 |
| WO | 2010/146881 | 12/2010 |
| WO | 2011/085351 A2 | 7/2011 |
| WO | 2012/063237 | 5/2012 |
| WO | 2012/105674 | 8/2012 |
| WO | 2014/144781 | 9/2014 |
| WO | 2016/123627 | 8/2016 |
| WO | 2018/034702 | 2/2018 |
| WO | 2018/045091 | 3/2018 |
| WO | 2018/183911 A1 | 10/2018 |
| WO | 2019/191654 A1 | 10/2019 |
| WO | 2020/056345 A1 | 3/2020 |

OTHER PUBLICATIONS

United States Patent Notice of Allowability for U.S. Appl. No. 11/621,887 dated Oct. 29, 2010 (14 pages).
United States Patent Office Action for U.S. Appl. No. 11/856,740 dated Aug. 16, 2013 (14 pages).
United States Patent Office Action for U.S. Appl. No. 11/856,740 dated Dec. 6, 2010 (12 pages).
United States Patent Office Action for U.S. Appl. No. 11/856,740 dated Jun. 29, 2010 (10 pages).
United States Notice of Allowance for U.S. Appl. No. 12/009,326 dated Feb. 3, 2011 (8 pages).
United States Patent Office Action for U.S. Appl. No. 12/180,259 dated Jul. 5, 2011(11 pages).
United States Patent Office Action for U.S. Appl. No. 12/639,670 dated Jan. 31, 2011 (8 pages).
United States Patent Office Action for U.S. Appl. No. 12/639,670 dated Jul. 27, 2011 (5 pages).
United States Patent Office Action for U.S. Appl. No. 12/694,965 dated May 17, 2012 (13 pages).
United States Patent Office Action for U.S. Appl. No. 12/701,963 dated May 10, 2011 (3 pages).
United States Patent Office Action for U.S. Appl. No. 12/704,822 dated Apr. 30, 2012 (34 pages).
United States Patent Office Action for U.S. Appl. No. 12/704,822 dated May 8, 2014 (13 pages).
United States Patent Office Action for U.S. Appl. No. 12/704,822 dated Oct. 10, 2013 (11 pages).
United States Patent Office Action for U.S. Appl. No. 13/017,708 dated Apr. 3, 2012 (11 pages).
United States Patent Office Action for U.S. Appl. No. 13/230,105 dated Mar. 5, 2012 (8 pages).
United States Patent Office Action for U.S. Appl. No. 13/318,457 dated Jun. 6, 2013 (12 pages).
United States Patent Office Action for U.S. Appl. No. 13/723,811 dated Jan. 27, 2014 (8 pages).
United States Patent Office Action for U.S. Appl. No. 13/723,811 dated Jun. 17, 2014 (6 pages).
United States Patent Office Action for U.S. Appl. No. 13/768,594 dated Jul. 10, 2013 (14 pages).
United States Patent Office Action for U.S. Appl. No. 14/138,592 dated Dec. 9, 2014 (14 pages).
United States Patent Office Action for U.S. Appl. No. 14/138,592 dated Jul. 28, 2014 (17 pages).
United States Patent Office Action for U.S. Appl. No. 14/213,940 dated Oct. 29, 2015 (33 pages).
United States Patent Office Action for U.S. Appl. No. 14/213,961 dated Oct. 30, 2015 (37 pages).
United States Patent Office Action for U.S. Appl. No. 14/273,895 dated Aug. 20, 2014 (8 pages).
United States Patent Office Action for U.S. Appl. No. 14/273,895 dated Dec. 24, 2014 (7 pages).
United States Patent Office Action for U.S. Appl. No. 14/461,597 dated Jan. 30, 2015 (19 pages).
United States Patent Office Action for U.S. Appl. No. 14/583,439 dated Jun. 23, 2015 (6 pages).
United States Patent Office Action for U.S. Appl. No. 14/583,439 dated Oct. 30, 2015 (7 pages).
United States Patent Office Action for U.S. Appl. No. 14/641,962 dated Sep. 22, 2015 (16 pages).
United States Patent Office Action for U.S. Appl. No. 14/754,787 dated Oct. 30, 2015 (20 pages).
United States Patent Office Action for U.S. Appl. No. 14/790,376 dated Jan. 22, 2016 (14 pages).
United States Patent Office Action for U.S. Appl. No. 15/076,216 dated Sep. 1, 2016 (6 pages).
United States Patent Office Advisory Action for U.S. Appl. No. 11/856,740 dated Feb. 10, 2011 (3 pages).
United States Patent Office Final Rejection for U.S. Appl. No. 12/704,822 dated Jan. 16, 2013 (16 pages).
United States Patent Office Final Rejection for U.S. Appl. No. 13/230,105 dated Jul. 9, 2012 (11 pages).
United States Patent Office Final Rejection for U.S. Appl. No. 13/318,457 dated Nov. 27, 2013 (13 pages).
United States Patent Office Final Rejection for U.S. Appl. No. 13/442,263 dated Dec. 6, 2013 (8 pages).
United States Patent Office Notice of Allowability for U.S. Appl. No. 13/017,708 dated Dec. 12, 2012 (5 pages).
United States Patent Office Notice of Allowance for U.S. Appl. No. 11/621,887 dated Feb. 27, 2013 (8 pages).
United States Patent Office Notice of Allowance for U.S. Appl. No. 11/856,740 dated Apr. 1, 2014 (8 pages).
United States Patent Office Notice of Allowance for U.S. Appl. No. 12/009,326 dated Feb. 25, 2013 (8 pages).
United States Patent Office Notice of Allowance for U.S. Appl. No. 12/009,326 dated Jan. 6, 2012 (5 pages).
United States Patent Office Notice of Allowance for U.S. Appl. No. 12/180,259 dated Dec. 19, 2011 (6 pages).
United States Patent Office Notice of Allowance for U.S. Appl. No. 12/180,259 dated Feb. 25, 2013 (8 pages).
United States Patent Office Notice of Allowance for U.S. Appl. No. 12/694,965 dated Nov. 19, 2012 (4 pages).
United States Patent Office Notice of Allowance for U.S. Appl. No. 12/694,965 dated Nov. 2, 2012 (8 pages).
United States Patent Office Notice of Allowance for U.S. Appl. No. 12/704,822 dated Sep. 9, 2014 (11 pages).

(56) References Cited

OTHER PUBLICATIONS

United States Patent Office Notice of Allowance for U.S. Appl. No. 13/017,708 dated Oct. 23, 2012 (7 pages).
United States Patent Office Notice of Allowance for U.S. Appl. No. 13/017,708 dated Sep. 17, 2012 (8 pages).
United States Patent Office Notice of Allowance for U.S. Appl. No. 13/230,105 dated Mar. 19, 2013 (5 pages).
"Cancer", MedlinePlus (retrieved Jul. 6, 2007) 10 pages, http://www.nlm.nih.gov/medlineplus/cancer.html.
Anonymous, "Aerie Pharmaceuticals, Inc. Gets Good News on Glaucoma Treatment" (Feb. 11, 2012) Retrieved from the Internet: URL:http://www.biospace.com.
Australian Patent Examination Report No. 1 for Application No. 2009206075 dated Jan. 29, 2013 (3 pages).
Australian Patent Examination Report for Application No. 2016201754 dated Oct. 19, 2016 (4 pages).
Australian Patent Examination Report No. 1 for Application No. 2010241996 dated Apr. 1, 2015 (4 pages).
Australian Patent Office Action for Application No. 2010241996 dated Mar. 21, 2016 (3 pages).
Banker, G.S et al., Modern Pharmaceutics, Marcel Dekker, Inc., New York, (1979) Chapters 9 and 10.
Basu et al., Ultrasound-promoted highly efficient reduction of aromatic nitro compounds to the aromatic amines by samarium/ammonium chloride. Tetrahedron Letters, 41:5603-5606 (2000).
International Search Report and Written Opinion for International Application No. PCT/US2017/025609 dated Jul. 3, 2017 (8 pages).
International Search Report and Written Opinion for International Application No. PCT/US2017/065631 dated Feb. 13, 2018 (6 pages).
Ito, N. et al., "A medium-term rat liver bioassay for rapid in vivo detection of carcinogenic potential of chemicals," Cancer Science, Jan. 2003, vol. 94, No. 1, pp. 3-8.
Jacobs, M. et al., "The structure of dimeric ROCK I reveals the mechanism for ligand selectivity," J Bio Chem., 2006, pp. 260-268, published on Jan. 6, 2006.
Japanese Patent Office Action for Application No. 2009-545622 dated Mar. 1, 2013 (8 pages—including English Translation).
Japanese Patent Office Action for Application No. 2009-545622 dated Oct. 21, 2013 (8 pages—Including English Translation).
Japanese Patent Office Action for Application No. 2010-543237 dated Aug. 8, 2013 (10 pages—Including English Translation).
Japanese Patent Office Action for Application No. 2010-543237 dated Jan. 8, 2014 (2 pages—Including English Translation).
Japanese Patent Office Action for Application No. 2011-520203 dated Jan. 28, 2014 (8 pages, English translation included).
Japanese Patent Office Action for Application No. 2012-508492 dated Apr. 2, 2015 (4 pages, English translation included).
Japanese Patent Office Action for Application No. 2012-508492 dated Apr. 7, 2014 (5 pages, English translation only).
Japanese Patent Office Action for Application No. 2014-131231 dated Jan. 14, 2015 (8 pages, English translation attached).
Japanese Patent Office Action for Application No. 2014-131231 dated Jan. 27, 2016 (3 pages, English translation only).
Japanese Patent Office Action for Application No. 2015-216395 dated Nov. 14, 2016 (7 pages including translation).
Karaman, M.W. et al., "A quantitative analysis of kinase inhibitor selectivity," Nature Biotech. (2008) 26(1):127-132.
Katritzky, A.R. et al., "Benzotriazole mediated amino-, amide-, alkoxy- and alkylthio-alkylation," Tetrahedron (2005) 61:2555-2581.
Kumar et al., Catalyst-free water mediated reduction of nitroarenes using glucose as a hydrogen source. RSC Advances, 3:4894-4898 (2013).
Lala, P.K. et al., "Role of nitric oxide in tumor progression: lessons from experimental tumors," Cancer and Metastasis Reviews (1998) 17:91-106.
Liljebris, C. et al., "Derivatives of 17-Pheny 1-18,19 ,20-trinorprostaglandin F2a Isopropyl Ester: Antiglaucoma Agents," J. Med. Chem. (1995) 38(2):289-304.
Loge et al., Synthesis and pharmacological study of rho-kinase inhibitors: Pharmacomodulations on the lead compound Fasudil. J. of Enzy Inhib & Med Chem, 2003,18(2),127-128.
Matsui et al., "Novel 5-HT3 antagonists. Isoquinolinones and 3-aryl-2-pyridones." J. Med. Chem. (1992) 35:3307-3319.
McCutcheon's, "Emulsifiers & Detergents", North American Edition (1994) vol. 1:236-239.
Meanwell, "Synopsis of some recent tactocal application of bioisosteres in drug design," J. Med. Chem., 2011, vol. 54, pp. 2529-2591.
Nakanishi et al., Effects of protein kinase inhibitors and protein phosphatase inhibitors on cyclic AMP-dependent down-regulation of vesicular monoamine transport in pheochromocytoma PC12 cells. FEBS Letters 368, (1995) 411-414.
Oakley et al., "The Cellular Distribution of Fluorescently Labeled Arrestins Provides a Robust, Sensitive and Universal Assay for Screening G Protein-Coupled Receptors." Assay and Drug Development Technologies vol. 1, No. 1-1:21-30 (2002).
Olson, "Application for ROCK kinase inhibition," Current Opinion in Cell Biology, 2008, vol. 20, pp. 242-248.
Parang et al., "Design strategies for protein kinase inhibitors." Curr. Opin. In Drug Disc. & Dev. (2004) 7(5):617-629.
Pardridge, "The Blood-Brain Barrier: Bottleneck in Brain Drug development," J. Am. Soc. Exper. NeuroTherapeutics, 2005, vol. 2, p. 3-14.
Partial International Search Report and Invitation to pay Additional Fees for Application No. PCT/US2009/031117 dated Apr. 16, 2009 (4 pages).
Penmetsa et al., Development of Reversed-Phase Chiral HPLC Methods Using Mass Spectrometry Compatible Mobile Phases. J. Liquid Chroma. & Rel. Tech. 23(6):831-839 (2000).
Penn et al., "Pharmacological Inhibition of Protein Kinases in Intact Cells: Antagonism of Beta Adrenergic Receptor Ligand Binding by H-89 Reveals Limitations of Usefulness." J. Pharm. Exp. Ther. 288(2):428-437 (1999).
Pharmasolve (N-Methyl-2-Pyrrolidone) product spcification, International Specialty Products, 2000, 10 pages.
Poradowska et al., The Preparation of 6-Aminoisoquinoline. Synthesis 11:733, 1975.
Pubchem, AC1 NQAJU (compound sumary for CID 5172372) '372' date created: Sep. 26, 2005 date access: Jan. 5, 2016, 10 pages.
Rashid et al., "Development of Rho-kinase inhibitors for cardiovascular medicine," Trends in Pharmacological Science, 2007, vol. 28, pp. 296-302.
Shankar et al., "Protein-kinase-specific inhibitors block Langerhans' cell migration by inhibiting interleukin-1 alpha release." Immunology (1999) 96:230-235.
Sharma et al., Highly Chemo- and Regioselective Reduction of Aromatic Nitro Compounds Catalyzed by Recyclable Copper(II) as well as Cobalt(II) Phthalocyanines. Advanced Synthesis and Catalysis, 352:1834-1840 (2010).
Sharma et al., Zinc phthalocyanine with PEG-400 as a recyclable catalytic system for selective reduction of aromatic nitro compounds. Green Chem., 14:2289-2293 (2012).
Sharma et al., Phosphane-Free Green Protocol for Selective Nitro Reduction with an Iron-Based Catalyst. Chem. Eur. J., 17:5903-5907 (2011).
Stirewalt et al., "The Role of FLT3 In Haematopoietic Malignancies." Nature Reviews Cancer (2003) 3:650-665.
STN Registry Database entry for CAS RN 309930-43-6, Published in database Dec. 20, 2000.
Sturdivant et al., Discovery of the ROCK inhibitor netarsudil for the treatment of open-angle glaucoma. Bioorganic & Medicinal Chemistry Letters, 26:2475-2480 (2016).
Sturdivant et al., Identification of intermediates in the stepwise reduction of 1,3-dichloro-6-nitroisoquinoline to 6-aminoisiquinoline. 248th National Meeting of the American Chemical Society, Aug. 2014, MEDI 153.
Tamura, M., et al., "Development of specific Rho-kinase inhibitors and their clinical application," Biochimica et Biophysica Acta, 2005, vol. 1754, pp. 245-252.
Torres, G.E. et al. (2003). "Plasma membrane monoamine transporters: structure, regulation and function". Nat. Rev. Neurosci. 4 (1): 13-25.

(56) References Cited

OTHER PUBLICATIONS

United States Office Action for U.S. Appl. No. 11/485,182 dated Apr. 16, 2009 (13 pages).
United States Office Action for U.S. Appl. No. 11/621,892 dated Aug. 8, 2008 (9 pages).
United States Office Action for U.S. Appl. No. 11/621,892 dated Mar. 9, 2009 (6 pages).
United States Office Action for U.S. Appl. No. 12/274,887 dated Jun. 16, 2009 (11 pages).
United States Patent Office Action for U.S. Appl. No. 11/621,887 dated May 18, 2010 (8 pages).
Chinese Patent Office Action for Application No. 201480027763.3 dated Nov. 1, 2016 (18 pages including translation).
Dancey, J. et al., "Issues and Progress with Protein Kinase Inhibitors for Cancer Treatment", Nature Reviews Drug Discovery (2003) 2:296-313.
deLong et al., "Discovery and SAR of a Class of Oculary-active Compounds Displaying a Dual Mechanism of Activity for the Treatment of Glaucoma" (May 6-10, 2012) Retrieved from the Internet:URL:http://www.aeriepharma.com.
Dorwald, F.Z., Side Reactions in Organic Synthesis. A Guide to Successful Synthesis Design, Wiley-VCH, Weinheim (2005) IX of Preface and 1-15.
Dowton et al., "Influence of Liposomal Composition on Topical Delivery of Encapsulated Cyclosporin A", S.T.P. Pharma Sciences, vol. 3, pp. 404-407 (1993).
Ehara et al.. Structure-based design of substituted piperidines as a new class of highly efficacious oral direct renin inhibitors. ACS Medicinal Chemistry Letters, 5(7):787-792 (2014).
Ehara, abstract only, CA 161:93707 (2014).
European Patent Office Action for Application No. 08713603.2 dated Aug. 14, 2012 (3 pages).
European Patent Office Action for Application No. 08713603.2 dated Nov. 21, 2013 (4 pages).
European Patent Office Action for Application No. 09702189.3 dated Feb. 1, 2011 (5 pages).
European Patent Office Action for Application No. 09702189.3 dated Dec. 28, 2011 (5 pages).
European Patent Office Action for Application No. 09790775.2 dated Oct. 24, 2011 (5 pages).
European Patent Office Search Report for Application No. 15002893.4 dated Jun. 27, 2016 (5 pages).
Extended European Search Report for European Patent Application No. 12007093.3 dated Nov. 23, 2012 (5 pages).
European Patent Office Action for Application No. 12007093.3 dated Mar. 26, 2014 (4 pages).
European Patent Office Action for Application No. 12007093.3 dated Aug. 23, 2013 (5 pages).
European Patent Office Action for Application No. 12007092.5 dated Nov. 23, 2012 (5 pages).
Extended European Search Report for European Patent Application No. 12007089.1 dated Nov. 23, 2012 (5 pages).
European Search Report for European Application No. 18160338.2 dated May 25, 2018 (6 pages).
Examination Report from the Australian Patent Office for Application No. 2008205047 dated Nov. 26, 2012 (6 pages).
Examination Report from the Australian Patent Office for Application No. 2009273932 dated Mar. 13, 2013 (3 pages).
Examination Report from the Australian Patent Office for Application No. 2009273932 dated Jun. 6, 2014 (2 pages).
Fox et al., 19F and 13C GIAO-NMR chemical shifts for the identification of perfluoro-quinoline and -isoquinoline derivatives Journal of Fluorine Chemistry, 155, pp. 62-71 (2013).
Foye, Foye's Principles of Medicinal Chemistry, 5th Edition (2002) Lippencott, Williams, Wilkins, p. 59-63.
Gingras et al., "In Synthesis and evaluation of 4-(1-aminoalkyl)-N-(4-pyridyl)-cyclohexanecarboxamides as Rho-kinase inhibitors and neurite outgrowth promoters," Bioorganic & Medicinal Chemistry Letters, 2004, vol. 14, pp. 4931-4934.

Golub, T.R. et al., "Molecular classification of cancer: class discovery and class prediction by gene expression monitoring," Science (1999) 286:531-537.
Guha et al., Solid supported rhodium(0) nanoparticles: an efficient catalyst for chemo- and regio-selective transfer hydrogenation of nitroarenes to anilines under microwave irradiation. Tetradedron Letters, 55:2912-2916 (2014).
Hackam, A.S. et al., "The Wnt Signaling Pathway in Retinal Degenerations", IUBMB Life (2005) 57(6):381-388.
Hazeldine, S.T. et al., "II. Synthesis and biological evaluation of some bioisosteres and cogeners of the anti tumour agent, 2{4[7-chloro-2-quinoxalinyl)oxy]phenoxy}propionic acid (XK469)," J Med. Chem. (2002) 45:3130-3137.
He et al., "Further structure-activity relationship studies of piperidine-based monoamine transporter inhibitors: effects of piperidine ring stereochemistry on potency. Identification of norepinephrine transporter selective ligands and broad-spectrum transporter inhibitors". J. Med. Chem. 48 (25): 7970-9 (2005).
Helal, C.J. et al., "Discovery and SAR of 2-aminothiazole inhibitors of cyclin-dependent kinase 5/p25 as a potential treatment for Alzheimer's disease," Bioorg. Med. Chem. (2004) 14(22):5521-5525.
Helzner, "Bright New Ideas in Glaucoma Treatment" (2013) Retreived from the Internet: URL:http://mydigimag.rrd.com.
Hu, E. et al., "Rho kinase as potential therapeutic target for cardiovascular diseases: opportunities and challenges," Exp. Opin. Ther. Targets (2005) 9:715-736.
Inouye, Y. et al., "The Absolute Configurations of TRANS-1,2 Cyclopropanedicarboxylic Acid and TRANS-2-Phenylcyclopropanecarboxylic Acid", Int'l. J. Org. Chem. (1964) 20(5): 1695-1699.
International Search Report and Written Opinion for Application No. PCT/US2015/61177 dated Feb. 2, 2016 (16 pages).
International Preliminary Examination Report for Application No. PCT/US2006/026947 dated Jan. 24, 2008 (10 pages).
International Preliminary Report on Patentability for Application No. PCT/US08/50374 dated Jul. 14, 2009 (12 pages).
International Search Report and Written Opinion for Application No. PCT/US2006/026976 dated Feb. 15, 2007 (14 pages).
International Search Report and Written Opinion for Application No. PCT/US2007/078343 dated Apr. 15, 2008 (12 pages).
International Search Report and Written Opinion for Application No. PCT/US2009/031117 dated Sep. 24, 2009 (13 pages).
International Search Report and Written Opinion for Application No. PCT/US2009/051569 dated May 20, 2010 (11 pages).
International Search Report and Written Opinion for Application No. PCT/US2010/022246 dated Nov. 10, 2010 (7 pages).
International Search Report and Written Opinion for Application No. PCT/US2010/33316 dated Jul. 14, 2010 (10 pages).
International Search Report and Written Opinion for Application No. PCT/US2010/33317 dated Aug. 17, 2010 (10 pages).
International Search Report and Written Opinion for Application No. PCT/US2014/029335, dated Jul. 2, 2014 (11 pages).
Al-Rashida et al., Diarylsulfonamides and their bioisosteres as dual inhibitors of alkaline phosphatase and carbonic anhydrase: Structure activity/relationship and molecular modelling studies. Bioorganic & Medicinial Chemistry, vol. 23, Issue 10, pp. 2435-2444 (2015).
International Search Report for Application No. PCT/US08/50374 dated Oct. 28, 2008 (7 pages).
International Search Report for Application No. PCT/US2006/026947 dated Nov. 17, 2006 (4 pages).
Invitation to Pay Additional Fees and Partial International Search Report for International Application No. PCT/US2009/051569 dated Oct. 15, 2009 (4 pages).
International Search Report and Written Opinion for International Application No. PCT/US2017/049473 dated Nov. 30, 2017 (15 pages).
Berge et al, 1977, "Pharmaceutically Acceptable Salts." J. Pharm. Sci. vol. 66, pp. 1-19.
Bird, G.J. et al., "N-methyl as a bioisostere for the oxygen link between the aromatic rings of aryloxyphenoxypropionate herbicides," Bioorg. Med. Chem. Lett. (1997) 7:1489-1492.

(56) References Cited

OTHER PUBLICATIONS

Blough BE, Keverline KI, Nie Z, Navarro H, Kuhar MJ, Carroll FI (2002). "Synthesis and transporter binding properties of 3beta-[4'-(phenylalkyl, phenylalkenyl, and phenylalkynyl) phenyltropane]-2beta-carboxylic acid methyl esters evidence of a remote phenyl binding domain on the dopamine transporter". J. Med. Chem. 45 (18):4029-37.

C.T.F.A. Cosmetic Ingredient Handbook, "Surfactants—Emulsifying Agents", Second Edition, The Cosmetic, Toiletry, and Fragrance Association, New York, Wenninger, J.A. et al., eds. (1992) 587-592.

Calmes et al., Asymmetric Synthesis of (S)-beta2-Homoarylglycines. Eur. J. Org. Chem. 2000, 2459-2466.

Canadian Patent Office Action for Application No. 2,731,869 dated Jun. 9, 2015 (3 pages).

Canadian Patent Office Action for Application No. 2,731,869 dated Feb. 18, 2016 (4 pages).

Canadian Patent Office Action for Application No. 2,760,562 dated Feb. 2, 2015 (4 pages).

Canadian Patent Office Action for Application No. 2,760,562 dated Jul. 3, 2015 (3 pages).

Canadian Patent Office Action for Application No. 2,712,443 dated Dec. 27, 2013 (3 pages).

Capdeville, R. et al., "Glivec (STI571, IMATINIB), A Rationally Developed, Targeted Anticancer Drug", Nature Reviews Drug Discovery (2002) 1:493-502.

Chen, P. et al., "Identification of novel and potent isoquinoline aminooxazole-based IMPDH inhibitors," Bioorg. Med. Chem. Lett. (2003) 13(7):1345-1348.

Cheung et al., N-methylamino acids in peptide synthesis. V. The syntesis of N-tert-butyloxycarbonyl, N-methylamino acids by N-methylation. Can. J Chem. 1977, 55,906-910.

United States Patent Office Notice of Allowance for U.S. Appl. No. 13/442,263 dated Apr. 15, 2014 (8 pages).

United States Patent Office Action for U.S. Appl. No. 13/442,263 dated Dec. 19, 2012 (13 pages).

European Search Report for European Patent Application No. 18206195.2 dated Feb. 11, 2019 (10 pages).

United States Patent Office Action for U.S. Appl. No. 13/442,263 dated Jun. 12, 2013 (17 pages).

United States Patent Office Notice of Allowance for U.S. Appl. No. 13/723,811 dated Aug. 19, 2014 (11 pages).

United States Patent Office Notice of Allowance for U.S. Appl. No. 13/768,594 dated Oct. 29, 2013 (7 pages).

United States Patent Office Notice of Allowance for U.S. Appl. No. 14/213,961 dated Jun. 20, 2016 (8 pages).

United States Patent Office Notice of Allowance for U.S. Appl. No. 14/273,895 dated Apr. 1, 2015 (8 pages).

United States Patent Office Notice of Allowance for U.S. Appl. No. 14/583,439 dated Feb. 12, 2016 (8 pages).

United States Patent Office Notice of Allowance for U.S. Appl. No. 14/790,376 dated Aug. 2, 2016 and supplemental Notice of Allowability dated Aug. 19, 2016 (10 pages).

Yamashita et al., "The therapeutic effects of Rho-Rock inhibitors on CNS disorder," Therapeutics and Clinical Risk Management, 2008, vol. 4, pp. 605-615.

International Search Report and Written Opinion dated Aug. 23, 2018 for International Application No. PCT/US2018/025494 filed on Mar. 30, 2018.

Westra et al., "p38 Mitogen-Activated Protein Kinase (MAPK) in Rheumatoid Arthritis." Mini-Reviews in Medicinal Chemistry (2006) 6(8):867-874.

Westaway et al., "N-tetrahydroquinolinyl, N-quinolinyl and N-isoquinolinyl biaryl carboxamides as antagonists of TRPV1." Biorg. Med. Chem. Lett. (2006) 16:4533-4536.

Van Muijl Wijk-Koezen et al., "A novel class of adenosine A3 receptor-ligands. 2. Structure affinity profile of a series of isoquinoline and quinazoline compounds." J. Med. Chem. (1998) 41:3994-4000.

Vippagunta et al., "Cystalline solids." Advanced Drug Delivery Reviews, 48:3-26 (2001).

Wallach and Philippot, "New Type of Lipid Vesicle: Novasome®", Liposome Technology, vol. 1, pp. 141-156 (1993).

Webster, F.X. et al., "Following the Course of Resolution of Carboxylic Acids by 13C NMR Spectrometry of Amine Salts" J. Org. Chem. (1982) 47(26):5225-5226.

West, A.R., "Solid state chemistry and its applications," Wiley, New York (1988) pp. 358 and 365.

International Search Report and Written Opinion dated Nov. 15, 2019, for International Patent Application Serial No. PCT/US2019/051136 filed on Sep. 13, 2019.

Donegan et al., Discovery of molecular therapeutics for glaucoma: Challenges, successes, and promising directions. Journal of Medicinal Chemistry, vol. 59, Issue 3, pp. 788-809 (2016).

International Search Report and Written Opinion dated Jul. 25, 2019, for International Patent Application Serial No. PCT/US2019/024954 filed on Mar. 29, 2019.

International Patent Application Serial No. PCT/US2019/051136 filed on Sep. 13, 2019.

U.S. Appl. No. 16/435,254, filed Jun. 7, 2019.

U.S. Appl. No. 16/680,359, filed Nov. 11, 2019.

U.S. Appl. No. 16/712,186, filed Dec. 12, 2019.

Bhatia et al., A review on Bioisosterism: A Rational approach for drug design and molecular modification. Pharmacologyonline, 1:272-299 (2011).

Gould, Philip L., Salt selection for basic drugs. International Journal of Pharmaceutics, vol. 33, pp. 201-217 (1986).

Rowe et al., Boric Acid. Handbook of Pharmaceutical Excipients, Fifth Edition (2006). Pharmaceutical Press and American Pharmacists Association.

Yingling et al., ARVO Annual Meeting Abstract, Apr. 2009, IOP-Lowering Efficacy and Tolerability of AR-12286, a Potent Kinase Inhibitor for the Treatment of Glaucoma. Investigative Ophthalmology & Visual Science, Apr. 2009, vol. 50, 4063 (2009).

Williams et al., Ocular hypotensive effect of the Rho kinase inhibitor AR-12286 in patients with glaucoma and ocular hypertension. Am. J. Ophthalmol., vol. 152, p. 834-841 (2011).

* cited by examiner

```
SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: RSK2 peptide

<400> SEQUENCE: 1

Lys Arg Arg Arg Leu Ser Ser Leu Arg Ala
1               5                   10

<210> SEQ ID NO 2
<211> LENGTH: 12
<212> TYPE: PRT
<213> ORGANISM: Artificial Sequence
<220> FEATURE:
```

```
<223> OTHER INFORMATION: Abl peptide

<400> SEQUENCE: 2

Glu Ala Ile Tyr Ala Ala Pro Phe Ala Lys Lys Lys
1               5                   10
```

ARYL CYCLOPROPYL-AMINO-ISOQUINOLINYL AMIDE COMPOUNDS

RELATED APPLICATIONS

This application claims the priority of U.S. Provisional Patent Application No. 62/731,609, filed Sep. 14, 2018, and U.S. Provisional Patent Application No. 62/738,962, filed Sep. 28, 2018, the entire content of each of which is incorporated herein by reference.

SEQUENCE LISTING

This application contains a sequence listing having the filename 1959002-00143_ST25.txt, which is 620 bytes in size, and was created on Sep. 13, 2018. The entire content of this sequence listing is herein incorporated by reference.

BACKGROUND

A variety of hormones, neurotransmitters and biologically active substances control, regulate or adjust the functions of living bodies via specific receptors located in cell membranes. Many of these receptors mediate the transmission of intracellular signals by activating guanine nucleotide-binding proteins (G proteins) to which the receptor is coupled. Such receptors are generically referred to as G-protein coupled receptors (GPCRs) and include, among others, α-adrenergic receptors, β-adrenergic receptors, opioid receptors, cannabinoid receptors and prostaglandin receptors. The biological effects of activating or inhibiting these receptors is not direct, but is mediated by a host of intracellular proteins. The importance of these secondary proteins has been recognized and modulation of this class is now being investigated as intervention points in disease states. One of the most important classes of these downstream effectors is the "kinase" class.

The various kinases play important roles in the regulation of various physiological functions. For example, kinases have been implicated in a number of disease states, including, but not limited to: cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis. The importance of p38 MAPK inhibitors in particular as new drugs for rheumatoid arthritis is reflected by the large number of compounds that has been developed over the last years (J. Westra and P. C. Limburg Mini-Reviews in Medicinal Chemistry Volume 6, Number 8, August 2006). Other conditions include chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (e.g., cardiac malformations), neurodegenerative diseases such as Parkinson's Disease and Alzheimer's Disease, multiple sclerosis, Epstein-Barr infection and cancer (*Nature Reviews Drug Discovery* 2002, 1: 493-502). In other disease states, the role of kinases is only now becoming clear. The retina is a complex tissue composed of multiple interconnected cell layers, highly specialized for transforming light and color into electrical signals that are perceived by the brain. Damage or death of the primary light-sensing cells, the photoreceptors, results in devastating effects on vision. Despite the identification of numerous mutations that cause inherited retinal degenerations, the cellular and molecular mechanisms leading from the primary mutations to photoreceptor apoptosis are not well understood, but may involve the wnt pathway (AS Hackam "The Wnt Signaling Pathway in Retinal Degeneration" *IUBMB Life Volume* 57, Number 6/June 2005).

The success of the tyrosine-kinase inhibitor STI571 (Gleevec) in the treatment of chronic myelogenous leukemia (*Nature Reviews Drug Discovery* 2003, 2: 296-313) has spurred considerable efforts to develop other kinase inhibitors for the treatment of a wide range of other cancers (Nature Reviews Cancer 2003, 3: 650-665). The balance between the initiation and the inactivation of intracellular signals determines the intensity and duration of the response of the receptors to stimuli such as agonists. When desensitization occurs, the mediation or regulation of the physiological function mediated or regulated by the G proteins to which the receptors are coupled is reduced or prevented. For example, when agonists are administered to treat a disease or condition by activation of certain receptors, the receptors relatively quickly become desensitized from the action of the GRKs such that agonist administration may no longer result in therapeutic activation of the appropriate receptors. At that point, administration of the agonist no longer enables sufficient or effective control of or influence on the disease or condition intended to be treated.

Janus Kinases (or JAK) are a family of cytoplasmic protein tyrosine kinases. The JAK family plays a role in the cytokine-dependent regulation of proliferation and function of cells involved in immune response. Currently, there are four JAK family members are known JAK1, JAK2, JAK3, and TYK2. The JAKs usually associate with cytokine receptors in pairs as homodimers or heterodimers. Specific cytokines are associated with specific JAK pairings. Each of the four members of the JAK family is implicated in the signaling of at least one of the cytokines associated with inflammation. Binding of cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease.

In view of the role that kinases play in many disease states, there is an urgent and continuing need for small molecule ligands which inhibit or modulate the activity of kinases. Without wishing to be bound by theory, it is thought that modulation of the activity of kinases, in particular ROCK and JAK kinases, by the compounds of the present disclosure is, at least in part, responsible for their beneficial effects.

SUMMARY

In one aspect, provided herein are compounds of Formula (I):

(I)

or a pharmaceutically acceptable salt thereof,
wherein
$R^1$ is H, halo, —CN, —$C_{1-6}$ alkyl, —$C_{1-6}$ alkoxyl, —$C_{1-6}$ haloalkyl, —$C_{1-6}$ haloalkoxyl;
$R^2$ is H or halo;
X is —($C_{1-5}$ heteroaryl)—$R^3$; and
$R^3$ is halo, —$C_{2-6}$ heterocyclyl, or —$C_{1-6}$ heteroalkyl.

In one aspect, provided herein are compounds of Formula (Ia):

(Ia)

or a pharmaceutically acceptable salt thereof,
wherein
$R^1$ is H, halo, —CN, —$C_{1-6}$ alkyl, —$C_{1-6}$ alkoxyl, —$C_{1-6}$ haloalkyl, —$C_{1-6}$ haloalkoxyl;
$R^2$ is H or halo;
X is —($C_{1-5}$ heteroaryl)-($R^3$)$_n$;
$R^3$ is H, halo, —$C_{2-6}$ heterocyclyl, or —$C_{1-6}$ heteroalkyl; and
n is 1, 2, or 3.

In another aspect, provided herein are compounds of Formula (Ib):

(Ib)

or a pharmaceutically acceptable salt thereof,
wherein
$R^1$ is H, halo, —CN, —$C_{1-6}$ alkyl, —$C_{1-6}$ alkoxyl, —$C_{1-6}$ haloalkyl, —$C_{1-6}$ haloalkoxyl;
$R^2$ is H or halo;
X is —($C_{2-6}$ heterocyclyl)-($R^3$)$_n$;
$R^3$ is H, halo, —$C_{2-6}$ heterocyclyl, or —$C_{1-6}$ heteroalkyl; and
n is 1, 2, or 3.

In another aspect, provided herein are compounds having a structure:

-continued
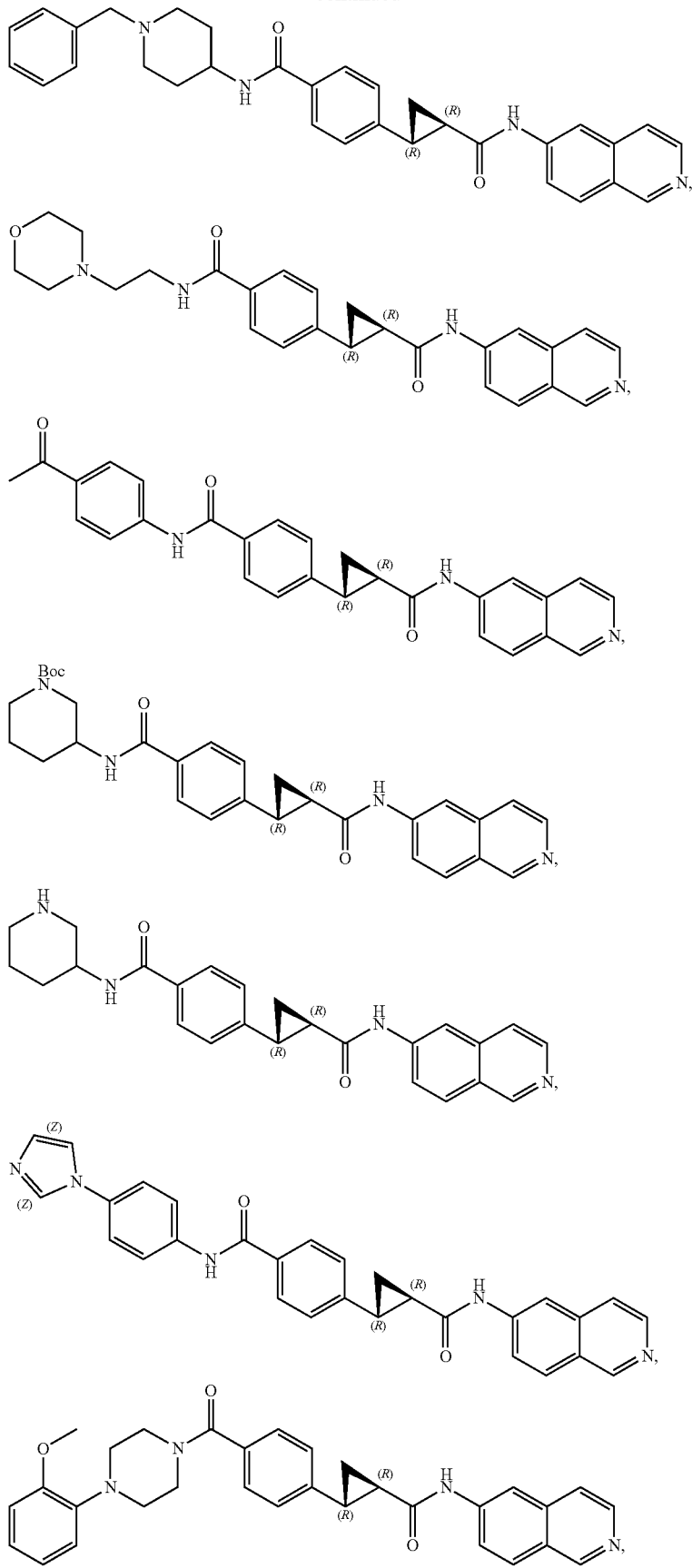

-continued
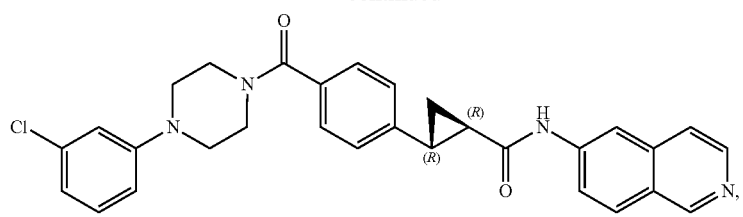
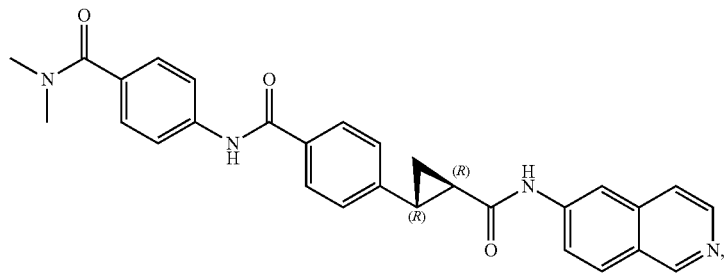
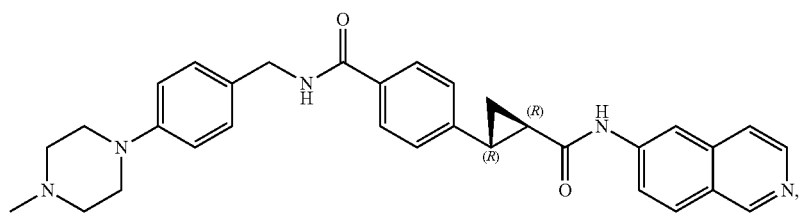
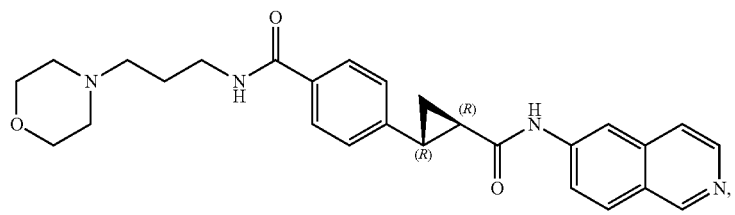
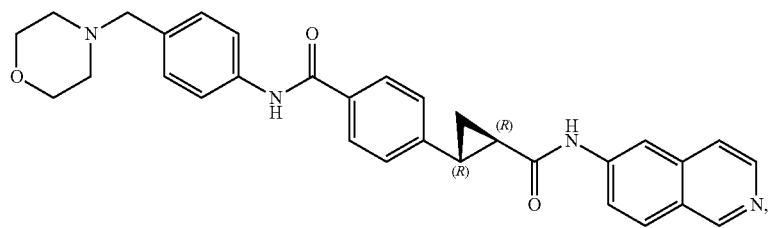
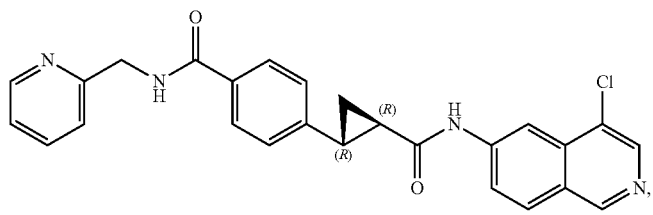
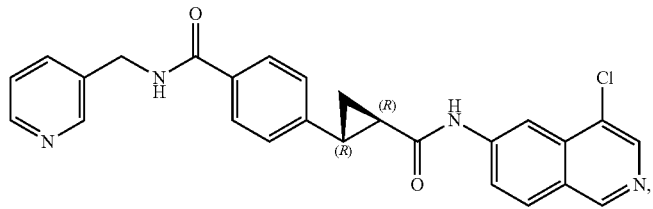

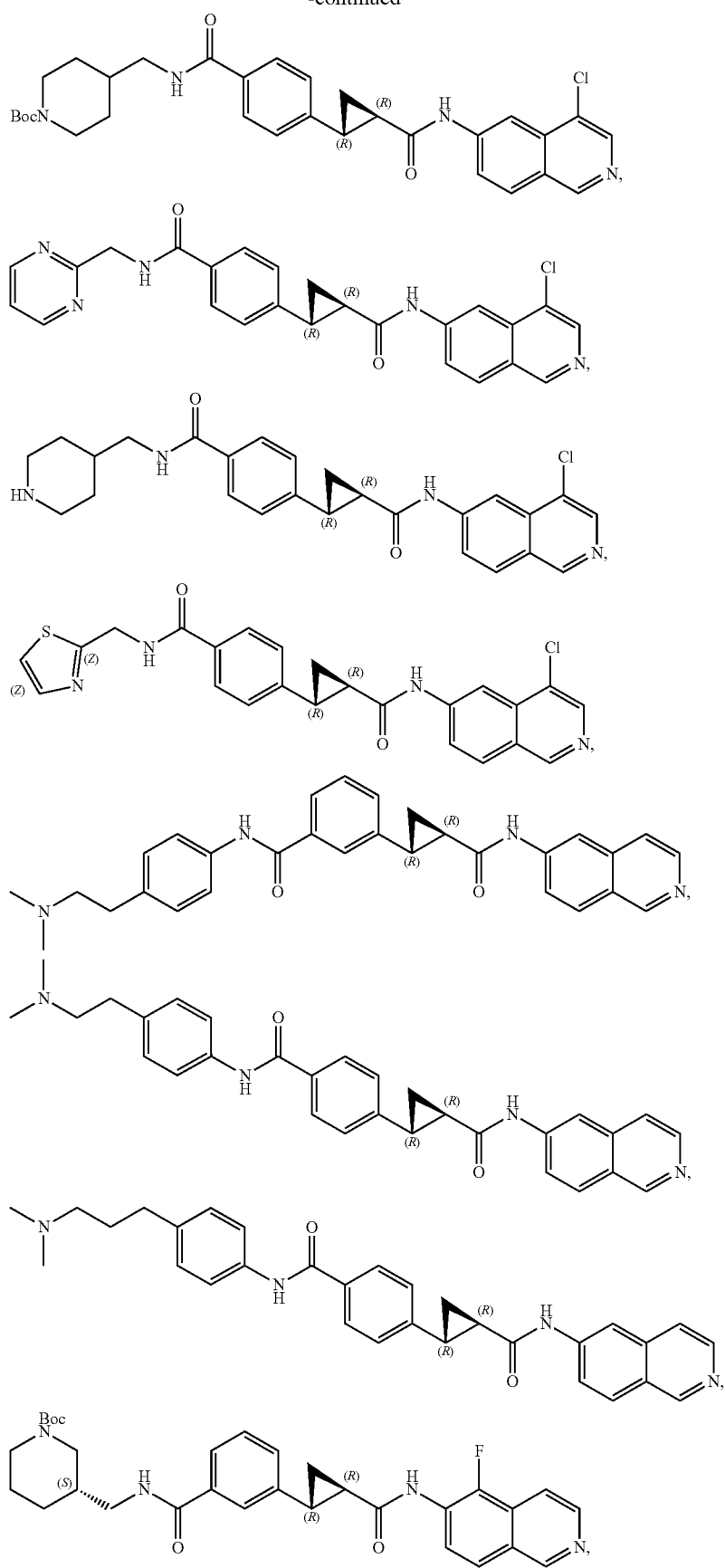

-continued
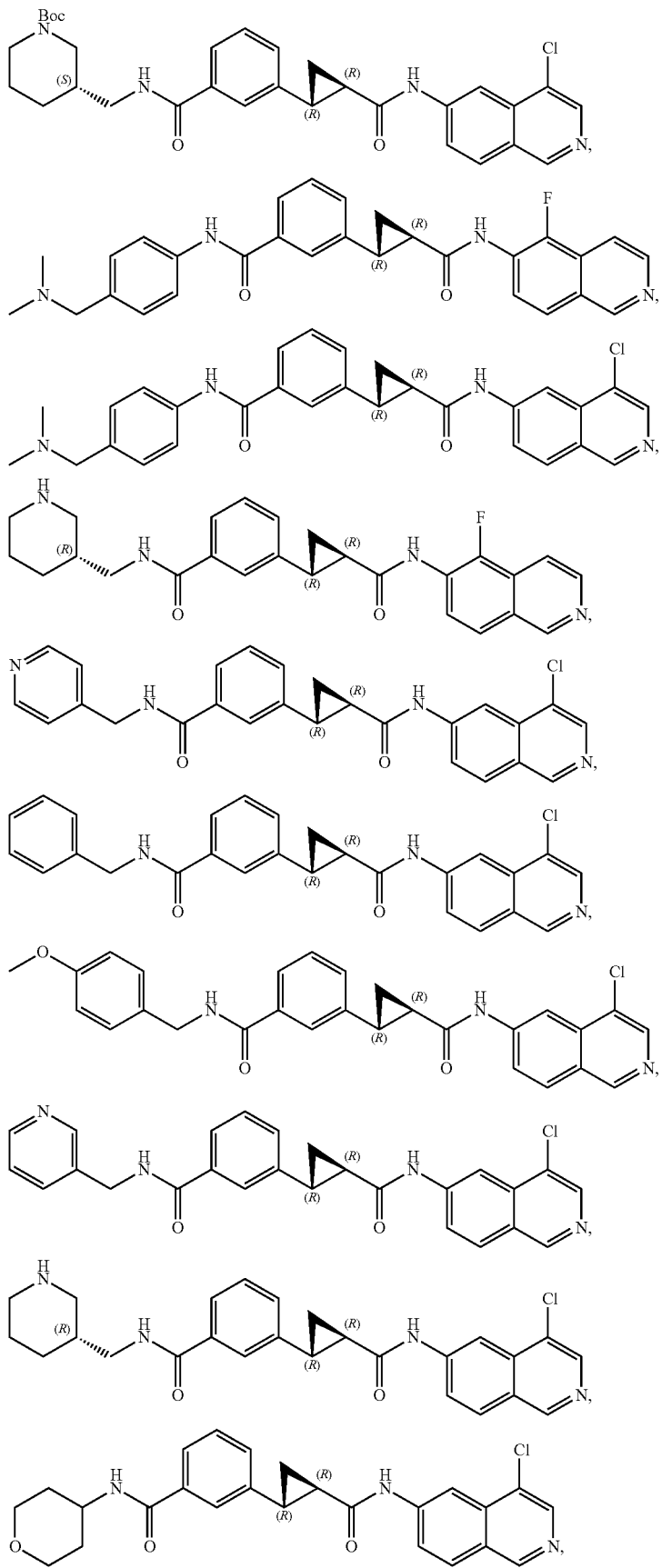

-continued
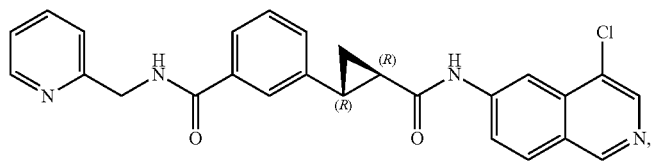
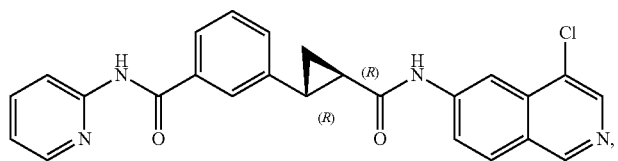
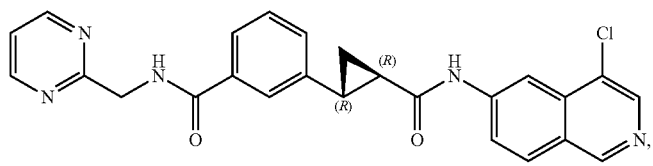
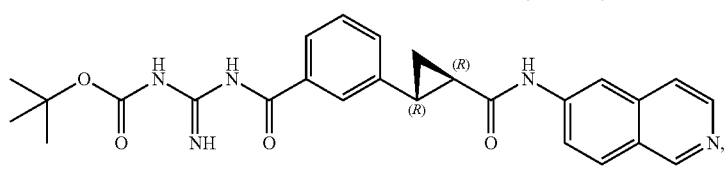
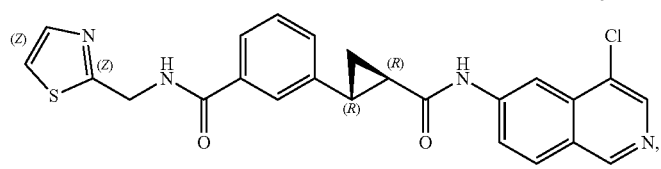
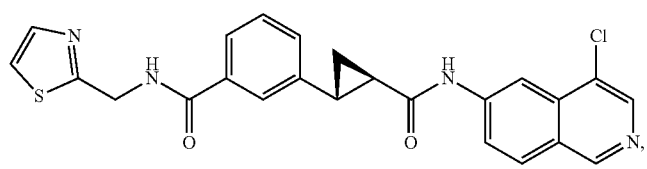
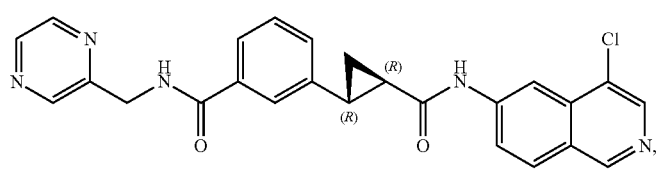
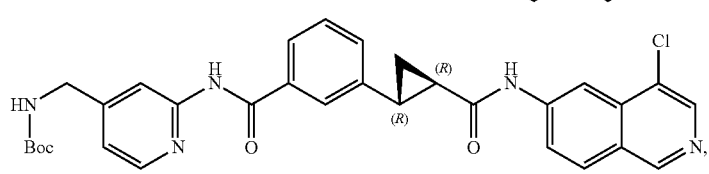
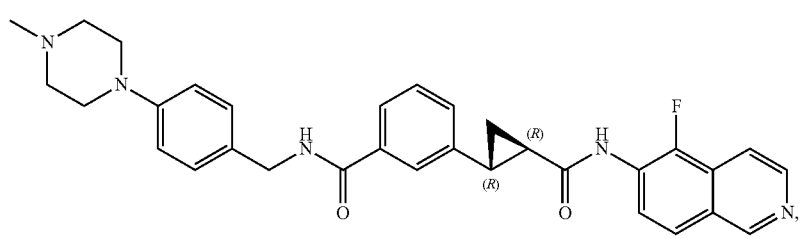

-continued

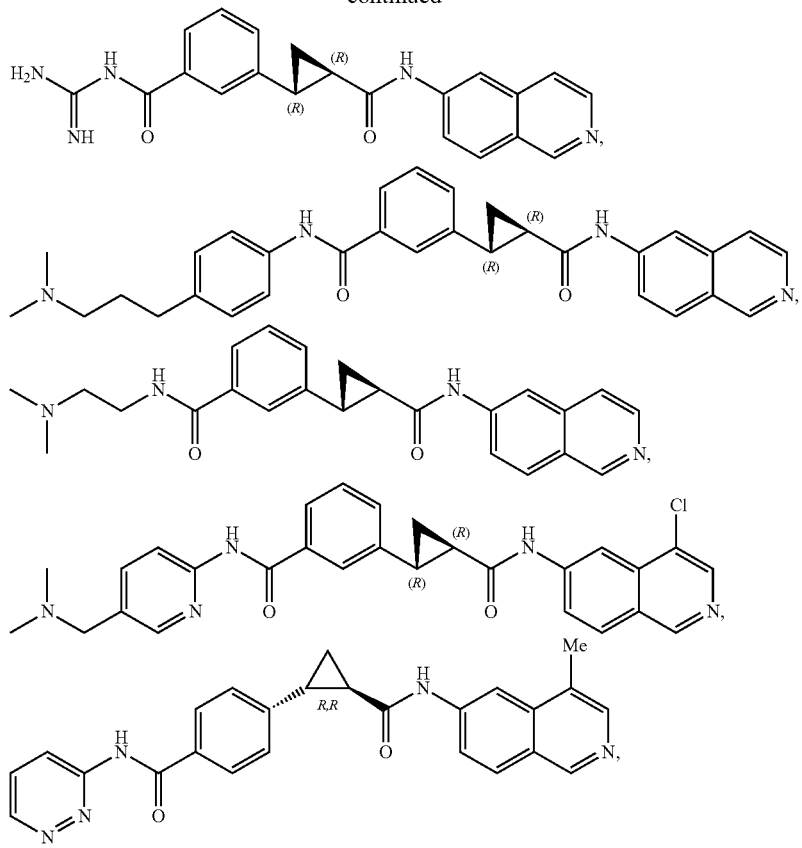

or a pharmaceutically acceptable salt thereof.

In another aspect, provided herein are compositions, comprising a compound provided herein.

In another aspect, provided herein are pharmaceutical compositions, comprising a compound provided herein and a pharmaceutically acceptable carrier.

In another aspect, provided herein are methods of treating an ocular disorder in a subject in need thereof, comprising administering to the subject a therapeutically effective amount of a compound provided herein.

In another aspect, provided herein are methods of reducing intraocular pressure in a subject in need thereof, comprising administering to the subject a therapeutically effective amount of a compound provided herein.

In another aspect, provided herein are methods of modulating kinase activity in a cell, comprising contacting the cell with a effective amount of a compound provided herein.

DETAILED DESCRIPTION

Publications and patents are referred to throughout this disclosure. All U.S. Patent Applications, U.S. Patent Application Publications, and U.S. Patents referred to herein are hereby incorporated by reference in their entirety. All percentages, ratios, and proportions used herein are percent by weight unless otherwise specified.

Listed below are definitions of various terms used in the present disclosure. These definitions apply to the terms as they are used throughout this specification and claims, unless otherwise limited in specific instances, either individually or as part of a larger group.

As used herein, the article "a" or "an" refers to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "administering" refers to administration of the compounds provided herein to a cell or a subject as needed to achieve the desired effect.

As used herein, the term "alkoxyl" alone or in combination with other terms means, unless otherwise stated, an alkyl group having the designated number of carbon atoms, as defined herein, connected to the rest of the molecule via an oxygen atom.

As used herein, the term "alkyl" alone or in combination with other terms means, unless otherwise stated, a straight or branched chain hydrocarbon having the number of carbon atoms designated (i.e., $C_{1-6}$ means one to six carbon atoms) and includes straight or branched chain substituent groups.

As used herein, the term "composition" or "pharmaceutical composition" refers to a mixture of at least one compound—useful as described herein—with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, rectal, subcutaneous, and topical administration.

As used herein, the term "contacting a cell" is used to mean contacting a cell in vitro or in vivo i.e. in a subject, such as a mammal, including humans, rabbits, cats and dogs.

As used herein, the term "controlling the disease or disorder" is used to mean changing the activity of one or more kinases to affect the disease or disorder.

As used herein, the term "eye disease" includes, but is not limited to, glaucoma, allergy, cancers of the eye, neurodegenerative diseases of the eye, such as diabetic eye disease, macular degeneration (AMD), inflammation, and dry eye.

As used herein, the term "disease or disorder associated with kinase activity" refers to a disease, condition or disorder treatable, in whole or in part, by inhibition of one or more kinases.

As used herein, the term "effective amount," "pharmaceutically effective amount" or "therapeutically effective amount" refers to a nontoxic but sufficient dosage amount of an agent (e.g., the compounds or compositions provided herein) to provide the desired biological result, which result may be reduction or alleviation, or both, of the signs, symptoms, or causes of a disease, or any other desired alteration of a biological system including influencing, reducing or inhibiting the activity of or preventing activation of a kinase (e.g., modulating kinase activity). An appropriate therapeutic amount in any individual case may be determined by one of ordinary skill in the art using routine experimentation. These terms as used herein may also refer to an amount effective at bringing about a desired in vivo effect in an animal—where in some embodiments, the animal is a human—including, but not limited to, uveitis, reduction in intraocular pressure, or dry eye.

As used herein, the term "excipient" refers to physiologically compatible additives useful in preparation of a pharmaceutical composition. Examples of pharmaceutically acceptable excipients (e.g., pharmaceutically acceptable carriers) can, for example, be found in Remington Pharmaceutical Science, 16th Ed.

As used herein, the term "haloalkyl" refers to an alkyl group independently substituted with one or more (e.g., one to six) fluorine, chlorine, bromine, or iodine atoms. In some embodiments, the alkyl group is independently substituted with one or more fluorine, chlorine, or bromine atoms. In some embodiments, the alkyl group is independently substituted with one or more (e.g., one to three) fluorine or chlorine atoms.

As used herein, the term "halo" alone or in combination with other terms means, unless otherwise stated, halogen atoms such as fluorine, chlorine, bromine, or iodine atoms (e.g., F or Cl).

As used herein, the term "haloalkoxyl" refers to an alkoxyl group independently substituted with one or more (e.g., one to six) fluorine, chlorine, bromine, or iodine atoms. In some embodiments, the alkoxyl group is independently substituted with one or more fluorine, chlorine, or bromine atoms. In some embodiments, the alkoxyl group is independently substituted with one or more (e.g., one to three) fluorine or chlorine atoms.

As used herein, the term "heteroalkyl" by itself or in combination with another term means, unless otherwise stated, a stable straight or branched chain alkyl group consisting of the stated number of carbon atoms and one, two or three heteroatoms independently selected from O, N, or S. The heteroatom(s) may be placed at any position of the heteroalkyl group, including between the rest of the heteroalkyl group and the fragment to which it is attached, as well as attached to the most distal carbon atom in the heteroalkyl group.

As used herein, the term "heteroaryl" refers to a heterocyclic ring having aromatic character. In some embodiments, heteroaryl groups have one to five carbon atoms. In some embodiments, heteroaryl groups have two to ten carbon atoms. In some embodiments, the heterocyclic ring is a polycyclic ring.

As used herein, the term "heterocyclyl" refers to a mono cyclic non-aromatic radical, wherein the atoms forming the ring (i.e., skeletal atoms) include carbon atoms and one, two, three or four heteroatoms independently selected from O, N, or S. In some embodiments, the heterocyclyl group is saturated or partially unsaturated.

As used herein, the term "subject," "patient" or "individual" refers to a human or a non-human mammal. Non-human mammals include, for example, livestock and pets, such as ovine, bovine, porcine, canine, feline, and murine mammals. In some embodiments, the patient, subject, or individual is human.

As used herein, the term "pharmaceutically acceptable" refers to a material that does not abrogate the biological activity or properties of the compound, and is relatively non-toxic, i.e. the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful as provided herein within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful as provided herein, and not injurious to the patient. As used herein, "pharmaceutically acceptable carrier" also includes any and all coatings, antibacterial and antifungal agents, and absorption delaying agents, and the like that are compatible with the activity of the compound useful as provided herein, and are physiologically acceptable to the patient. The term "pharmaceutically acceptable carrier" may further include a pharmaceutically acceptable salt of the compound useful as provided herein. Other additional ingredients that may be included in the pharmaceutical compositions are described, for example, in Remington's Pharmaceutical Sciences (Genaro, Ed., Mack Publishing Co., 1985, Easton, Pa.), which is incorporated herein by reference. The "pharmaceutically acceptable carrier" is useful for the preparation of a pharmaceutical composition that is: generally compatible with the other ingredients of the composition, not deleterious to the recipient, and neither biologically nor otherwise undesirable. "A pharmaceutically acceptable carrier" includes one or more than one carrier. Embodiments include carriers for topical, ocular, parenteral, intravenous, intraperitoneal intramuscular, sublingual, nasal or oral administration. "Pharmaceutically acceptable carrier" also includes agents for preparation of aqueous dispersions and sterile powders for injection or dispersions.

As used herein, the term "pharmaceutically acceptable salt" refers to derivatives of the compounds provided herein wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by combining the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile may be used. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "prevent" or "prevention" refers to no disorder or disease development if none had occurred, or no further disorder or disease development if there had already been development of the disorder or disease. Also considered is the ability of one to prevent some or all of the symptoms associated with the disorder or disease.

As used herein, the term "treatment" or "treating" refers to the application or administration of a therapeutic agent, i.e. a compound provided herein, to a patient, or application or administration of a therapeutic agent to an isolated tissue or cell line from a patient (e.g., for diagnosis or ex vivo applications), who has a disease, a symptom of the disease or the potential to develop the disease, with the purpose to heal, alleviate, relieve, alter, remedy, ameliorate, improve or affect the disease, the symptoms of the disease, or the potential to develop the disease. Such treatments may be specifically tailored or modified, based on knowledge obtained from the field of pharmacogenomics.

Compounds

In an aspect, provided herein are compounds of Formula (I):

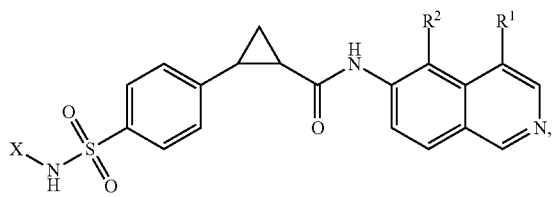
(I)

or a pharmaceutically acceptable salt thereof,
wherein
$R^1$ is H, halo, —CN, —$C_{1-6}$ alkyl, —$C_{1-6}$ alkoxyl, —$C_{1-6}$ haloalkyl, or —$C_{1-6}$ haloalkoxyl;
$R^2$ is H or halo;
X is —($C_{1-5}$ heteroaryl)—$R^3$; and
$R^3$ is halo, —$C_{2-6}$ heterocyclyl, or —$C_{1-6}$ heteroalkyl.

In another aspect, provided herein are compounds of Formula (Ia):

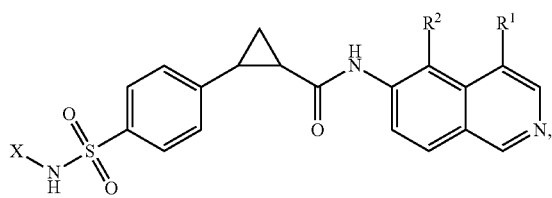
(Ia)

or a pharmaceutically acceptable salt thereof,
wherein
$R^1$ is H, halo, —CN, —$C_{1-6}$ alkyl, —$C_{1-6}$ alkoxyl, —$C_{1-6}$ haloalkyl, or —$C_{1-6}$ haloalkoxyl;
$R^2$ is H or halo;
X is —($C_{1-5}$ heteroaryl)-$(R^3)_n$;
$R^3$ is H, halo, —$C_{2-6}$ heterocyclyl, or —$C_{1-6}$ heteroalkyl; and
n is 1, 2, or 3.

In another aspect, provided herein are compounds of Formula (Ib):

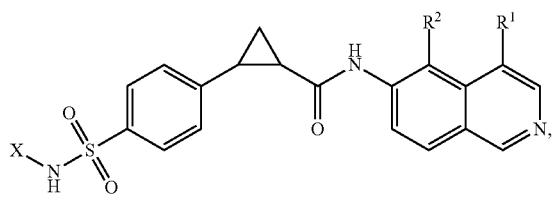
(Ib)

or a pharmaceutically acceptable salt thereof,
wherein
$R^1$ is H, halo, —CN, —$C_{1-6}$ alkyl, —$C_{1-6}$ alkoxyl, —$C_{1-6}$ haloalkyl, or —$C_{1-6}$ haloalkoxyl;
$R^2$ is H or halo;
X is —($C_{2-6}$ heterocyclyl)-$(R^3)_n$;
$R^3$ is H, halo, —$C_{2-6}$ heterocyclyl, or —$C_{1-6}$ heteroalkyl; and
n is 1, 2, or 3.

In some embodiments, the compound of Formula (I) is a compound of Formula (II):

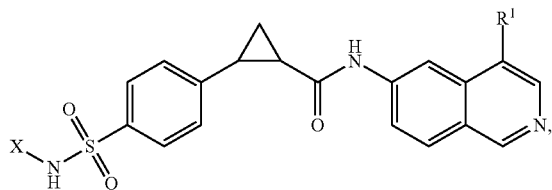
(II)

or a pharmaceutically acceptable salt thereof.

In some embodiments, the compound of Formula (I) is a compound of Formula (III):

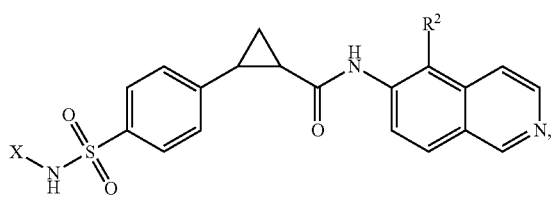

(III)

or a pharmaceutically acceptable salt thereof.

In some embodiments, $R^1$ is H, halo, —CN, —$C_{1-6}$ alkyl, —$C_{1-6}$ alkyl-OH, —$C_{1-6}$ alkoxyl, —$C_{1-6}$ haloalkyl, —$C_{1-6}$ haloalkoxyl;

In some embodiments, $R^1$ is H, halo, —CN, —$C_{1-3}$ alkyl, —$C_{1-3}$ alkoxyl, —$C_{1-3}$ haloalkyl, —$C_{1-3}$ haloalkoxyl.

In some embodiments, $R^1$ is H, Cl, —CN, —$CH_3$, —$CH_2CH_3$, —$CH(CH_3)_2$, —$CHF_2$, —$CF_3$, or —$OCF_3$.

In some embodiments, $R^1$ is Cl, —CN, —$CH_3$, —$CH_2CH_3$, —$CH(CH_3)_2$, —$CHF_2$, —$CF_3$, or —$OCF_3$.

In some embodiments, $R^1$ is H, Cl, —OH, —$CH_2OH$, —CN, —$CH_3$, —$CH_2CH_3$, —$CH(CH_3)_2$, —$CHF_2$, —$CF_3$, or —$OCF_3$.

In some embodiments, $R^1$ is Cl, —OH, —$CH_2OH$, —CN, —$CH_3$, —$CH_2CH_3$, —$CH(CH_3)_2$, —$CHF_2$, —$CF_3$, or —$OCF_3$.

In some embodiments, $R^2$ is F, Cl, Br, or I.

In some embodiments, $R^2$ is H or F.

In some embodiments, X is —($C_{3-5}$ heteroaryl)-$R^3$.

In some embodiments, X is —($C_{3-5}$ heterocyclyl)-$R^3$.

In some embodiments, X is a pyridyl, pyrrolyl, furanyl, thiophenyl, pyrazolyl, imidazolyl, pyrimidinyl, triazinyl, thiazolyl, pyrazinyl, pyridazinyl, or oxazolyl, each of which may be substituted with $R^3$.

In some embodiments, X is

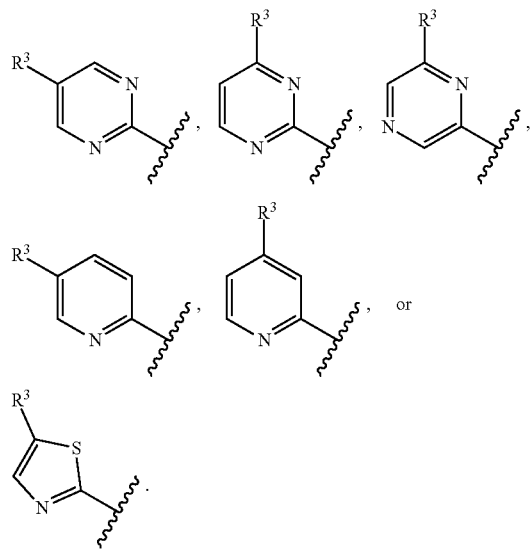

In some embodiments, X is

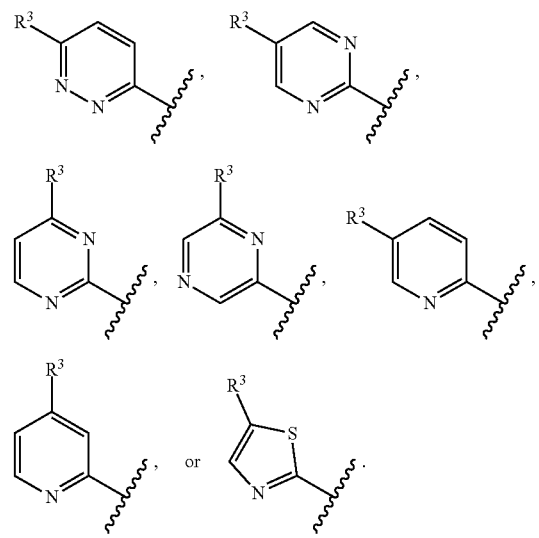

In some embodiments, X is

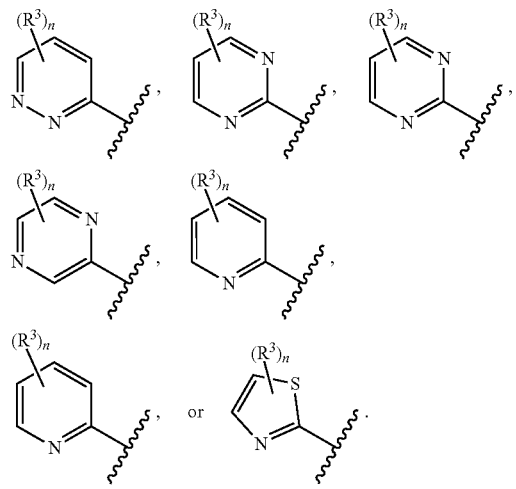

In some embodiments, X is -pyridinyl-$(R^3)_n$, -pyrimidinyl-$(R^3)_n$, -pyrazinyl-$(R^3)_n$, -pyridazinyl-$(R^3)_n$, or -thiazolyl-$(R^3)_n$.

In some embodiments, X is -tetrahydropyridinyl-$(R^3)_n$, -aziridinyl-$(R^3)_n$, -azetidinyl-$(R^3)_n$, -pyrrolidinyl-$(R^3)_n$, -piperidinyl-$(R^3)_n$, or -azepanyl-$(R^3)_n$.

In some embodiments, $R^3$ is —$C_{2-6}$ heterocyclyl or —$C_{1-6}$ heteroalkyl.

In some embodiments, $R^3$ is —$C_{3-5}$ heterocycloalkyl or —$C_{1-4}$ heteroalkyl.

In some embodiments, $R^3$ is H or F.

In some embodiments, $R^3$ is F, Cl, Br, or I.

In some embodiments, each $R^3$ is, independently, F, Cl, Br, or I.

In some embodiments, n is 1. In some embodiments, n is 2.

In some embodiments, n is 2 and each $R^3$ is, independently, F, Cl, Br, or I.

In some embodiments, $R^3$ is F,

[structures: 4-piperidinyl, 2-pyrrolidinyl, 3-pyrrolidinyl, 1,2,3,6-tetrahydropyridin-4-yl, or N,N-dimethylaminoethyl]

In some embodiments, X is

[structures: 4-piperidinyl, 2-pyrrolidinyl, 3-pyrrolidinyl, or 1,2,3,6-tetrahydropyridin-4-yl]

In some embodiments, X is

[structures with $(R^3)_n$ substitution: piperidinyl, pyrrolidinyl, pyrrolidinyl, or tetrahydropyridinyl]

In some embodiments: $R^1$ is H, Cl, —CN, —CH$_3$, —CH$_2$CH$_3$, —CH(CH$_3$)$_2$, —CHF$_2$, —CF$_3$, or —OCF$_3$;
$R^2$ is H or F;
X is

[heteroaryl structures with $R^3$: pyrimidinyl (5-), pyrimidinyl (4-), pyrimidinyl (2-), pyrazinyl, pyridinyl, pyridinyl, or thiazolyl]

and
$R^3$ is F,

[structures: 4-piperidinyl, 2-pyrrolidinyl, 3-pyrrolidinyl, 1,2,3,6-tetrahydropyridin-4-yl, or N,N-dimethylaminoethyl]

In some embodiments:
$R^1$ is Cl, —CN, —CH$_3$, —CH$_2$CH$_3$, —CH(CH$_3$)$_2$, —CHF$_2$, —CF$_3$, or —OCF$_3$;
$R^2$ is H or F;
X is

[heteroaryl structures with $R^3$: pyrimidinyl (5-), pyrimidinyl (4-), pyrimidinyl (2-), pyrazinyl, pyridinyl, pyridinyl, or thiazolyl]

and
$R^3$ is

[structures: 4-piperidinyl, 2-pyrrolidinyl, 3-pyrrolidinyl,]

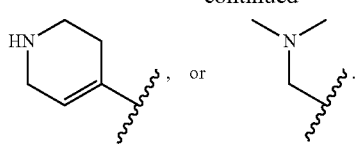, or
In some embodiments, the compound is:
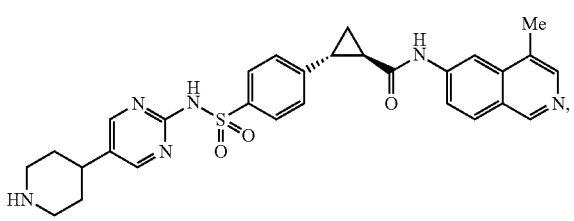
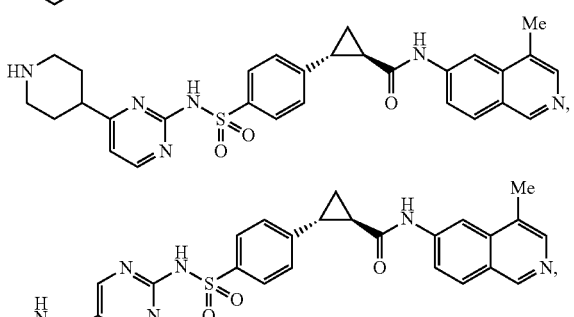
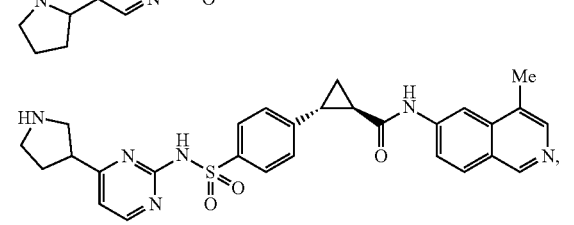
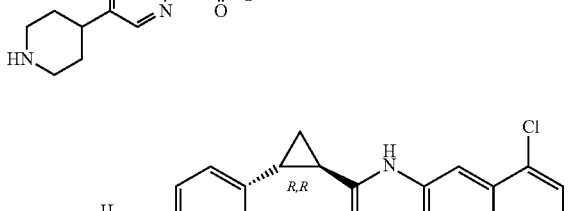
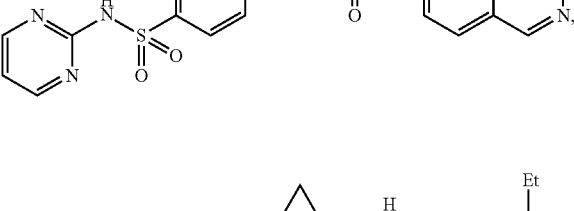
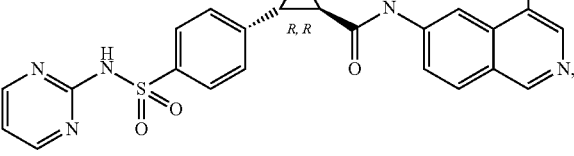
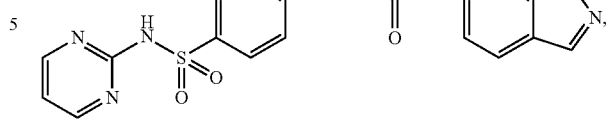
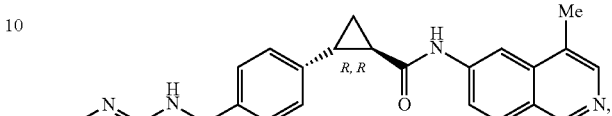
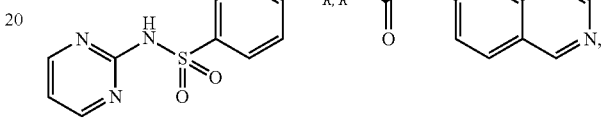
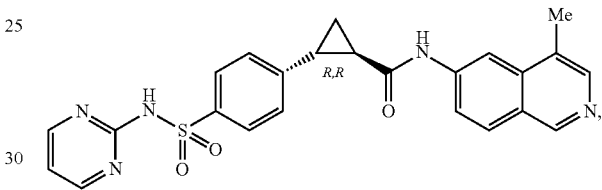
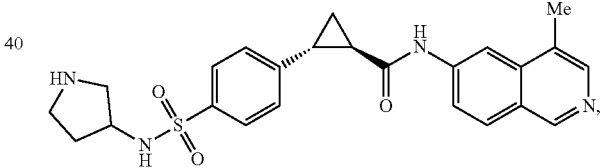
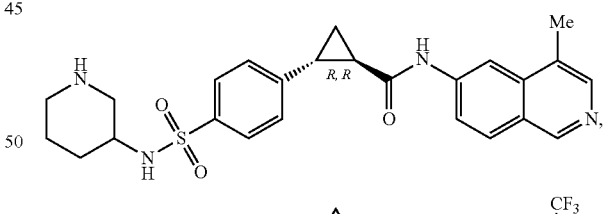
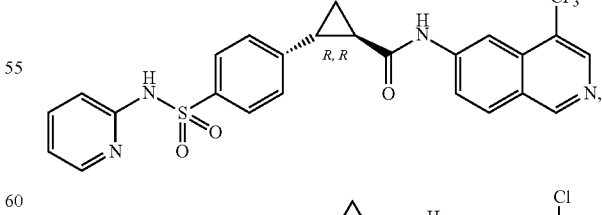

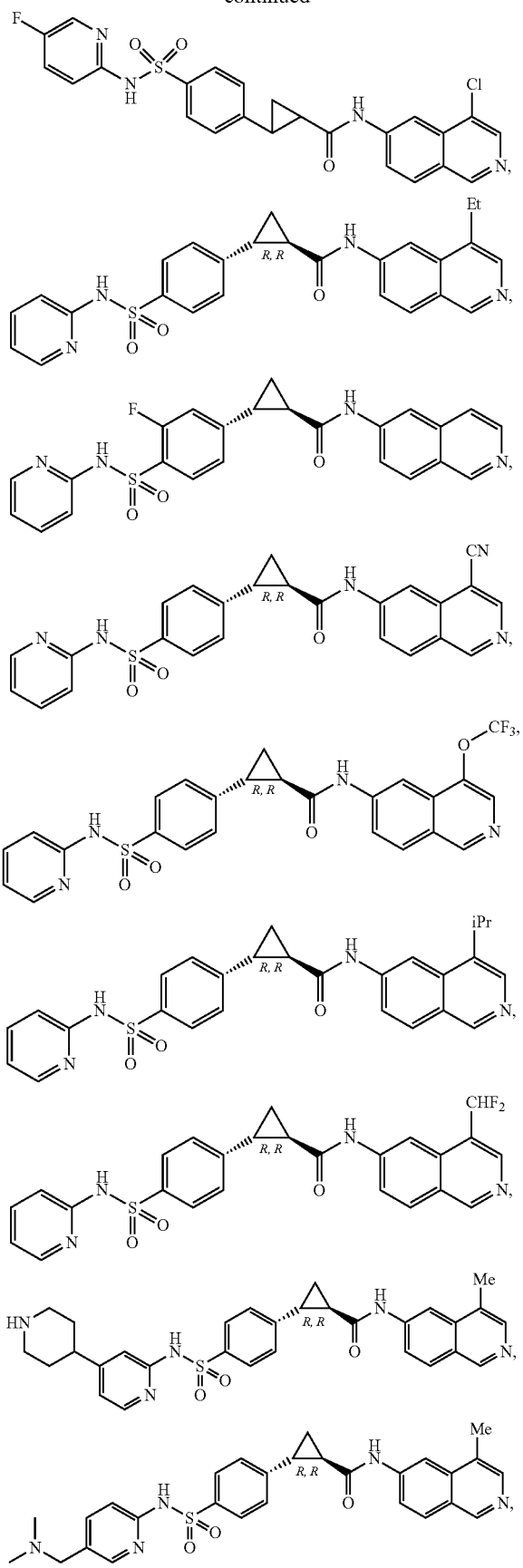
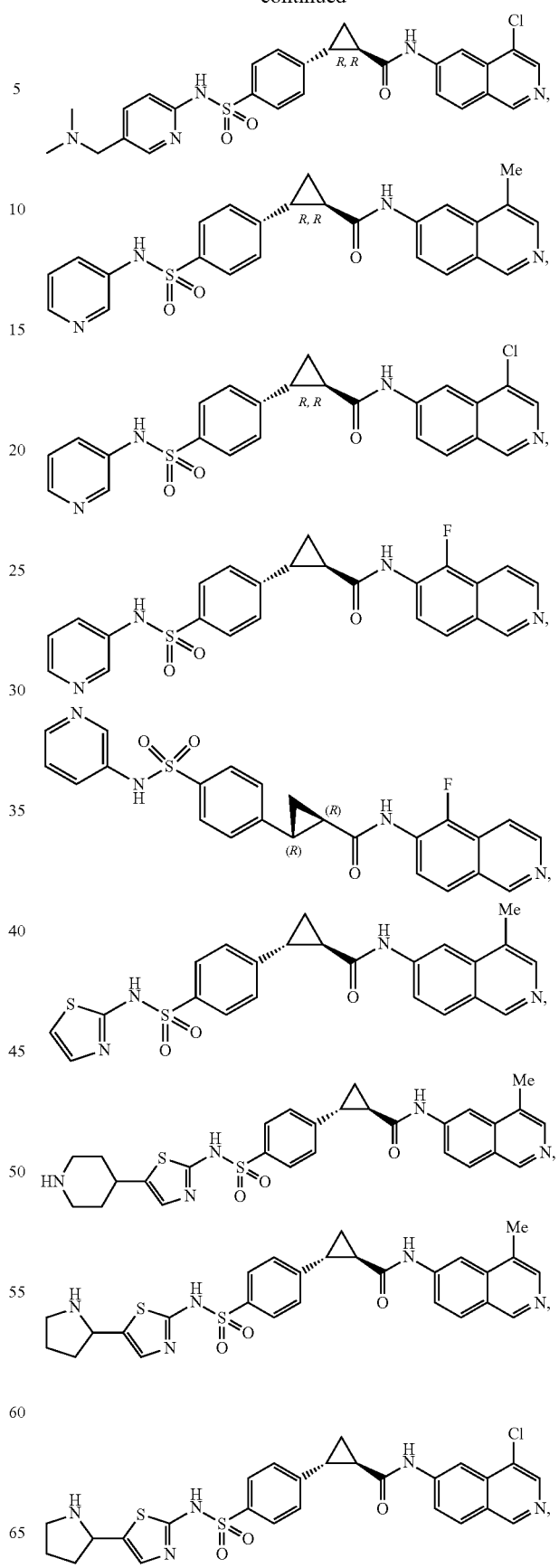

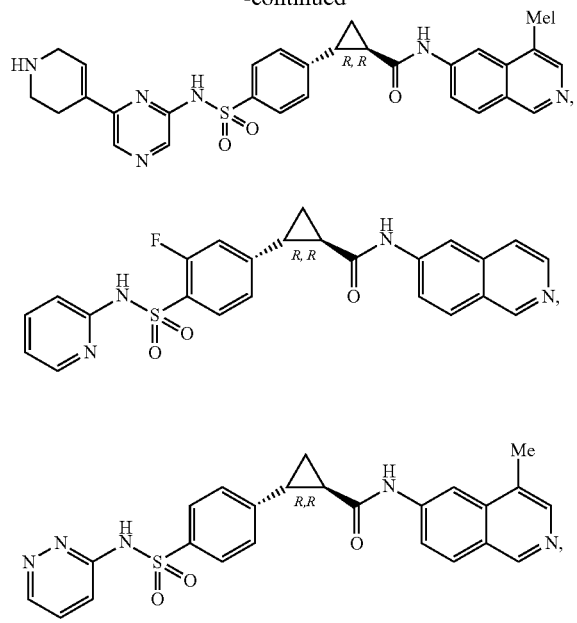
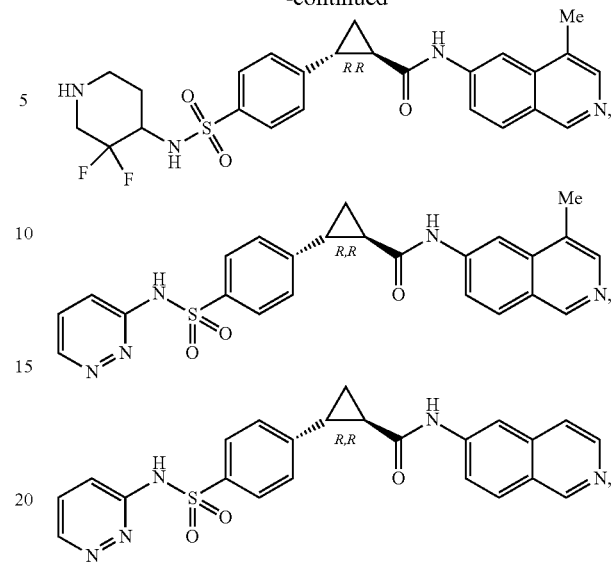
or a pharmaceutically acceptable salt thereof.
In some embodiments, the compound is:
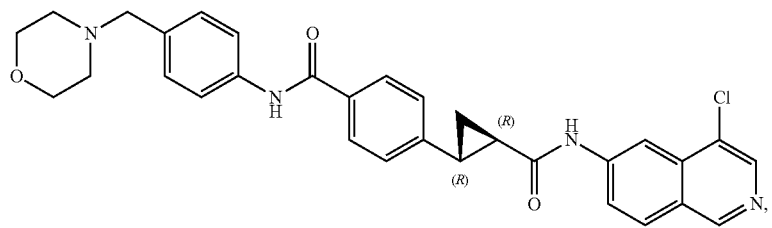
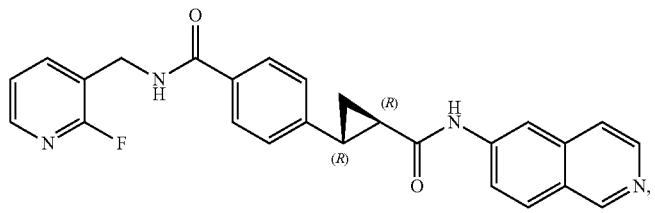
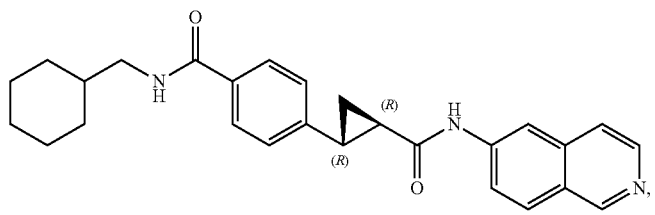
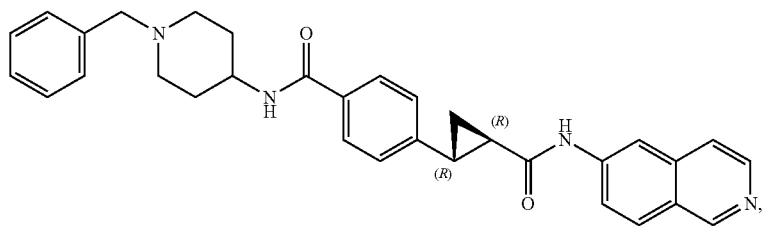

-continued
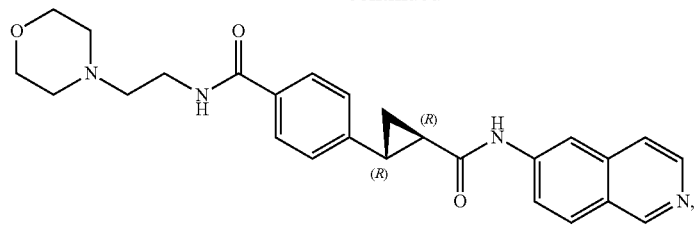
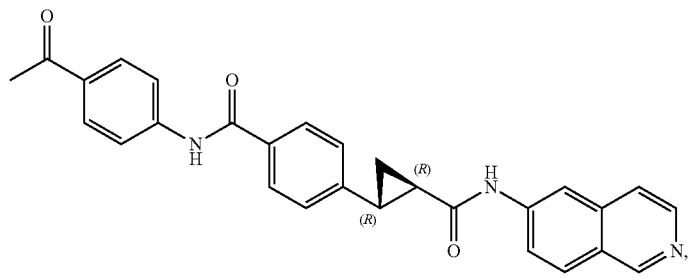
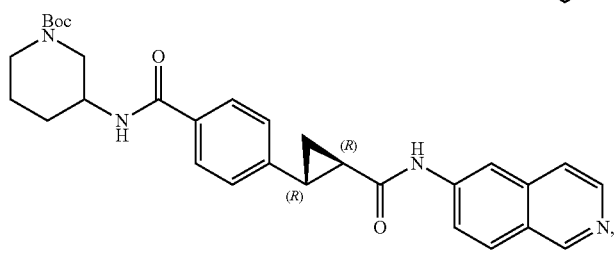
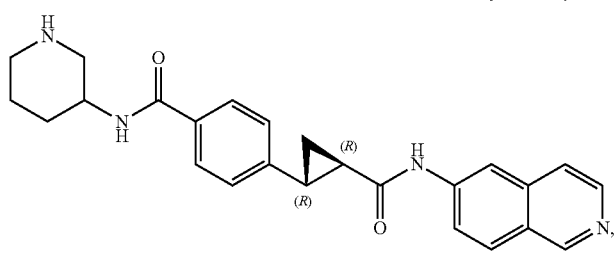
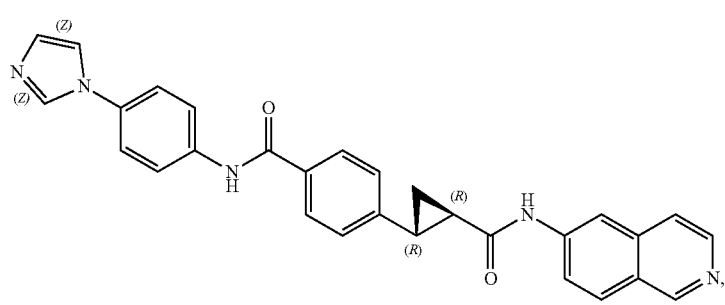
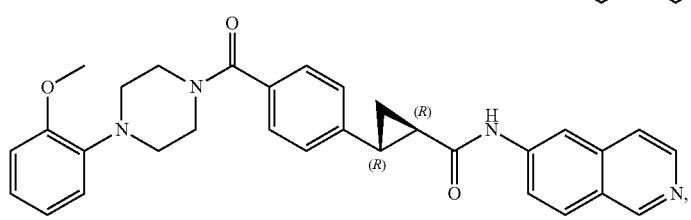
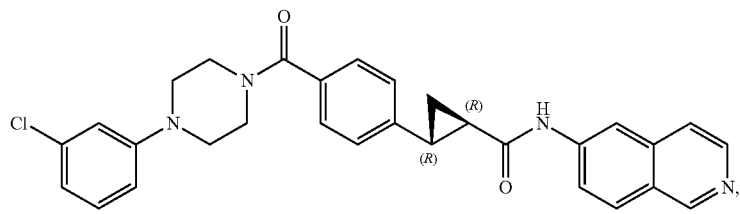

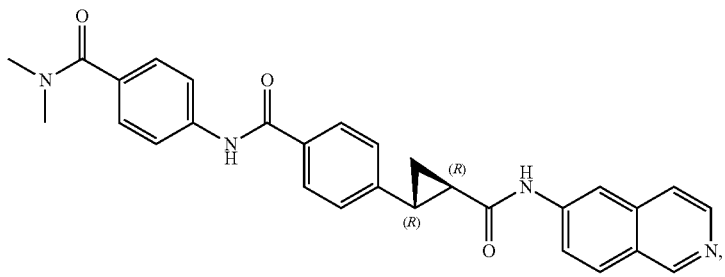
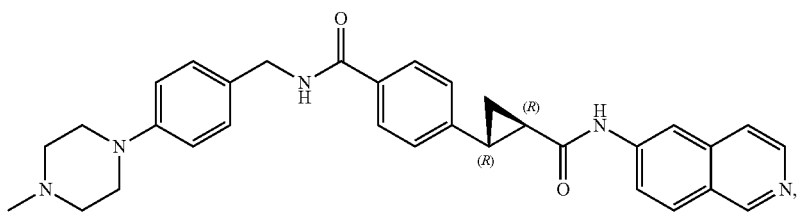
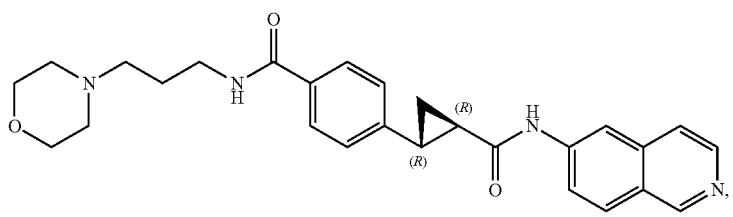
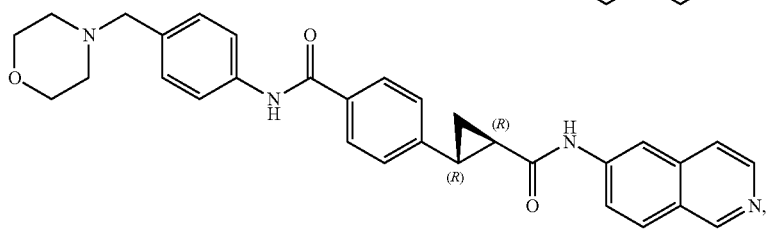
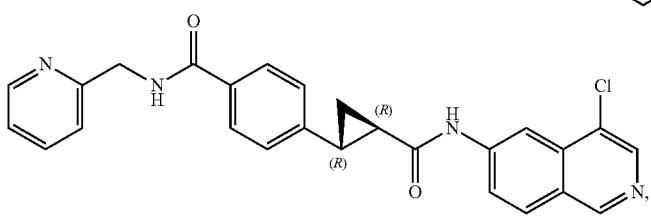
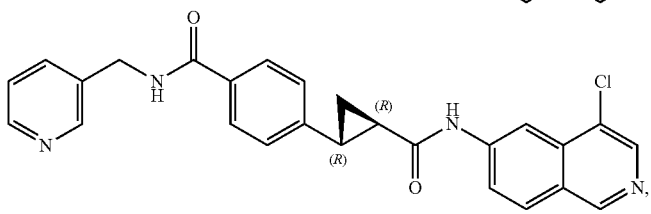
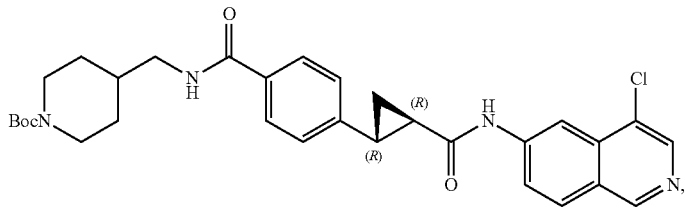

-continued
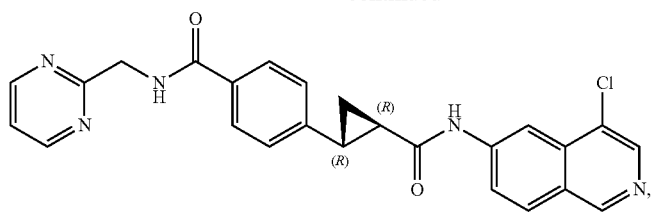
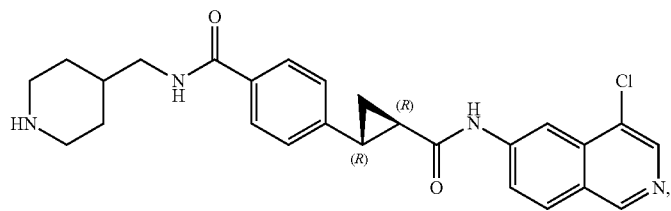
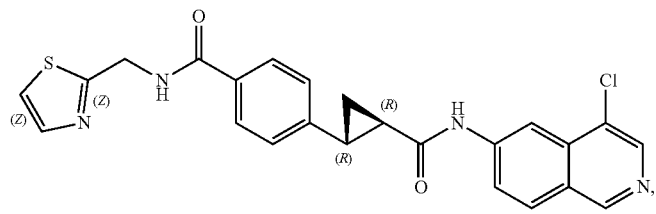
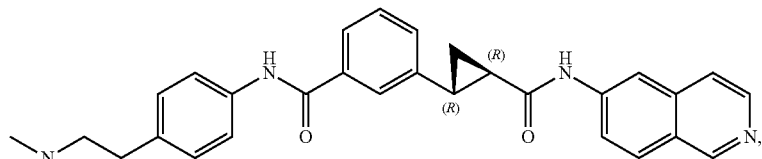
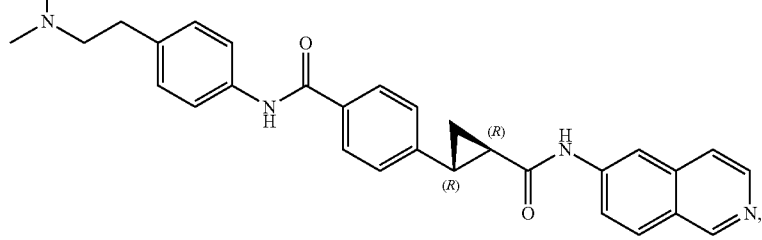
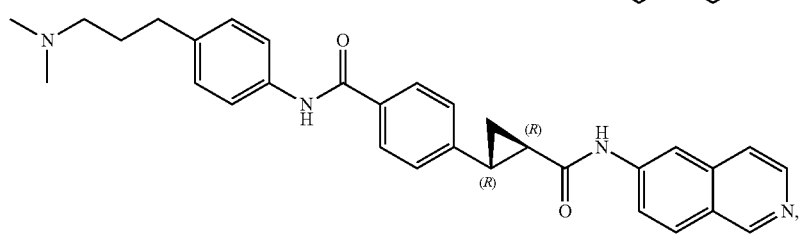
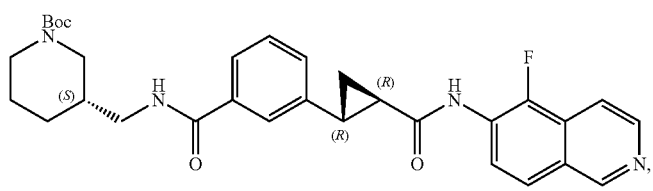
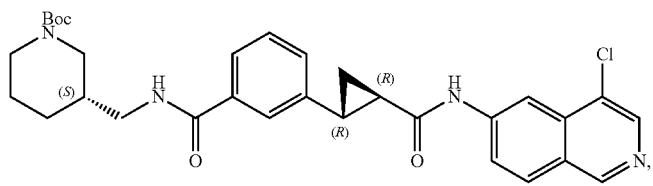

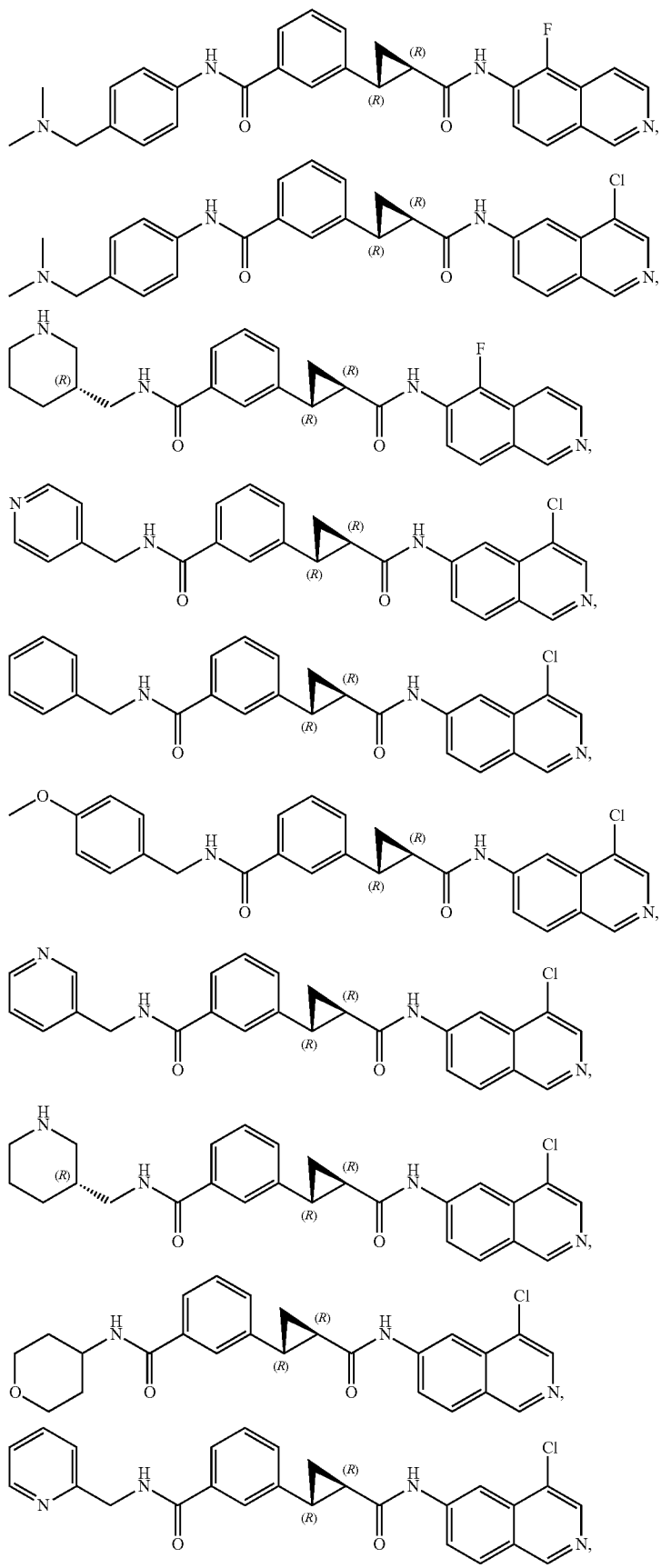

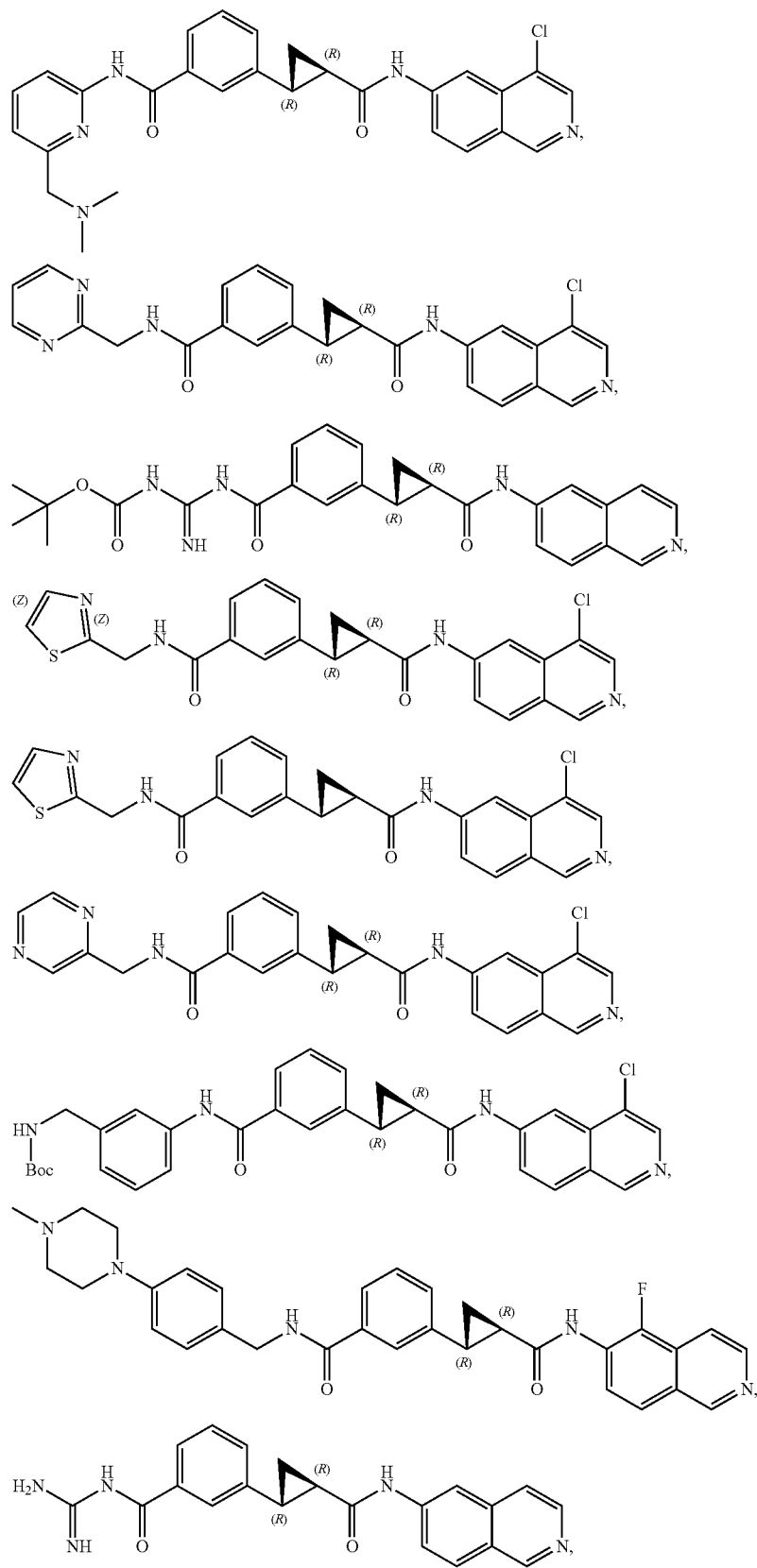

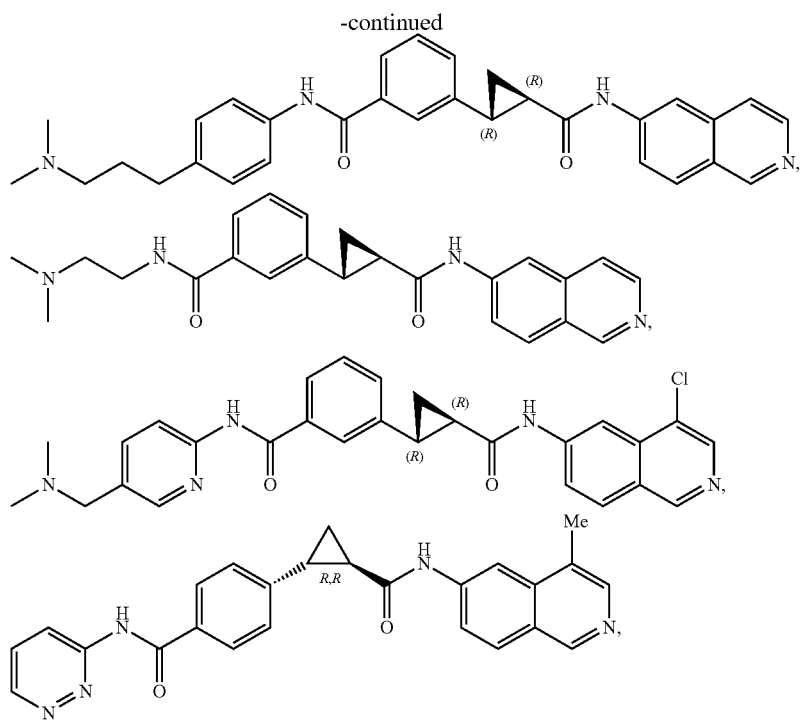

or a pharmaceutically acceptable salt thereof.

In some embodiments, the compound is a compound of Table 1 or a pharmaceutically acceptable salt thereof.

In some embodiments, the compound is a compound of Table 2 or a pharmaceutically acceptable salt thereof.

Methods

In another aspect, provided herein are methods of treating an ocular disorder in a subject in need thereof, comprising administering to the subject a therapeutically effective amount of a compound provided herein (i.e. a compound of Formula (I), Formula (Ia), Formula (Ib), Formula (II), Formula (III), Table 1, Table 2, or a pharmaceutically acceptable salt thereof).

In some embodiments, the ocular disorder is glaucoma, an inflammatory eye disease, a neurodegenerative eye disease, diabetic eye disease, wet age-related macular degeneration, or dry age-related macular degeneration.

In another aspect, provided herein are methods of reducing intraocular pressure in a subject in need thereof, comprising administering to the subject a therapeutically effective amount of a compound provided herein (i.e. a compound of Formula (I), Formula (Ia), Formula (Ib), Formula (II), Formula (III), Table 1, Table 2, or a pharmaceutically acceptable salt thereof).

In another aspect, provided herein are methods of treating a disease or disorder associated with a kinase activity in a subject in need thereof, comprising contacting the subject with a therapeutically effective amount of a compound provided herein (i.e. a compound of Formula (I), Formula (Ia), Formula (Ib), Formula (II), Formula (III), Table 1, Table 2, or a pharmaceutically acceptable salt thereof).

In some embodiments, the kinase activity is a JAK (Janus kinase) activity.

In some embodiments, the kinase activity is a ROCK (Rho-associate protein kinase) activity.

In some embodiments of these aspects, the compound is administered topically to an eye of the subject In some embodiments of these aspects, the compound is administered topically to an eyelid of the subject.

In some embodiments of these aspects, the subject is a human.

In another aspect, provided herein are methods of modulating kinase activity in a cell, comprising contacting the cell with a effective amount of a compound provided herein (i.e. a compound of Formula (I), Formula (Ia), Formula (Ib), Formula (II), Formula (III), Table 1, Table 2, or a pharmaceutically acceptable salt thereof).

In some embodiments, the cell is in a subject.

In some embodiments, the cell is in a human subject.

In another aspect, provided herein are uses of a compound provided herein (i.e. a compound of Formula (I), Formula (Ia), Formula (Ib), Formula (II), Formula (III), Table 1, Table 2, or a pharmaceutically acceptable salt thereof), a composition provided herein, or a pharmaceutical composition provided herein, in the manufacture of a medicament for the treatment of a viral infection, a cancer, or an allergic disease.

In another aspect, provided herein are compositions, comprising a compound provided herein.

In another aspect, provided herein are pharmaceutical compositions, comprising a composition provided herein and a pharmaceutically acceptable carrier.

Actual dosage levels of an active ingredient in the pharmaceutical compositions provided herein may be varied so as to obtain an amount of the active ingredient that is effective to achieve a desired therapeutic response for a particular subject, composition, or mode of administration, without being toxic to the subject.

In some embodiments, it is especially advantageous to formulate the compound in dosage unit form for ease of administration and uniformity of dosage. Dosage unit form as used herein refers to physically discrete units suited as unitary dosages for the subject to be treated; each unit containing a predetermined quantity of therapeutic compound calculated to produce the desired therapeutic effect in association with the required pharmaceutical vehicle. The dosage unit forms of the present disclosure are dictated by and directly dependent on (a) the unique characteristics of the therapeutic compound and the particular therapeutic effect to be achieved, and (b) the limitations inherent in the art of compounding/formulating such a therapeutic compound for the treatment of the diseases referred to herein in a subject in need thereof.

In one embodiment, the compounds or compositions provided herein are formulated using one or more pharmaceutically acceptable excipients or carriers. In one embodiment, the pharmaceutical compositions provided herein comprise a therapeutically effective amount of a compound provided herein and a pharmaceutically acceptable carrier.

In one embodiment, the present disclosure provides packaged pharmaceutical compositions comprising a container holding at least one therapeutically effective amount of a compound provided herein, and instructions for using the compound to treat one or more symptoms of a disease referred to herein in a subject in need thereof.

Routes of administration of any of the compositions provided herein include oral, nasal, rectal, intravaginal, parenteral, buccal, sublingual, topical, or ocular. The compounds for use as provided herein may be formulated for administration by any suitable route, such as for ocular, oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, drops, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for ocular or intravesical administration and the like. It should be understood that the formulations and compositions that would be useful as provided herein are not limited to the particular formulations and compositions that are described herein.

In another aspect, provided herein are dosage forms suitable for administration to a subject in need thereof, comprising a compound provided herein (i.e. a compound of Formula (I), Formula (Ia), Formula (Ib), Formula (II), Formula (III), Table 1, Table 2, or a pharmaceutically acceptable salt thereof).

In another aspect, provided herein are kits, comprising a composition including a compound provided herein (i.e. a compound of Formula (I), Formula (Ia), Formula (Ib), Formula (II), Formula (III), Table 1, Table 2, or a pharmaceutically acceptable salt thereof) and instructions for use thereof. In some embodiments, the kit further includes one or more of a syringe, a vial, or a dosage form.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size or volume, and experimental reagents, such as solvents, catalysts, pressures, atmospheric conditions, e.g., nitrogen atmosphere, and reducing or oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or present disclosure as set forth herein.

EXAMPLES

Compounds provided herein may be prepared as described in U.S. patent application Ser. No. 15/941,993.

Example 1: ROCK and JAK Assays

ROCK Kinase Inhibition Assays.

All compounds were initially prepared as 10 mM stocks in anhydrous dimethylsulfoxide (DMSO). A 20 µl aliquot of the 10 mM solutions was transferred to individual wells in column 1 of a 96-well polypropylene microtiter plate (Corning #3363) and diluted with DMSO to give a final compound concentration of 4 mM. Test compounds were then serially diluted 1:5 in DMSO for an 11-point concentration response and further diluted in the assay buffer bringing all compound concentrations to a final range of 100 µM to 10 pM in 2.5% DMSO. The assay was performed in white 96-well, flat-bottom, half-area, non-binding assay plate (Corning #3642) in assay buffer consisting of 20 mM HEPES (pH 7.5), 10 mM $MgCl_2*6H_2O$, 100 µM sodium orthovanadate, 0.05% CHAPS and 0.1% bovine serum albumin. A 10 µL aliquot of compound from each well of the intermediate dilution plate and 20 µL of a 2× substrate/enzyme solution containing acceptor substrate (800 nM RSK2 peptide KRRRLSSLRA (SEQ ID NO: 1)), ROCK2 enzyme (10 nM), or ROCK1 enzyme, and 1,4-Dithiothreitol (DTT, 2 µM) were added to all wells. The reaction was initiated by the addition of 10 µL of 4× stock solution ATP (2 ||M). Reactions were thoroughly mixed manually, covered and allowed to incubate at room temperature for 75 min. Protein kinase activity was quantitated using Promega's KINASE-GLO™ luminescent Kinase Assay Kit according to the manufacturer's directions. ATP concentrations remaining in Test wells following the termination of the enzymatic reaction were compared against control wells containing equivalent amounts of DMSO containing no inhibitor (CTRL). ATP concentrations in both Test wells and CTRL wells were normalized against background (BKG) ATP concentrations in wells containing concentrations of inhibitor that completely inhibited the protein kinase under investigation (i.e. a concentration that prevented any consumption of ATP over the course of the incubation). Percent of Control (POC) values were determined for each concentration of compound tested according to the equation:

$$POC=((\text{Test well value}-BKG)/(CTRL-BKG))*100$$

$IC_{50}$ values were calculated using the following 4-parameter logistic curve-fitting algorithm:

$$f(x)=(A+((B-A)/(1+((x/C)^D))))$$

$IC_{50}$ values were converted to $K_i$ values using the Cheng-Prusoff Equation: $K_i=IC_{50}/(1+([ATP]/Km\ ATP))$.

JAK Kinase Assays.

Compounds were prepared in the exact same manner as described in the ROCK Kinase Assay with the exception to the substrate and enzyme. The JAK 2× substrate/enzyme solution consisted of acceptor substrate (800 nM Abl peptide EAIYAAPFAKKK (SEQ ID NO: 2)), JAK2 or JAK3 enzyme (10 nM) and DTT (2 µM). All other steps and solutions remain identical to the ROCK Kinase Assay above. Results are shown below in Table 1 and Table 2.

Example 2: PTM-HTM Assay

Porcine Trabecular Meshwork cells (PTM) were isolated from freshly obtained enucleated porcine eyes. Immortalized Human Trabecular Meshwork cells (TM-1) were obtained through a kind gift from Donna Peters in the Department of Ophthalmology and Visual Sciences at the University of Wisconsin. Cells were plated onto fibronectin coated glass-bottom 96-well plates and allowed to attach overnight. Media was removed and replaced with test compound in media with 1% fetal bovine serum and incubated for various times. After incubation, cells were formaldehyde fixed, triton solubilized, and stained. PTM cells were stained with Alexa Fluor®488 phalloidin (F-actin) and Hoechst 33342 (nuclei). TM-1 cells were stained with anti-paxillin followed by Alexa Fluor®488 goat-anti-mouse IgG (focal adhesions) and Hoechst 33342 (nuclei). All staining reagents were obtained through Invitrogen. Images were collected on an INCell 2200 imager with a 20× objective. The actin fiber length and total area of focal adhesions were analyzed using custom algorithms developed in the INCell Developer Toolbox, v1.9.3. Data collected were converted to percent of control (untreated cells). Curves were fit to data in GraphPad Prizm using sigmoidal dose-response and constraining top and bottom to 100% and 0%, respectively. Results are shown below in Table 1 and Table 2.

Example 3: Pharmaceutical Compositions for Lowering Intraocular Pressure

Topical pharmaceutical compositions of the compounds provided herein for lowering intraocular pressure are prepared by conventional methods. A compound according to this disclosure is used as the free base or a pharmaceutically acceptable salt thereof. When the composition is topically administered to the eyes once daily, the above composition decreases intraocular pressure in a subject suffering from glaucoma Example 4: Pharmacological Activity for Glaucoma Assay Pharmacological activity for glaucoma can also be demonstrated using assays designed to test the ability of the subject compounds to decrease intraocular pressure. Examples of such assays are described in the following reference, incorporated herein by reference: C. Liljebris, G. Selen, B. Resul, J. Sternschantz, and U. Hacksell, "Derivatives of 17-phenyl-18, 19, 20-trinorprostaglandin $F_{2\alpha}$ Isopropyl Ester: Potential Anti-glaucoma Agents", *Journal of Medicinal Chemistry* 1995, 38 (2): 289-304.

TABLE 1

| Compound | Structure | $IC_{50}$ (nM) |
|---|---|---|
| 1 | 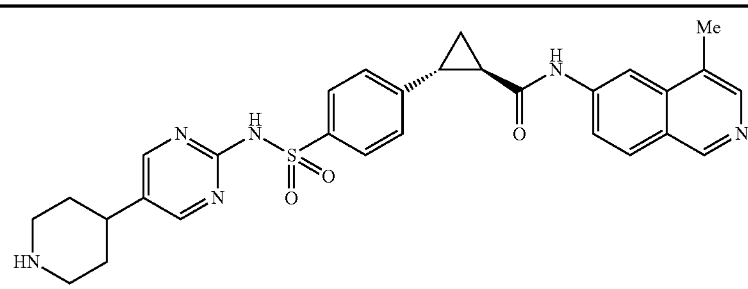 | 19 nM JAK2<br>148 nM JAK3<br>16 nM ROCK1<br>4.9 nM ROCK2<br>1130 nM $IKK_\beta$ |
| 2 | 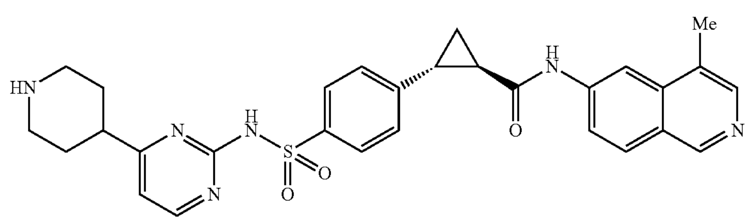 [SMILES: Cc1cncc2ccc(NC(=O)[C@@H]3C[C@H]3c3ccc(S(=O)(=O)Nc4nccc(C5CCNCC5)n4)cc3)cc12] | |
| 3 | 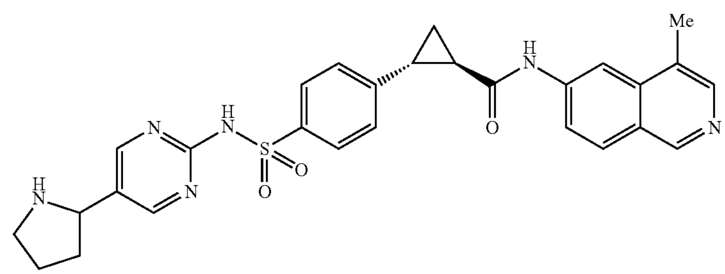 [SMILES: Cc1cncc2ccc(NC(=O)[C@@H]3C[C@H]3c3ccc(S(=O)(=O)Nc4ncc(C5CCCN5)cn4)cc3)cc12] | |

TABLE 1-continued

| Compound | Structure | IC$_{50}$ (nM) |
|---|---|---|
| 4 | 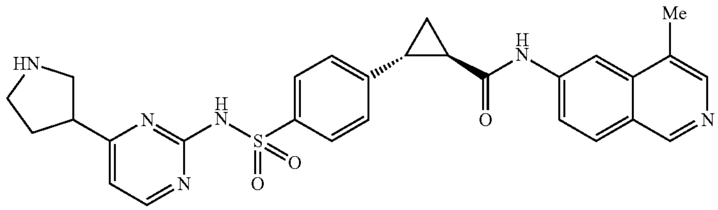 [SMILES: Cc1cncc2ccc(NC(=O)[C@@H]3C[C@H]3c3ccc(S(=O)(=O)Nc4nccc(C5CCNC5)n4)cc3)cc12] | |
| 5 | 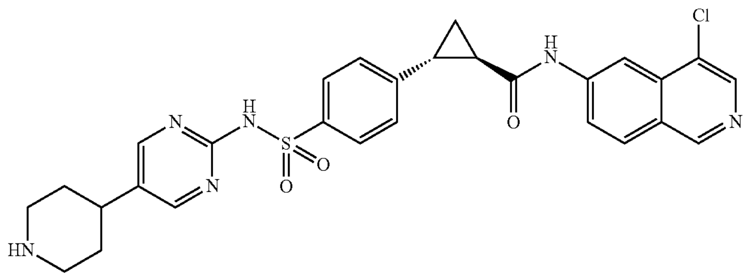 | |
| 6 | 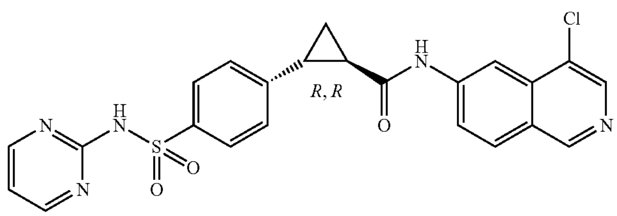 | 0.70 nM JAK2<br>1.5 nM JAK3<br>128 nM ROCK1<br>68 nM ROCK2<br>4.1 nM IKK$_\beta$<br>PTM: 2100 nM<br>2.0 nM JAK1<br>0.25 nM TYK2 |
| 7 | 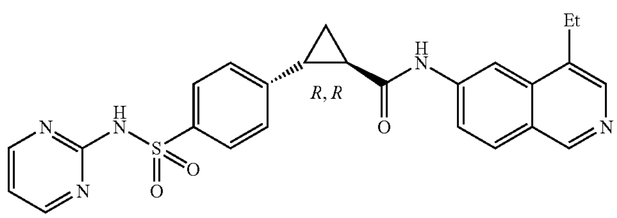 | 1.0 nM JAK2<br>5.8 nM JAK3<br>1087 nM ROCK1<br>880 nM ROCK2<br>3.6 nM IKK$_\beta$ |
| 8 | 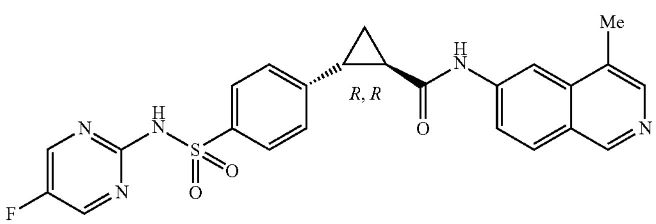 | 0.65 nM JAK2<br>3.9 nM JAK3<br>7.3 nM IKK$_\beta$<br>121 nM ROCK1<br>93 nM ROCK2 |
| 9 | 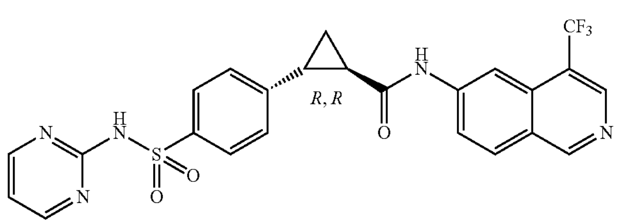 | 1.0 nM JAK2<br>8.2 nM JAK3<br>1570 nM ROCK1<br>1165 nM ROCK2<br>14 nM IKK$_\beta$ |
| 10 | 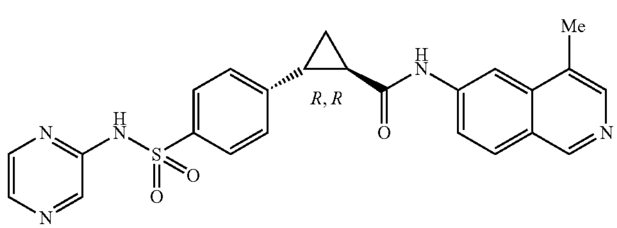 | 3.0 nM JAK2<br>14.0 nM JAK3<br>220 nM ROCK1<br>74 nM ROCK2<br>105 nM IKK$_\beta$<br>>1000 nM Stat5<br>15 nM JAK1<br>34 nM TYK2 |

TABLE 1-continued

| Compound | Structure | IC$_{50}$ (nM) |
|---|---|---|
| 11 | 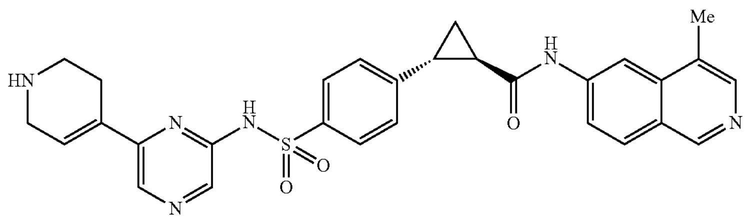 [SMILES: Cc1cncc2ccc(NC(=O)[C@@H]3C[C@H]3c3ccc(S(=O)(=O)Nc4cncc(C5=CCNCC5)n4)cc3)cc12] | 10.8 nM JAK2<br>135 nM JAK3<br>153 nM ROCK1<br>15 nM ROCK2<br>765 nM IKK$_\beta$ |
| 12 | 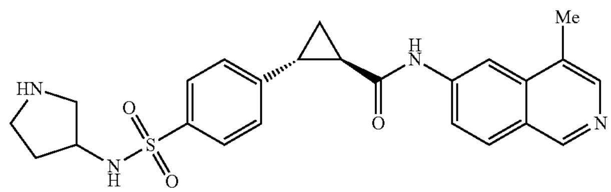 [SMILES: Cc1cncc2ccc(NC(=O)[C@@H]3C[C@H]3c3ccc(S(=O)(=O)NC4CCNC4)cc3)cc12] | 17 nM JAK2<br>175 nM JAK3<br>759 nM IKK$_\beta$<br>21 nM ROCK1<br>21 nM ROCK2 |
| 13 | 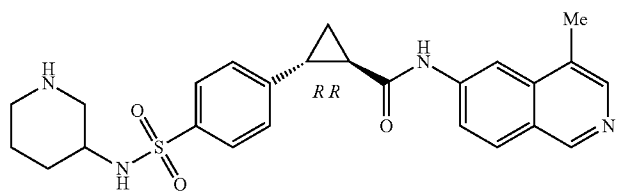 | 21 nM JAK2<br>179 nM JAK3<br>825 nM IKK$_\beta$<br>18 nM ROCK1<br>15 nM ROCK2 |
| 14 | 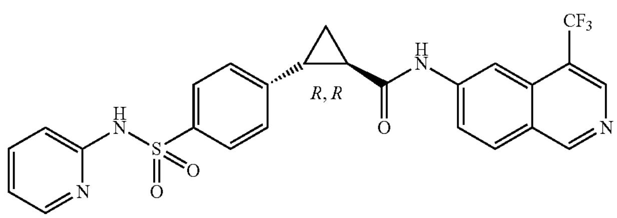 | 0.90 nM JAK2<br>9.0 nM JAK3<br>122 nM ROCK1<br>108 nM ROCK2<br>16 nM IKK$_\beta$<br>200 nM Stat5<br>1080 nM PTM |
| 15 | 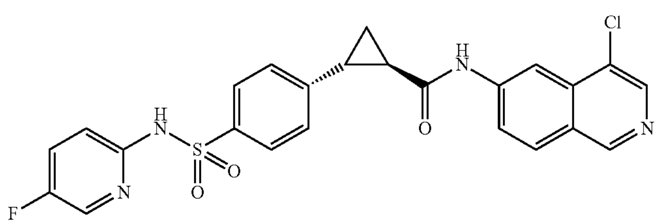 | 2.0 nM JAK2<br>4.8 nM JAK3<br>156 nM ROCK1<br>56 nM ROCK2<br>88 nM IKK$_\beta$ |
| 16 | 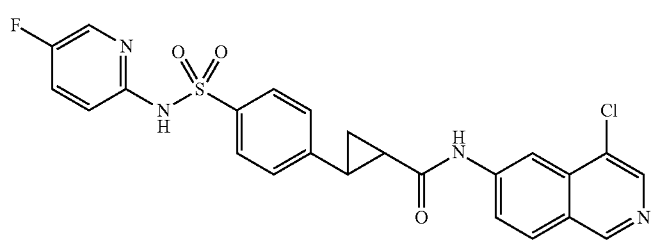 [SMILES: O=C(Nc1ccc2cncc(Cl)c2c1)C1CC1c1ccc(S(=O)(=O)Nc2ccc(F)cn2)cc1] | |
| 16a | racemic | 2.0 nM JAK2<br>4.8 nM JAK3<br>56 nM ROCK2<br>156 nM ROCK1<br>88 nM IKK$_\beta$<br>0.8 nM JAK1<br>7.0 nM TYK2 |

TABLE 1-continued

| Compound | Structure | IC$_{50}$ (nM) |
|---|---|---|
| 16b | chiral non-racemic | 1.0 nM JAK2<br>2.9 nM JAK3<br>25 nM ROCK2<br>74 nM ROCK1<br>70 nM IKK$_\beta$<br>0.44 nM JAK1<br>12 nM TYK2 |
| 17 | R,R | 0.8 nM JAK2<br>4.2 nM JAK3<br>44 nM ROCK1<br>45 nM ROCK2 |
| 18 | 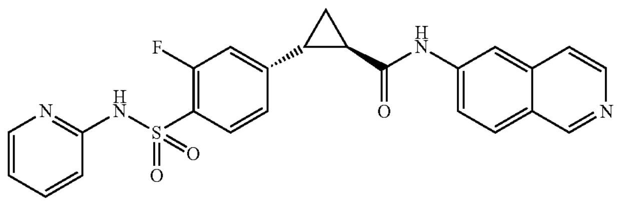 | 2.5 nM JAK2<br>19.5 nM JAK3<br>6.4 nM ROCK1<br>4.0 nM ROCK2<br>17.5 nM IKK$_\beta$ |
| 19 | R,R | 4975 nM JAK2<br>6750 nM JAK3<br>7400 nM ROCK1<br>4750 nM ROCK2<br>nM IKK$_\beta$ |
| 20 | R,R | 0.9 nM JAK2<br>2.4 nM JAK3<br>30 nM ROCK1<br>20 nM ROCK2<br>6.9 nM IKK$_\beta$ |
| 21 | R,R | |
| 22 | R,R | |

TABLE 1-continued

| Compound | Structure | IC$_{50}$ (nM) |
|---|---|---|
| 23 | 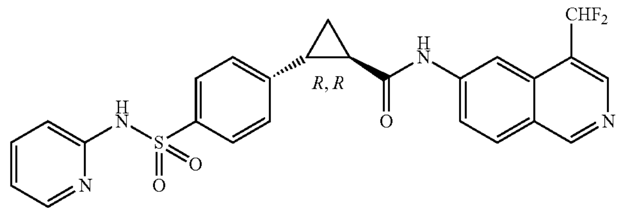 | |
| 24 | 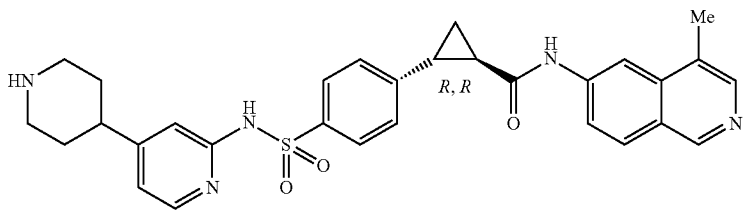 | |
| 25 | 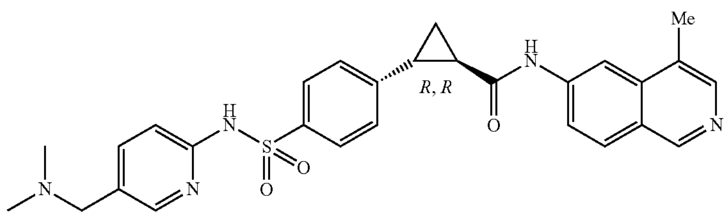 | |
| 26 | 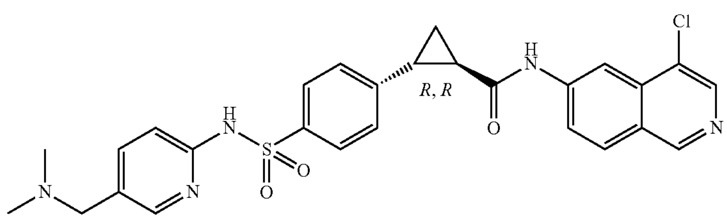 | |
| 27 | 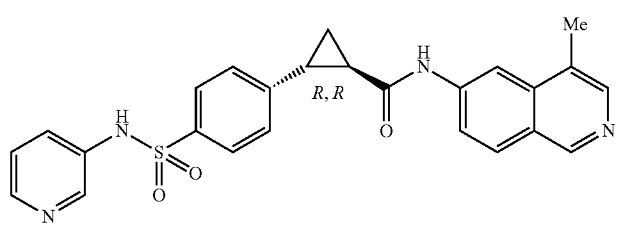 | 1.15 nM JAK2<br>19 nM JAK3<br>125 nM ROCK1<br>44 nM ROCK2<br>159 nM IKK$_\beta$<br>41 nM Stat5<br>120 nM JAK1<br>98 nM TYK2 |
| 28 | 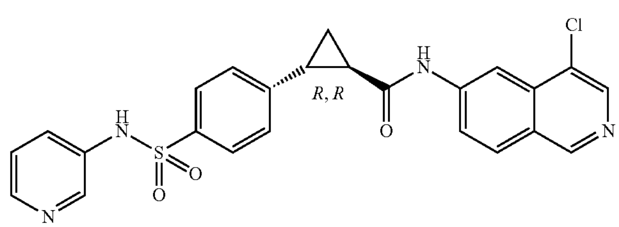 | 170 nM JAK1<br>1.4 nM JAK2<br>18 nM JAK3<br>160 nM ROCK1<br>67 nM ROCK2<br>381 nM IKK$_\beta$<br>57 nM Stat5<br>210 nM TYK2 |
| 29 | 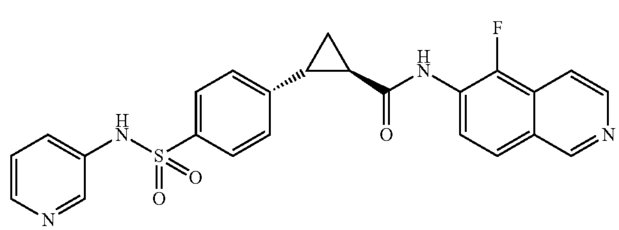 | 43 nM ROCK1<br>13.8 nM ROCK2<br>170 nM JAK2<br>350 nM JAK3<br>>5000 nM IKK$_\beta$ |

TABLE 1-continued
| Compound | Structure | IC$_{50}$ (nM) |
|---|---|---|
| 30 | 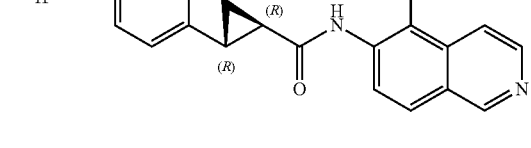 | |
| 31 | 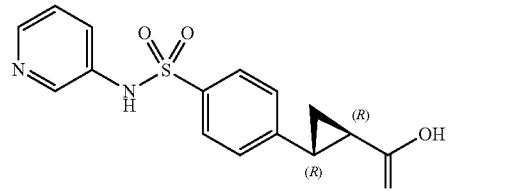 | |
| 32 | 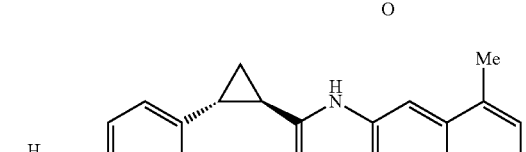 | 0.35 nM JAK2<br>3.4 nM JAK3<br>5.0 nM IKK$_\beta$<br>20.0 nM ROCK1<br>12.3 nM ROCK2 |
| 33 | 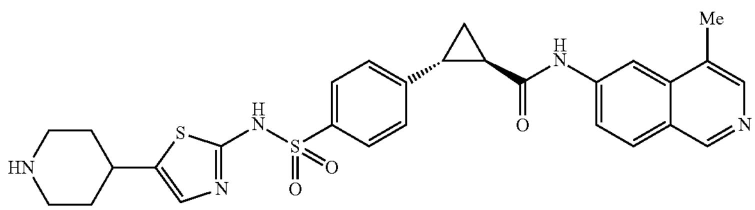 [SMILES: Cc1cncc2ccc(NC(=O)[C@@H]3C[C@H]3c3ccc(S(=O)(=O)Nc4ncc(C5CCNCC5)s4)cc3)cc12] | |
| 34 | 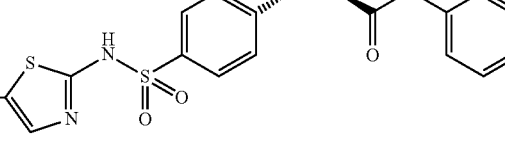 | |
| 35 | 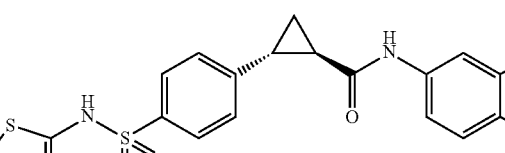 | |
| 37 | 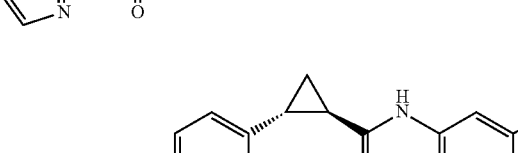 | |

TABLE 1-continued

| Compound | Structure | IC$_{50}$ (nM) |
|---|---|---|
| 38 | 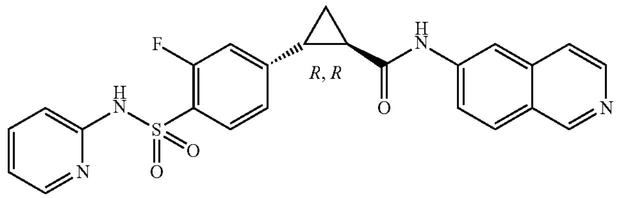 | |
| 39 | 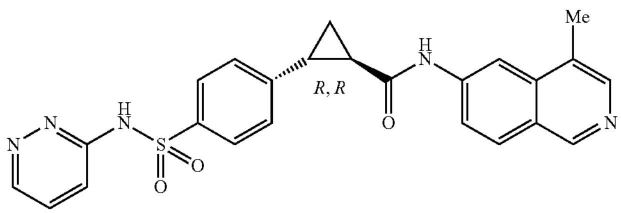 | |
| 40 | (HCl) | |
| 41 | 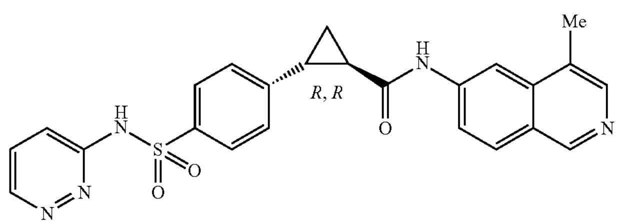 | |
| 42 | 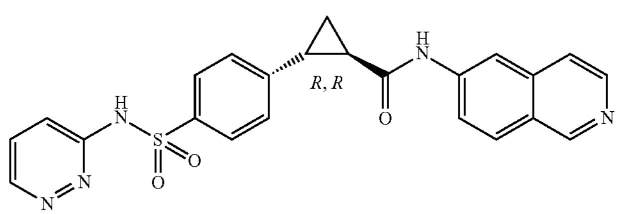 | |

TABLE 2

| Compound | Structure | IC$_{50}$ or Ki (nM) |
|---|---|---|
| 36 | 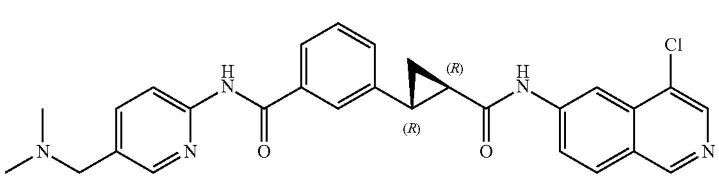 | 1.0 nM Ki ROCK2<br>6 nM Ki JAK2<br>211 nM Ki JAK3<br>1192 nM Ki IKK$_\beta$<br>12 nM IC$_{50}$ PTM |

TABLE 2-continued

| Compound | Structure | IC$_{50}$ or Ki (nM) |
|---|---|---|
| 43 | 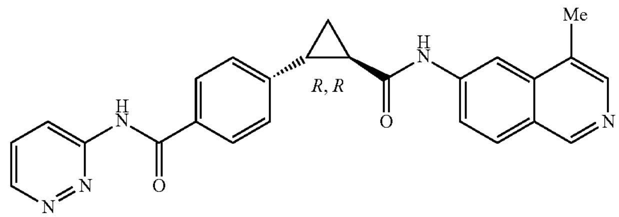 | |
| 44 | 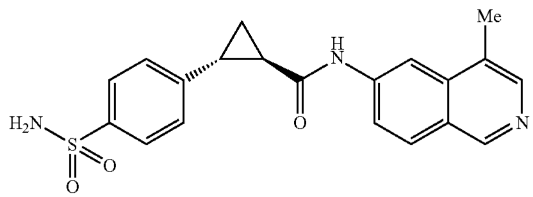 | |
| 45 | 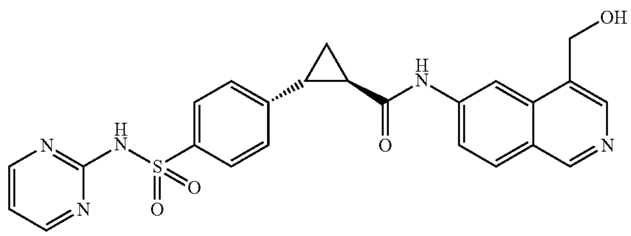 | |
| 46 | 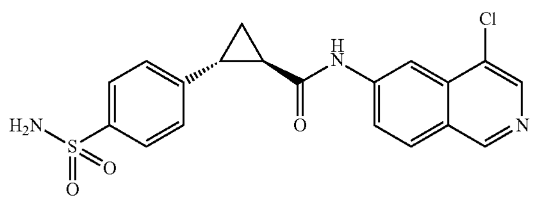 [SMILES: NS(=O)(=O)c1ccc([C@@H]2C[C@H]2C(=O)Nc2ccc3cncc(Cl)c3c2)cc1] | |
| 47 | 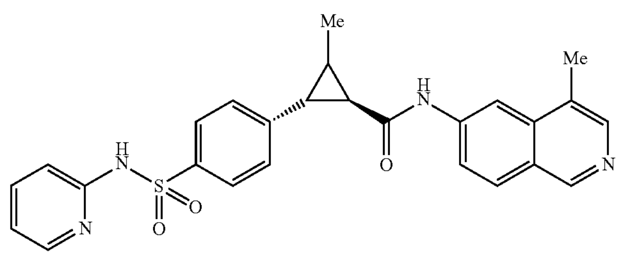 | |
| 48 | 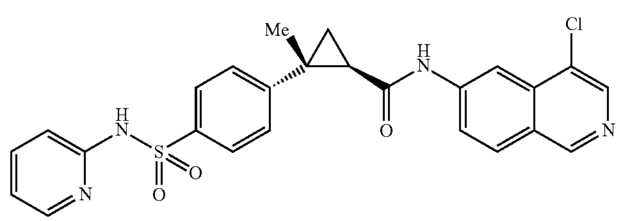 | |
| 49 | | 2.0 nM JAK2<br>16 nM JAK3<br>3.2 nM IKK$_\beta$<br>181 nM ROCK2<br>207 nM ROCK1<br>48 nM JAK1<br>91 nM TYK2 | chiral

TABLE 2-continued

| Compound | Structure | IC$_{50}$ or Ki (nM) |
| --- | --- | --- |
| 50 | racemic | |
| 51 | racemic | 3.0 nM JAK2<br>15 nM JAK3<br>132 nM IKK$_\beta$<br>8 nM ROCK2<br>9 nM ROCK1<br>11 nM JAK1<br>47 nM TYK2 |
| 52 | Chiral non-racemic | 1.0 nM JAK2<br>4.4 nM JAK3<br>3.0 nM ROCK2<br>6.0 nM ROCK1<br>10 nM IKK$_\beta$<br>330 nM PKA<br>4.0 nM JAK1<br>15 nM TYK2 |
| 53 | Chiral Non-racemic | 0.95 nM JAK2<br>3.4 nM JAK3<br>3.2 nM IKK$_\beta$<br>35 nM ROCK2<br>67 nM ROCK1<br>6.5 nM JAK1<br>12.7 nM TYK2 |
| 54 | 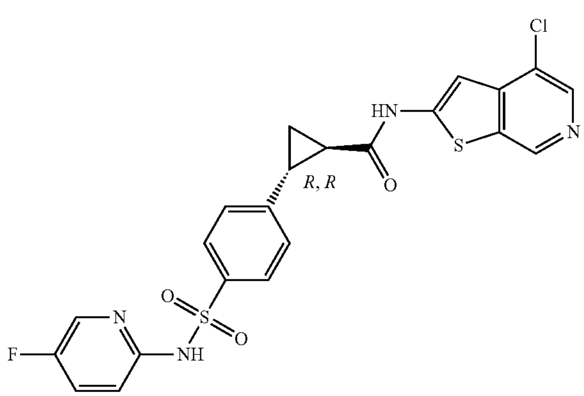 [SMILES: O=C(Nc1cc2c(Cl)cncc2s1)[C@@H]1C[C@H]1c1ccc(S(=O)(=O)Nc2ccc(F)cn2)cc1] | 12 nM JAK2<br>205 nM JAK3<br>3750 nM IKK$_\beta$<br>11 nM ROCK2<br>25 nM ROCK1<br>17 nM JAK1<br>167 nM TYK2 |

TABLE 2-continued

| Compound | Structure | IC$_{50}$ or Ki (nM) |
| --- | --- | --- |
| 55 | chiral non-racemic | 1.0 nM JAK2<br>4.8 nM JAK3<br>38 nM IKK$_\beta$<br>343 nM ROCK2<br>748 nM ROCK1<br>0.9 nM JAK1<br>9.0 nM TYK2 |
| 56 | racemic | 2.0 nM JAK2<br>12 nM JAK3<br>260 nM ROCK2<br>360 nM ROCK1<br>54 nM IKK$_\beta$<br>15 nM JAK1<br>16 nM TYK2 |
| 57 | achiral | 370 nM ROCK2<br>700 nM ROCK1<br>14 nM JAK2<br>112 nM JAK3<br>1240 nM IKK$_\beta$ |
| 58 | achiral | 385 nM ROCK2<br>915 nM ROCK1<br>225 nM JAK2<br>1430 nM JAK3<br>1630 nM IKK$_\beta$ |
| 59 | chiral non-racemic | 1.0 nM JAK2<br>13 nM JAK3<br>3.6 nM IKK$_\beta$<br>107 nM ROCK2<br>170 nM ROCK1<br>28 nM JAK1<br>30 nM TYK2 |
| 60 | 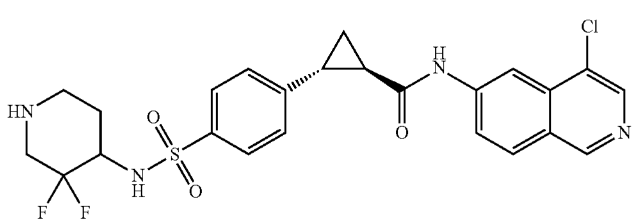 [SMILES: O=C(Nc1ccc2cncc(Cl)c2c1)[C@@H]1C[C@H]1c1ccc(S(=O)(=O)NC2CCNCC2(F)F)cc1] | 11.8 nM JAK2<br>13 nM JAK3<br>1585 nM IKK$_\beta$<br>5.9 nM ROCK2<br>15.5 nM ROCK1<br>48 nM JAK1<br>110 nM TYK2 |

TABLE 2-continued

| Compound | Structure | IC$_{50}$ or Ki (nM) |
| --- | --- | --- |
| 61 | 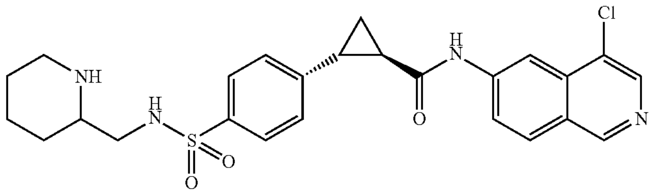 | 108 nM JAK2<br>785 nM JAK3<br>5813 nM IKK$_\beta$<br>225 nM ROCK2<br>275 nM ROCK1<br>465 nM JAK1<br>1065 nM TYK2 |
| 62 | racemic | 2.0 nM JAK2<br>7.7 nM JAK3<br>6.4 nM IKK$_\beta$<br>116 nM ROCK2<br>190 nM ROCK1<br>16 nM JAK1<br>15 nM TYK2 |
| 63 | racemic | 72 nM JAK2<br>203 nM JAK3<br>320 nM IKK$_\beta$<br>37 nM ROCK2<br>116 nM ROCK1<br>3300 nM JAK1<br>4200 nM TYK2 |
| 64 | 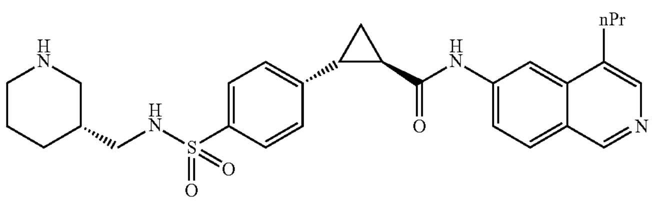 | 250 nM JAK2<br>2476 nM JAK3<br>336 nM IKK$_\beta$<br>99 nM ROCK2<br>127 nM ROCK1<br>1028 nM JAK1<br>2183 nM TYK2 |
| 65 | 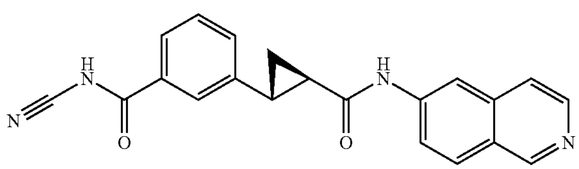 [SMILES: N#CNC(=O)c1cccc([C@@H]2C[C@H]2C(=O)Nc2ccc3cnccc3c2)c1] | |
| 66 | racemic | 72 nM JAK2<br>1505 nM JAK3<br>319 nM IKK$_\beta$<br>39 nM ROCK2<br>116 nM ROCK1<br>3344 nM JAK1<br>4278 nM TYK2 |
| 67 | chiral non-racemic | 2.0 nM JAK2<br>10.5 nM JAK3<br>11.5 nM IKK$_\beta$<br>1550 nM ROCK2<br>3400 nM ROCK1<br>10.5 nM JAK1<br>19.5 nM TYK2 |

TABLE 2-continued

| Compound | Structure | IC$_{50}$ or Ki (nM) |
|---|---|---|
| 68 | 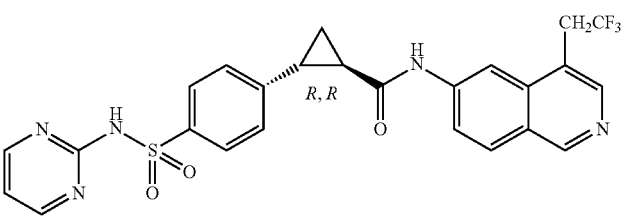 chiral non-racemic | 3.0 nM JAK2<br>48 nM JAK3<br>9.1 nM IKK$_\beta$<br>3800 nM ROCK2<br>6500 nM ROCK1<br>115 nM JAK1<br>145 nM TYK2 |
| 69 | 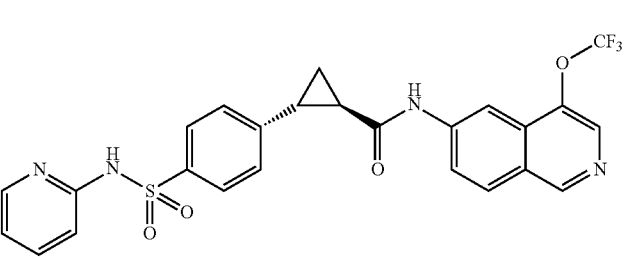 racemic | 3.0 nM JAK2<br>25 nM JAK3<br>370 nM ROCK2<br>470 nM ROCK1<br>16 nM IKK$_\beta$<br>53 nM JAK1<br>73 nM TYK2 |
| 70 | 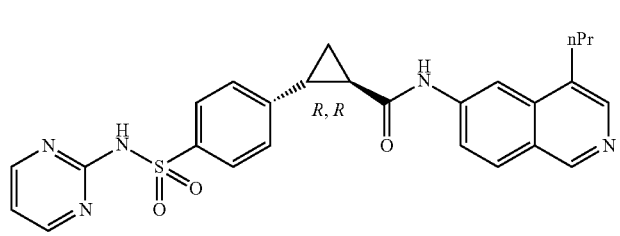 chiral non-racemic | 1.0 nM JAK2<br>14.5 nM JAK3<br>3.1 nM IKK$_\beta$<br>1830 nM ROCK2<br>3650 nM ROCK1<br>24.4 nM JAK1<br>39 nM TYK2 |
| 71 | 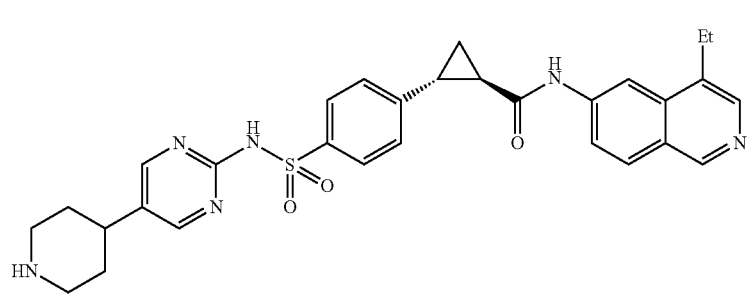 chiral, non-racemic | 20.2 nM JAK2<br>200 nM JAK3<br>600 nM IKK$_\beta$<br>235 nM ROCK2<br>520 nM ROCK1<br>120 nM JAK1<br>630 nM TYK2 |
| 72 | 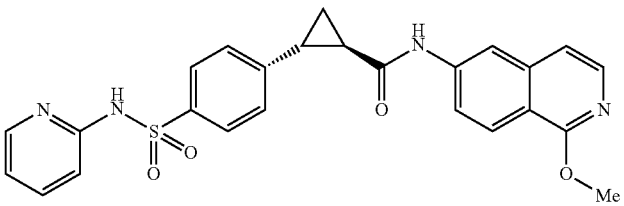 racemic | 7000 nM JAK2<br>>50 k nM JAK3<br>>50 k nM ROCK2<br>>50 k nM RCK1<br>14,000 nM IKK$_\beta$<br>>50 k nM JAK1<br>>50 k nM TYK2 |

TABLE 2-continued

| Compound | Structure | IC$_{50}$ or Ki (nM) |
|---|---|---|
| 73 | 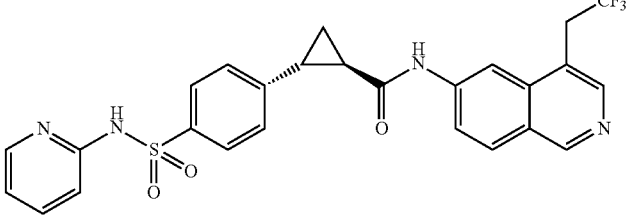 racemic | 5.9 nM JAK2<br>97 nM JAK3<br>1060 nM ROCK2<br>1216 nM RCK1<br>11.8 nM IKK$_\beta$<br>195 nM JAK1<br>230 nM TYK2 |
| 74 | 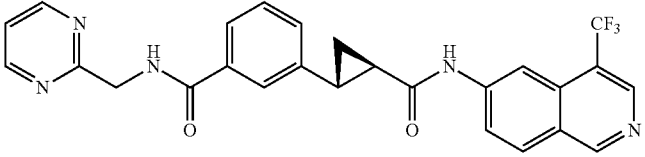 [SMILES: O=C(NCc1ncccn1)c1cccc([C@@H]2C[C@H]2C(=O)Nc2ccc3cncc(C(F)(F)F)c3c2)c1] | 7.4 nM JAK2<br>15 nM JAK3<br>25 nM ROCK2<br>18 nM ROCK1<br>250 nM JAK1<br>230 nM TYK2 |
| 75 | 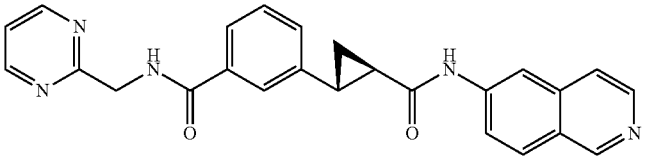 [SMILES: O=C(NCc1ncccn1)c1cccc([C@@H]2C[C@H]2C(=O)Nc2ccc3cnccc3c2)c1] | |
| 76 | 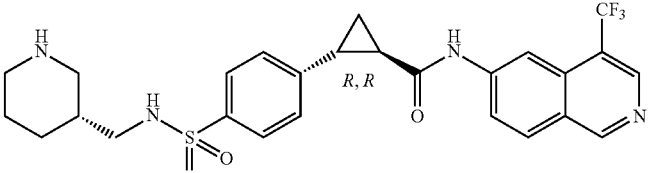 Chiral nonracemic, HCl salt | 30 nM JAK2<br>725 nM JAK3<br>13 nM ROCK2<br>15 nM ROCK1<br>3600 nM IKK$_\beta$<br>140 nM JAK1<br>165 nM TYK2 |
| 77 | 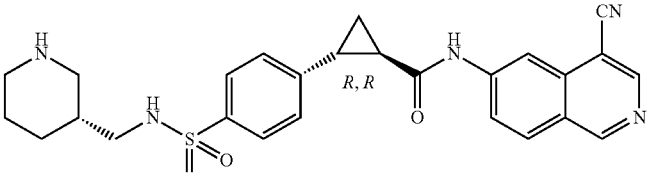 Chiral nonracemic, HCl salt | 15 nM JAK2<br>380 nM JAK3<br>2350 nM IKK$_\beta$<br>8.0 nM ROCK2<br>14 nM ROCK1<br>59 nM JAK1<br>250 nM TYK2 |
| 78 | 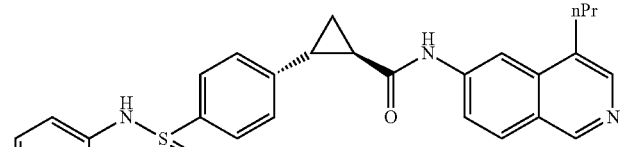 racemic<br>Cynthia synthesis | 2.0 nM JAK2<br>32 nM JAK3<br>4.0 nM IKK$_\beta$<br>220 nM ROCK2<br>310 nM ROCK1<br>34 nM JAK1<br>55 nM TYK2 |

TABLE 2-continued

| Compound | Structure | IC$_{50}$ or Ki (nM) |
|---|---|---|
| 79 | chiral, non-racemic | 7.0 nM JAK2<br>98 nM JAK3<br>31 nM ROCK2<br>68 nM ROCK1<br>208 nM IKK$_\beta$<br>110 nM JAK1<br>290 nM TYK2 |
| 80 | chiral, non-racemic (batch one) | 1.5 nM JAK2<br>15 nM JAK3<br>23 nM ROCK2<br>35 nM ROCK1<br>509 nM IKK$_\beta$<br>8.5 nM JAK1<br>40 nM TYK2 |
| 81 | Chiral nonracemic, HCl salt | 4.4 nM JAK2<br>61 nM JAK3<br>500 nM IKK$_\beta$<br>3.0 nM ROCK2<br>5.1 nM ROCK1<br>18 nM JAK1<br>51 nM TYK2 |
| 82 | Chiral nonracemic, HCl salt | 13 nM JAK2<br>200 nM JAK3<br>507 nM IKK$_\beta$<br>4.5 nM ROCK2<br>9.0 nM ROCK1<br>100 nM JAK1<br>189 nM TYK2 |
| 83 | chiral, non-racemic | 9.4 nM JAK2<br>38 nM JAK3<br>280 nM IKK$_\beta$<br>3.5 nM ROCK2<br>6.4 nM ROCK1<br>42 nM JAK1<br>112 nM TYK2 |
| 84 | chiral, non-racemic | 3.4 nM JAK2<br>17 nM JAK3<br>235 nM IKK$_\beta$<br>17.3 nM ROCK2<br>46 nM ROCK1<br>PTM: xx nM<br>16 nM JAK1<br>28 nM TYK2 |

TABLE 2-continued

| Compound | Structure | IC$_{50}$ or Ki (nM) |
|---|---|---|
| 85 | chiral, non-racemic | 1.0 nM JAK2<br>5.8 nM JAK3<br>875 nM ROCK2<br>1200 nM ROCK1<br>3.6 nM IKK$_\beta$<br>7.3 nM JAK1<br>12 nM TYK2 |
| 86 | 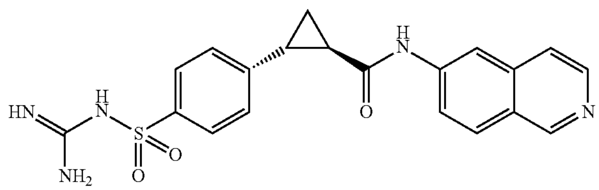 | 2.0 nM ROCK2<br>3.4 nM ROCK1<br>4.5 nM JAK2<br>23 nM JAK3<br>34.5 nM IKK$_\beta$<br>19 nM JAK1<br>79 nM TYK2 |
| 87 | non-racemic | 0.8 nM JAK2<br>4.3 nM JAK3<br>2.7 nM IKK$_\beta$<br>45 nM ROCK2<br>44 nM ROCK1<br>12 nM JAK1<br>19 nM TYK2 |
| 88 | Chiral, non-racemic | 10.8 nM JAK2<br>135 nM JAK3<br>57 nM ROCK2<br>153 nM ROCK1<br>765 nM IKK$_\beta$<br>68 nM JAK1<br>143 nM TYK2 |
| 89 | chiral, non-racemic | 19 nM JAK2<br>148 nM JAK3<br>4.9 nM ROCK2<br>16 nM ROCK1<br>1130 nM IKK$_\beta$<br>95 nM JAK1<br>227 nM TYK2 |
| 90 | ortho substituted | 4975 nM JAK2<br>6750 nM JAK3<br>4750 nM ROCK2<br>7400 nM ROCK1 |

TABLE 2-continued

| Compound | Structure | IC$_{50}$ or Ki (nM) |
|---|---|---|
| 91 | 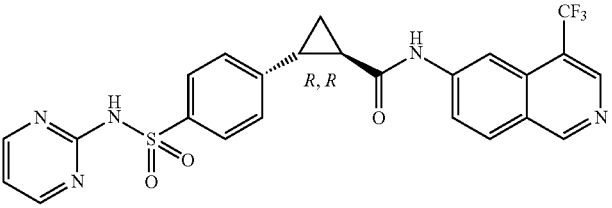<br>chiral | 1.0 nM JAK2<br>8.2 nM JAK3<br>1165 nM ROCK2<br>1570 nM ROCK1<br>14 nM IKK$_\beta$<br>5.0 nM JAK1<br>3.9 nM TYK2 |
| 92 | 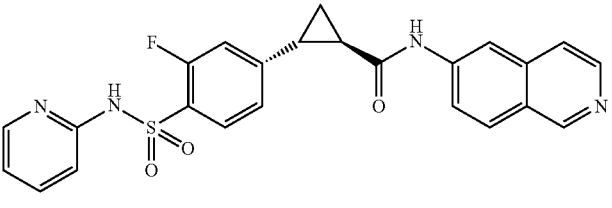 | 2.5 nM JAK2<br>19.5 nM JAK3<br>4.0 nM ROCK2<br>6.4 nM ROCK1<br>17.5 nM IKK$_\beta$<br>23 nM JAK1<br>74 nM TYK2 |
| 93 | 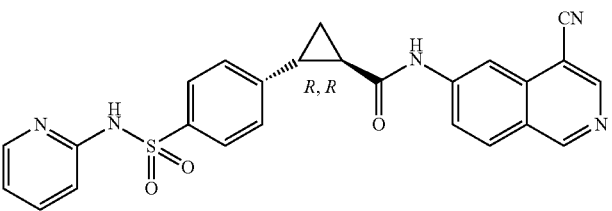<br>Batch 3 data | 0.9 nM JAK2<br>2.9 nM JAK3<br>20 nM ROCK2<br>30 nM ROCK1<br>6.9 nM IKK$_\beta$<br>2.0 nM JAK1<br>3.0 nM TYK2 |
| 94 | 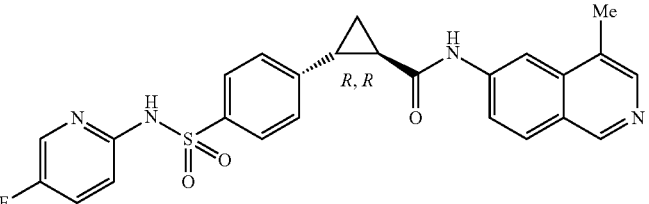<br>Pyridine series<br>chiral | 0.65 nM JAK2<br>3.9 nM JAK3<br>7.3 nM IKK$_\beta$<br>93 nM ROCK2<br>121 nM ROCK1<br>0.80 nM JAK1<br>10 nM TYK2 |
| 95 | 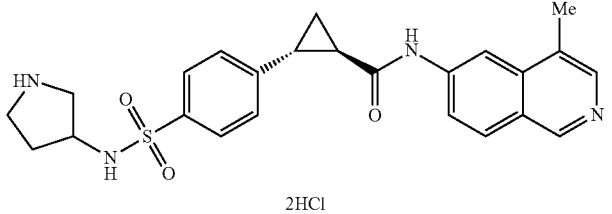 [SMILES: Cc1cncc2ccc(NC(=O)[C@@H]3C[C@H]3c3ccc(S(=O)(=O)NC4CCNC4)cc3)cc12 ; "2HCl"]<br>2HCl | 17 nM JAK2<br>175 nM JAK3<br>759 nM IKK$_\beta$<br>21 nM ROCK2<br>21 nM ROCK1<br>102 nM JAK1<br>200 nM TYK2 |
| 96 | 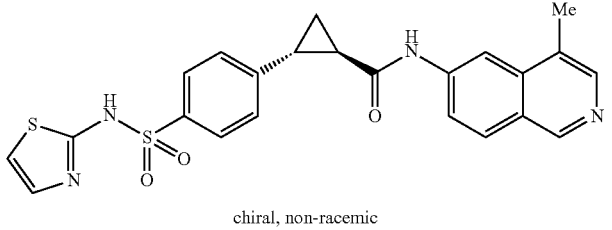 [SMILES: Cc1cncc2ccc(NC(=O)[C@@H]3C[C@H]3c3ccc(S(=O)(=O)Nc4nccs4)cc3)cc12]<br>chiral, non-racemic | 0.35 nM JAK2<br>2.4 nM JAK3<br>5.0 nM IKK$_\beta$<br>12.3 nM ROCK2<br>20.0 nM ROCK1<br>3.0 nM JAK1<br>4.9 nM TYK2 |

TABLE 2-continued

| Compound | Structure | IC$_{50}$ or Ki (nM) |
|---|---|---|
| 97 | Cynthia synthesis | |
| 98 | HCl<br>cyclopropyl chiral<br>amine racemic<br>3-piperidyl series | 21 nM JAK2<br>179 nM JAK3<br>825 nM IKK$_\beta$<br>15 nM ROCK2<br>18 nM ROCK1<br>121 nM JAK1<br>158 nM TYK2 |
| 99 | chiral, non-racemic<br>2-pyridyl series | 0.90 nM JAK2<br>9.0 nM JAK3<br>108 nM ROCK2<br>122 nM ROCK1<br>16 nM IKK$_\beta$<br>12.5 nM JAK1<br>11 nM TYK2 |
| 100 | chiral, non-racemic Pyrimidine series | 1.0 nM JAK2<br>3.4 nM JAK3<br>147 nM ROCK2<br>250 nM ROCK1<br>6.0 nM IKK$_\beta$<br>1.0 nM JAK1<br>5.0 nM TYK2 |
| 101 | chiral, non-racemic | 1.2 nM JAK2<br>18 nM JAK3<br>36 nM ROCK2<br>114 nM ROCK1<br>159 nM IKK$_\beta$<br>13 nM JAK1<br>146 nM TYK2 |
| 102 | Chiral, non-racemic | 3.0 nM JAK2<br>14.0 nM JAK3<br>74 nM ROCK2<br>220 nM ROCK1<br>105 nM IKK$_\beta$<br>15 nM JAK1<br>69 nM TYK2 |

TABLE 2-continued

| Compound | Structure | IC$_{50}$ or Ki (nM) |
| --- | --- | --- |
| 103 | 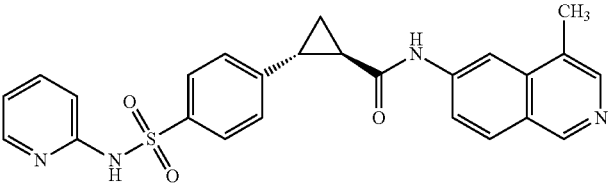<br>chiral non-racemic | 0.95 nM JAK2<br>1.9 nM JAK3<br>3.0 nM ROCK2<br>9.0 nM ROCK1<br>4.5 nM IKK$_\beta$<br>3.0 nM JAK1<br>5.0 nM TYK2 |
| 104 | 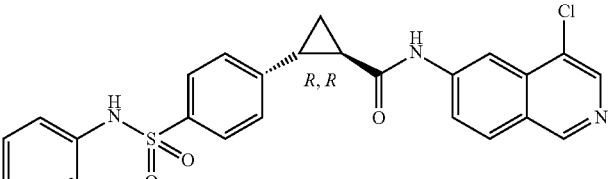<br>chiral, non-racemic<br>3-pyridyl series | 1.5 nM JAK2<br>17 nM JAK3<br>67 nM ROCK2<br>160 nM ROCK1<br>381 nM IKK$_\beta$<br>8 nM JAK1<br>82 nM TYK2 |
| 105 | 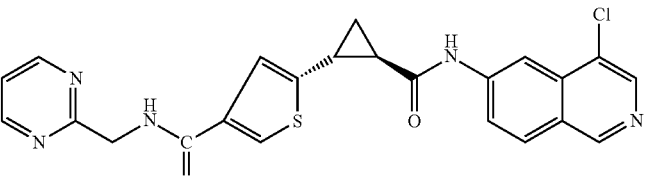<br>Jill synthesis, racemic | 2.0 nM JAK2<br>1.9 nM JAK3<br>6.0 nM ROCK2<br>8.0 nM ROCK1<br>100 nM IKK$_\beta$<br>12 nM JAK1<br>0.70 nM TYK2 |
| 106 | 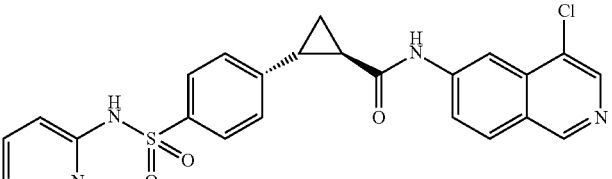<br>chiral, nonracemic | 0.70 nM JAK2<br>1.0 nM JAK3<br>3.0 nM ROCK2<br>4.7 nM ROCK1<br>3.2 nM IKK$_\beta$<br>12 nM PKC$_\delta$<br>0.70 nM JAK1<br>1.5 nM TYK2 |
| 107 | 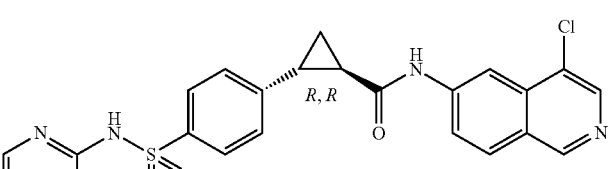<br>chiral, non-racemic | 0.70 nM JAK2<br>1.5 nM JAK3<br>0.95 nM JAK1<br>1.0 nM TYK2<br>68 nM ROCK2<br>128 nM ROCK1<br>4.1 nM IKK$_\beta$ |
| 108 | 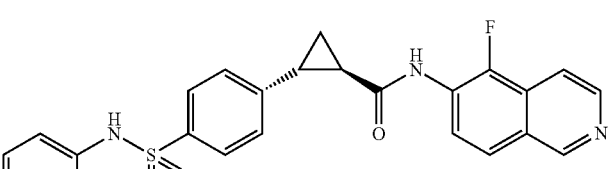<br>chiral non-racemic | 13.8 nM ROCK2<br>43 nM ROCK1<br>170 nM JAK2<br>350 nM JAK3<br>>5000 nM IKK$_\beta$ |

TABLE 2-continued

| Compound | Structure | IC$_{50}$ or Ki (nM) |
|---|---|---|
| 109 | 2HCl racemic | 12.4 nM ROCK2<br>28 nM ROCK1<br>JAK2 195 nM<br>JAK3 695 nM |
| 110 | R,R racemic | 1.5 nM JAK2<br>6.8 nM JAK3<br>7.9 nM ROCK2<br>13 nM ROCK1<br>15 nM IKK$_\beta$<br>456 nM PKA<br>27 nM JAK1<br>5.3 nM TYK2 |
| 111 | racemic | 2.0 nM JAK2<br>4.8 nM JAK3<br>56 nM ROCK2<br>156 nM ROCK1<br>88 nM IKK$_\beta$<br>0.8 nM JAK1<br>7.0 nM TYK2 |
| 112 | racemic | 1.5 nM JAK2<br>2.9 nM JAK3<br>194 nM ROCK2<br>470 nM ROCK1<br>12 nM IKK$_\beta$<br>0.8 nM JAK1<br>1.5 nM TYK2 |
| 113 | racemic | 2.0 nM JAK2<br>24 nM JAK3<br>77 nM ROCK2<br>150 nM ROCK1<br>16 nM IKK$_\beta$ |
| 114 | racemic | 2.0 nM JAK2<br>7.4 nM JAK3<br>265 nM ROCK2<br>533 nM ROCK1<br>10.0 nM IKK$_\beta$<br>11.0 nM JAK1<br>2.8 nM TYK2 |

TABLE 2-continued

| Compound | Structure | IC$_{50}$ or Ki (nM) |
|---|---|---|
| 115 | 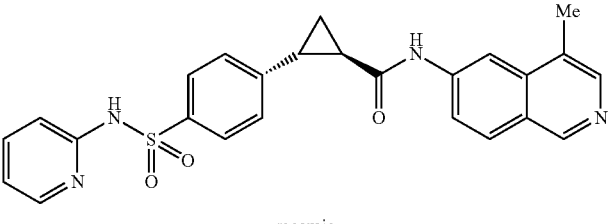 racemic | 2.0 nM JAK2<br>6.3 nM JAK3<br>12 nM ROCK2<br>27 nM ROCK1<br>8.2 nM IKK$_\beta$<br>25 nM JAK1<br>7.0 nM TYK2 |
| 116 | 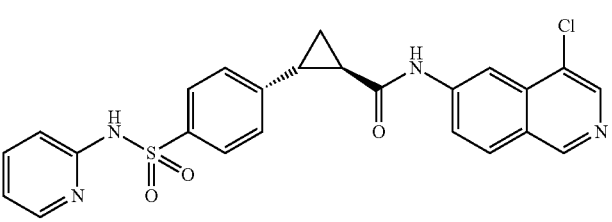 racemic | 0.5-1.5 nM JAK2<br>1.9 nM JAK3<br>1.5 nM JAK1<br>2.9 nM TYK2<br>8.0 nM ROCK2<br>13 nM ROCK1<br>9 nM IKK$_\beta$ |
| 117 | 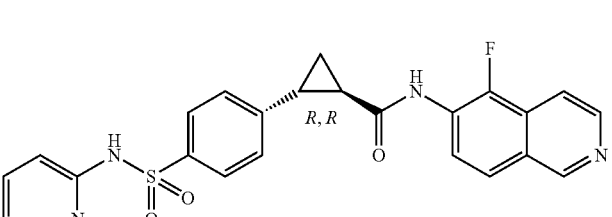 racemic | 4.9 nM ROCK2<br>10 nM ROCK1<br>21 nM JAK2<br>127 nM JAK3<br>144 nM IKK$_\beta$ |
| 118 | 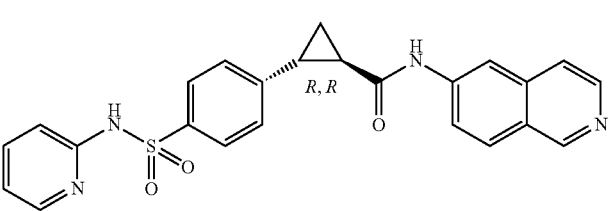 chiral non-racemic | 0.6 nM JAK2<br>4.7 nM JAK3<br>3.6 nM IKK$_\beta$<br>2.0 nM ROCK2<br>3.4 nM ROCK1<br>25 nM JAK1<br>12 nM TYK2 |
| 119 | 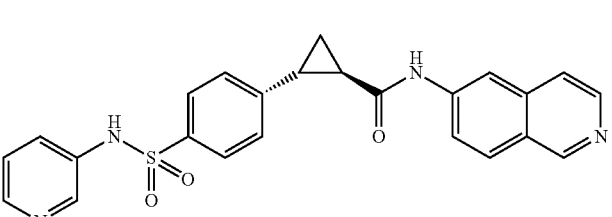 racemic | 23 nM ROCK2<br>72 nM ROCK1<br>12 nM JAK2<br>118 nM JAK3<br>650 nM IKK$_\beta$<br>55 nM JAK1<br>1129 nM TYK2 |
| 120 | 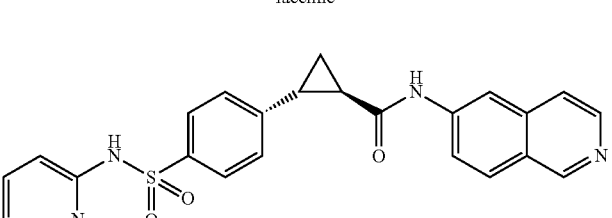 racemic | 6 nM ROCK2<br>9 nM ROCK1<br>2.0 nM JAK2<br>10 nM JAK3<br>8 nM IKK$_\beta$ |

TABLE 2-continued

| Compound | Structure | IC$_{50}$ or Ki (nM) |
|---|---|---|
| 121 | racemic | 10 nM ROCK2<br>10 nM ROCK1<br>14.8 nM JAK2<br>153 nM JAK3<br>325 nM TYK2 |
| 122 | 2HCl<br>racemic | 7.0 nM ROCK2<br>8.2 nM ROCK1<br>59 nM JAK2<br>930 nM JAK3<br>JAK1 >500 nM |
| 123 | 2HCl<br>racemic | 4.0 nM ROCK2<br>4.0 nM ROCK1<br>JAK2- 44 nM<br>JAK3- 1140 nM |
| 124 | 2HCl<br>racemic | 31 nM ROCK2<br>48 nM ROCK1<br>JAK2 652 nM |
| 125 | 2HCl<br>racemic | 3 nM ROCK2<br>3.5 nM ROCK1<br>JAK2 65 nM |
| 126 | 2HCl<br>racemic | 5 nM ROCK2<br>5 nM ROCK1<br>JAK2 72 nM<br>900 nM JAK3 |

TABLE 2-continued

| Compound | Structure | IC$_{50}$ or Ki (nM) |
|---|---|---|
| 127 | 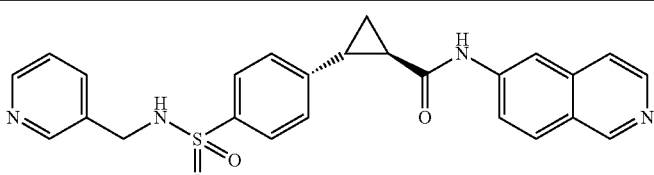 racemic Alkylheteroaryl series | 9 nM ROCK2<br>25 nM ROCK1<br>900 nM JAK2<br>2000 nM JAK3<br>4100 nM IKK$_\beta$ |
| 128 | 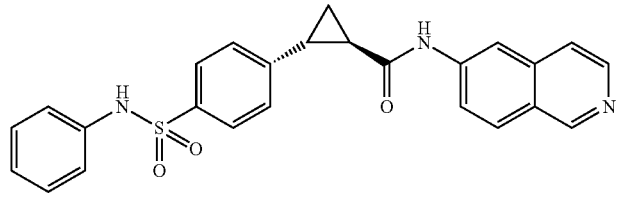 Aryl series racemic | 75 nM ROCK2<br>154 nM ROCK1<br>17 nM JAK2<br>36 nM JAK3 |
| 129 | 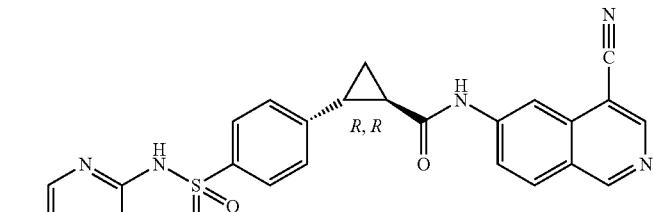 chiral non-racemic | 1.0 nM JAK2<br>4.8 nM JAK3<br>38 nM IKK$_\beta$<br>343 nM ROCK2<br>748 nM ROCK1<br>0.9 nM JAK1<br>9.0 nM TYK2 |
| 130 | 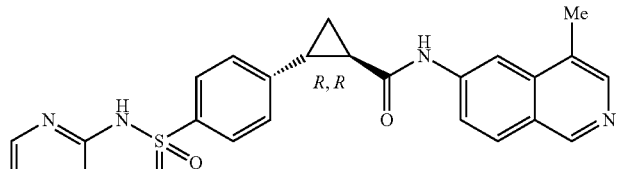 Pyrimidine series | 1.0 nM JAK2<br>2.9 nM JAK3<br>120 nM ROCK2<br>250 nM ROCK1<br>5.0 nM IKK$_\beta$<br>1.0 nM JAK1<br>0.44 nM TYK2 |
| 131 | 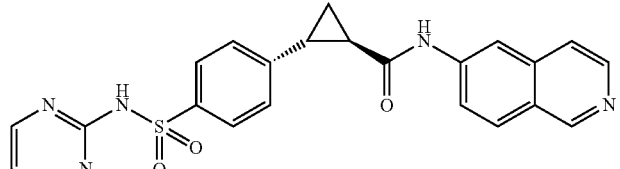 racemic | 2.0 nM JAK2<br>25.0 nM JAK3<br>77 nM ROCK2<br>150 nM ROCK1<br>17 nM IKK$_\beta$ |
| 132 | 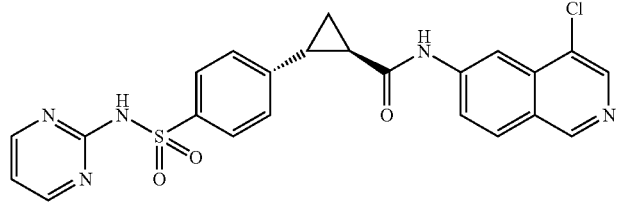 racemic | 1.5 nM JAK2<br>2.9 nM JAK3<br>194 nM ROCK2<br>470 nM ROCK1<br>12 nM IKK$_\beta$ |

TABLE 2-continued

| Compound | Structure | IC$_{50}$ or Ki (nM) |
|---|---|---|
| 133 | 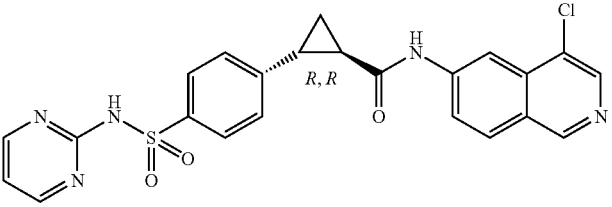 chiral, non-racemic | 0.70 nM JAK2<br>1.5 nM JAK3<br>68 nM ROCK2<br>128 nM ROCK1<br>4.1 nM IKK$_\beta$<br>2.0 nM JAK1<br>0.25 nM TYK2 |
| 134 | 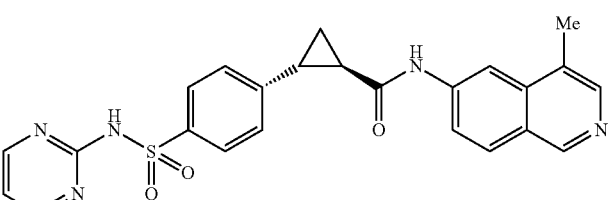 racemic | 2.0 nM JAK2<br>7.4 nM JAK3<br>265 nM ROCK2<br>606 nM ROCK1<br>10.0 nM IKK$_\beta$<br>11.0 nM JAK1<br>2.8 nM TYK2 |
| 135 | 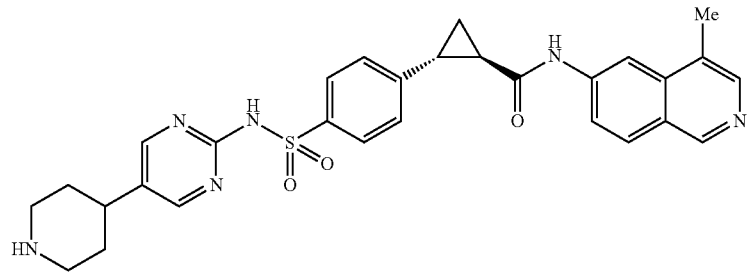 chiral, non-racemic | 19 nM JAK2<br>148 nM JAK3<br>4.9 nM ROCK2<br>16 nM ROCK1<br>1130 nM IKK$_\beta$ |
| 136 | 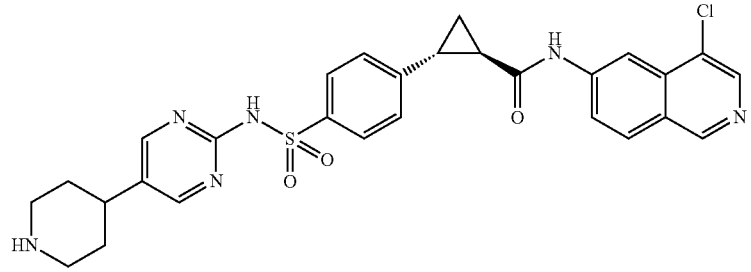 chiral, non-racemic (batch one) | 0.9 nM JAK2<br>15 nM JAK3<br>23 nM ROCK2<br>35 nM ROCK1<br>509 nM IKK$_\beta$<br>8.5 nM JAK1<br>40 nM TYK2 |
| 137 | 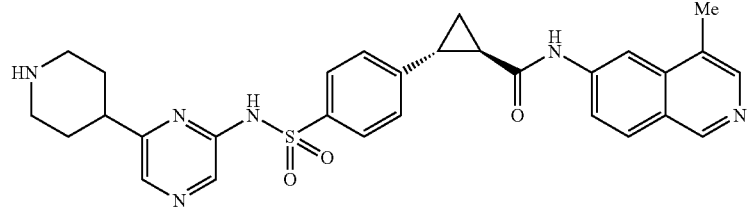 chiral, non-racemic | 7.0 nM JAK2<br>98 nM JAK3<br>31 nM ROCK2<br>68 nM ROCK1<br>208 nM IKK$_\beta$ |

TABLE 2-continued

| Compound | Structure | IC$_{50}$ or Ki (nM) |
|---|---|---|
| 138 | chiral, non-racemic | |
| 139 | chiral, non-racemic | |
| 140 | chiral, non-racemic | 0.70 nM JAK2<br>1.5 nM JAK3<br>68 nM ROCK2<br>128 nM ROCK1<br>4.1 nM IKK$_\beta$<br>2.0 nM JAK1<br>0.25 nM TYK2 |
| 141 | chiral, non-racemic | 1.0 nM JAK2<br>5.8 nM JAK3<br>875 nM ROCK2<br>1200 nM ROCK1<br>3.6 nM IKK$_\beta$<br>7.3 nM JAK1<br>12 nM TYK2 |
| 142 | chiral, non-racemic | |
| 143 | Chiral, non-racemic | 3.0 nM JAK2<br>14.0 nM JAK3<br>74 nM ROCK2<br>220 nM ROCK1<br>105 nM IKK$_\beta$<br>15 nM JAK1<br>34 nM TYK2 |

TABLE 2-continued

| Compound | Structure | IC$_{50}$ or Ki (nM) |
|---|---|---|
| 144 | Chiral, non-racemic | 10.8 nM JAK2<br>135 nM JAK3<br>57 nM ROCK2<br>153 nM ROCK1<br>765 nM IKK$_\beta$ |
| 145 | R, R | |
| 146 | 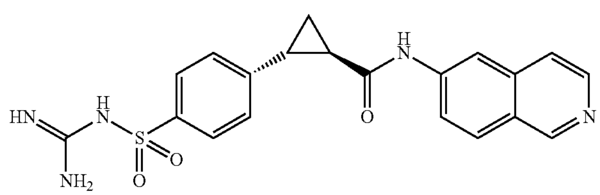 | 2.0 nM ROCK2<br>3.4 nM ROCK1<br>4.5 nM JAK2<br>23 nM JAK3<br>34.5 nM IKK$_\beta$ |
| 147 | 2HCl | 17 nM JAK2<br>175 nM JAK3<br>759 nM IKK$_\beta$<br>21 nM ROCK2<br>21 nM ROCK1 |
| 148 | 2HCl | |
| 149 | 2HCl | |

TABLE 2-continued

| Compound | Structure | IC$_{50}$ or Ki (nM) |
| --- | --- | --- |
| 150 | (2HCl) | |
| 151 | (racemic) | 2.0 nM JAK2<br>7.4 nM JAK3<br>265 nM ROCK2<br>606 nM ROCK1<br>10.0 nM IKK$_\beta$<br>11.0 nM JAK1<br>2.8 nM TYK2 |
| 152 | (HCl) | |
| 153 | (2HCl) | |
| 154 | (HCl) | |
| 155 | (2HCl) | |

TABLE 2-continued

| Compound | Structure | IC$_{50}$ or Ki (nM) |
|---|---|---|
| 156 | (structure with 4-fluoroisoquinoline, cyclopropane, phenyl, sulfonamide with aminoethyl; 2HCl) | |
| 157 | (structure with 4-CF$_3$ isoquinoline, R,R cyclopropane, phenyl, sulfonamide-pyridin-2-yl; chiral non-racemic) | 0.90 nM JAK2<br>9.0 nM JAK3<br>108 nM ROCK2<br>122 nM ROCK1<br>16 nM IKK$_\beta$ |
| 158 | (structure with 4-Me isoquinoline, cyclopropane, phenyl, sulfonamide-pyridin-2-yl; racemic) | 2.0 nM JAK2<br>6.3 nM JAK3<br>13.8 nM ROCK2<br>27 nM ROCK1<br>8.2 nM IKK$_\beta$<br>25 nM JAK1<br>7.0 nM TYK2 |
| 159 | (structure with isoquinoline, cyclopropane, fluoro-phenyl, sulfonamide-pyridin-2-yl) | |
| 160 | (structure with 4-OCF$_3$ isoquinoline, R,R cyclopropane, phenyl, sulfonamide-pyridin-2-yl) | |
| 161 | (structure with 4-nPr isoquinoline, R,R cyclopropane, phenyl, sulfonamide-pyridin-2-yl) | |
| 162 | (structure with 4-CH$_2$CF$_3$ isoquinoline, R,R cyclopropane, phenyl, sulfonamide-pyridin-2-yl) | |

TABLE 2-continued

| Compound | Structure | IC$_{50}$ or Ki (nM) |
|---|---|---|
| 163 | (piperidin-4-yl-pyridin-2-yl)sulfamoyl-phenyl-(R,R)-cyclopropyl-C(O)NH-(4-methylisoquinolin-6-yl) | |
| 164 | (5-((dimethylamino)methyl)pyridin-2-yl)sulfamoyl-phenyl-(R,R)-cyclopropyl-C(O)NH-(4-methylisoquinolin-6-yl) | |
| 165 | (5-((dimethylamino)methyl)pyridin-2-yl)sulfamoyl-phenyl-(R,R)-cyclopropyl-C(O)NH-(4-chloroisoquinolin-6-yl) | |
| 166 | (5-((dimethylamino)methyl)pyridin-2-yl)sulfamoyl-phenyl-(R,R)-cyclopropyl-C(O)NH-(4-chloroisoquinolin-6-yl) | |
| 167 | (pyridin-2-yl)sulfamoyl-phenyl-(R,R)-cyclopropyl-C(O)NH-(4-fluoro-1-hydroxyisoquinolin-6-yl) | |
| 168 | (5-chloropyridin-2-yl)sulfamoyl-phenyl-(R,R)-cyclopropyl-C(O)NH-(4-chloroisoquinolin-6-yl) | |
| 169 | (pyridin-3-yl)sulfamoyl-phenyl-(R,R)-cyclopropyl-C(O)NH-(4-methylisoquinolin-6-yl) chiral, non-racemic | 1.15 nM JAK2<br>19 nM JAK3<br>44 nM ROCK2<br>125 nM ROCK1<br>159 nM IKK$_\beta$<br>120 nM JAK1<br>98 nM TYK2 |

TABLE 2-continued

| Compound | Structure | IC$_{50}$ or Ki (nM) |
| --- | --- | --- |
| 170 | Heteroaryl | 0.35 nM JAK2<br>3.4 nM JAK3<br>5.0 nM IKK$_\beta$<br>12.3 nM ROCK2<br>20.0 nM ROCK1<br>3.0 nM JAK1<br>4.9 nM TYK2 |
| 171 | 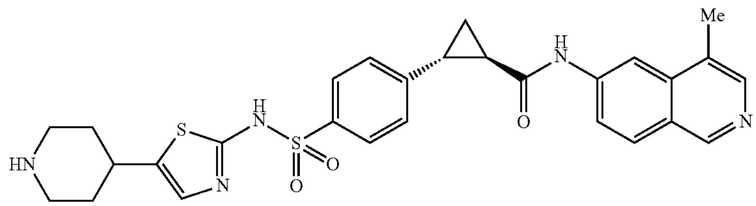 [SMILES: Cc1cncc2ccc(NC(=O)[C@@H]3C[C@H]3c3ccc(S(=O)(=O)Nc4ncc(C5CCNCC5)s4)cc3)cc12] | |
| 172 | 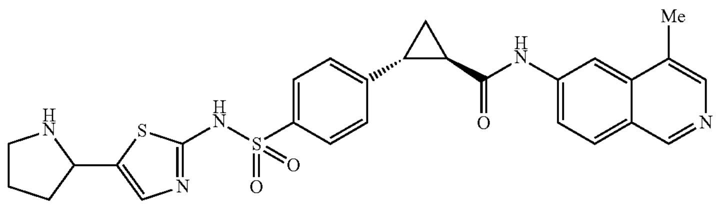 [SMILES: Cc1cncc2ccc(NC(=O)[C@@H]3C[C@H]3c3ccc(S(=O)(=O)Nc4ncc(C5CCCN5)s4)cc3)cc12] | |
| 173 | 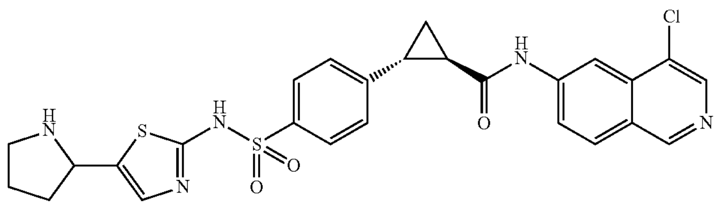 [SMILES: O=C(Nc1ccc2cncc(Cl)c2c1)[C@@H]1C[C@H]1c1ccc(S(=O)(=O)Nc2ncc(C3CCCN3)s2)cc1] | |
| 174 | chiral, non-racemic | 3.4 nM JAK2<br>17 nM JAK3<br>235 nM IKK$_\beta$<br>17.3 nM ROCK2<br>246 nM ROCK1<br>16 nM JAK1<br>29 nM TYK2 |
| 175 | 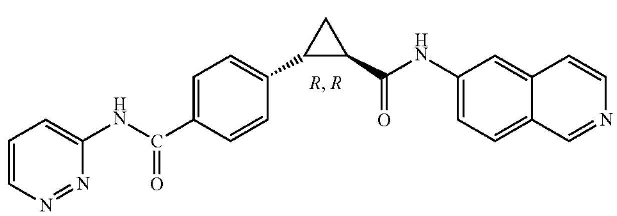 | 70 nM JAK2<br>200 nM JAK3<br>150 nM IKK$_\beta$<br>2.5 nM ROCK2<br>4.3 nM ROCK1<br>PTM: 650 nM |
| 176 | chiral, non-racemic | 9.4 nM JAK2<br>38 nM JAK3<br>280 nM IKK$_\beta$<br>3.5 nM ROCK2<br>6.4 nM ROCK1 |

TABLE 2-continued

| Compound | Structure | IC$_{50}$ or Ki (nM) |
|---|---|---|
| 177 | 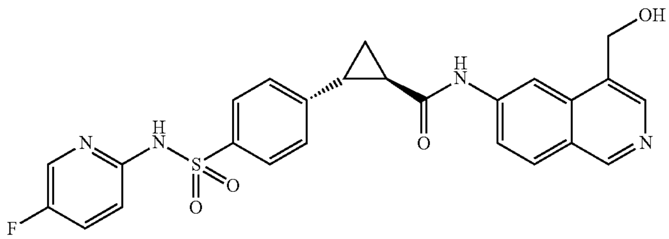 | |
| 178 | 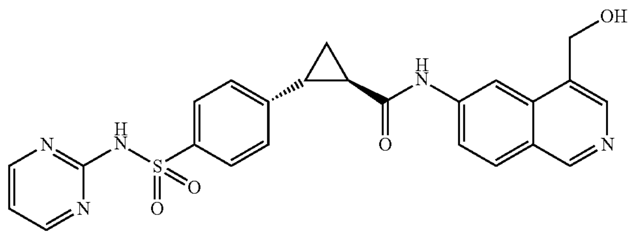 | |
| 179 | 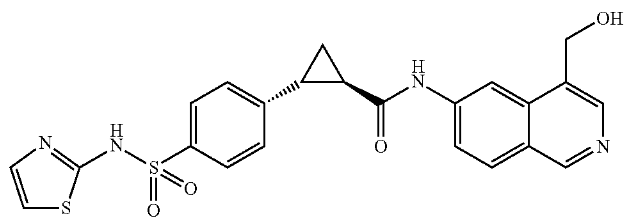 | |
| 180 | 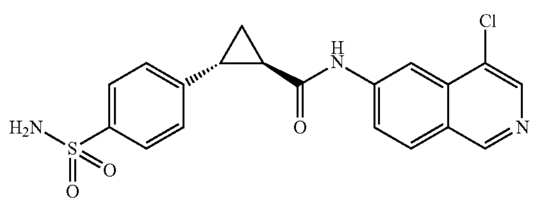 [SMILES: NS(=O)(=O)c1ccc([C@@H]2C[C@H]2C(=O)Nc2ccc3cncc(Cl)c3c2)cc1] | |

While the disclosure has been described in detail and with reference to specific embodiments thereof, it will be apparent to one skilled in the art that various changes and modifications can be made without departing from the spirit and scope of the disclosure.

What is claimed is:

1. A compound of Formula (I):

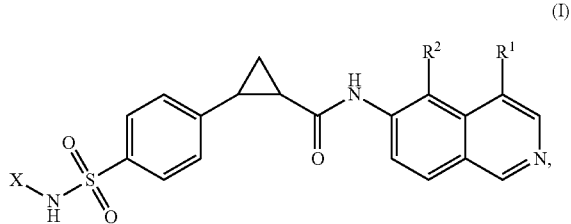

(I)

or a pharmaceutically acceptable salt thereof,
wherein
$R^1$ is H, halo, —CN, —$C_{1-6}$ alkyl, —$C_{1-6}$ alkoxyl, —$C_{1-6}$ haloalkyl; —$C_{1-6}$ haloalkoxyl;
$R^2$ is H or halo;
X is —($C_{1-5}$ heteroaryl)-$R^3$; and
$R^3$ is —$C_{2-6}$ heterocyclyl, or —$C_{1-6}$ heteroalkyl.

2. The compound of claim 1, wherein the compound of Formula (I) is a compound of Formula (II):

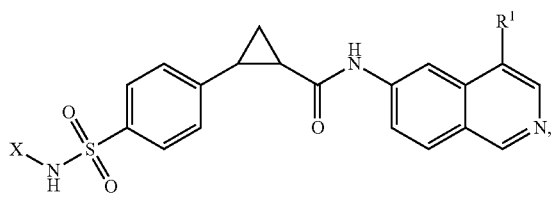

(II)

or a pharmaceutically acceptable salt thereof.

3. The compound of claim 1, wherein the compound of Formula (I) is a compound of Formula (III):

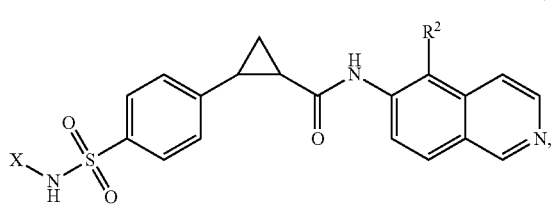

(III)

or a pharmaceutically acceptable salt thereof.

4. The compound of claim 1, wherein $R^1$ is H, halo, —CN, —$C_{1-3}$ alkyl, —$C_{1-3}$ alkoxyl, —$C_{1-3}$ haloalkyl, —$C_{1-3}$ haloalkoxyl.

5. The compound of claim 1, wherein $R^1$ is H, Cl, —CN, —$CH_3$, —$CH_2CH_3$, —$CH(CH_3)_2$, —$CHF_2$, —$CF_3$, or —$OCF_3$.

6. The compound of claim 1, wherein $R^1$ is Cl, —CN, —$CH_3$, —$CH_2CH_3$, —$CH(CH_3)_2$, —$CHF_2$, —$CF_3$, or —$OCF_3$.

7. The compound of claim 1, wherein $R^2$ is F, Cl, Br, or I.

8. The compound of claim 1, wherein $R^2$ is H or F.

9. The compound of claim 1, wherein X is —($C_{3-5}$ heteroaryl)-$R^3$.

10. The compound of claim 1, wherein X is

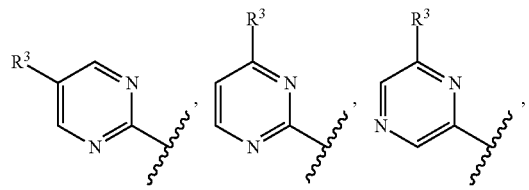

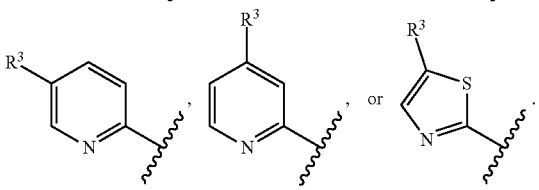

11. The compound of claim 1, wherein $R^3$ is —$C_{2-6}$ heterocyclyl.

12. The compound of claim 1, wherein $R^3$ is —$C_{3-5}$ heterocycloalkyl.

13. The compound of claim 1, wherein $R^3$ is

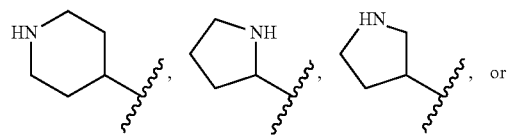

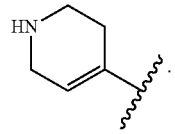

14. The compound of claim 1, wherein
$R^1$ is H, Cl, —CN, —$CH_3$, —$CH_2CH_3$, —$CH(CH_3)_2$, —$CF_3$, or —$OCF_3$;
$R^2$ is H or F;

X is
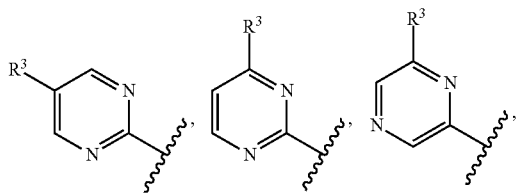
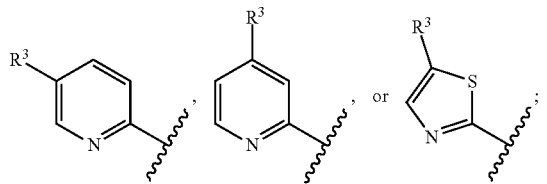
and R³ is
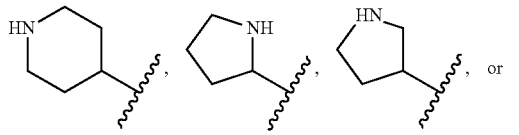
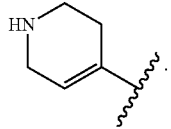
15. The compound of claim 1, wherein
R¹ is Cl, —CN, —CH₃, —CH₂CH₃, —CH(CH₃)₂, —CF₃, or —OCF₃;
R² is H or F;
X is
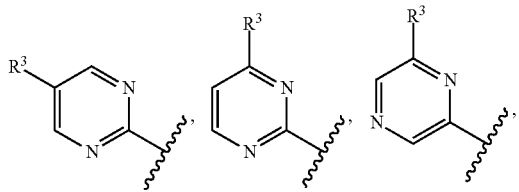
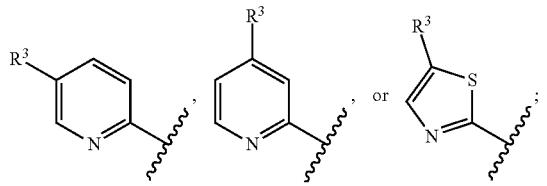
and
R³ is
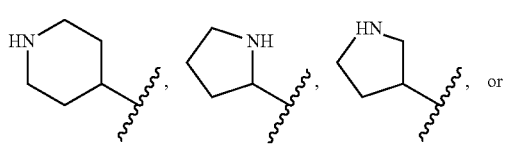
-continued
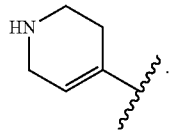
16. The compound of claim 1, selected from:
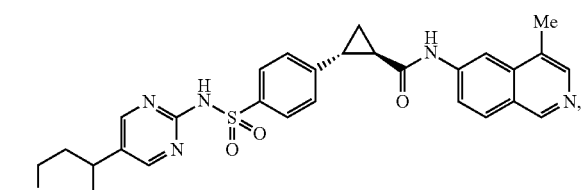
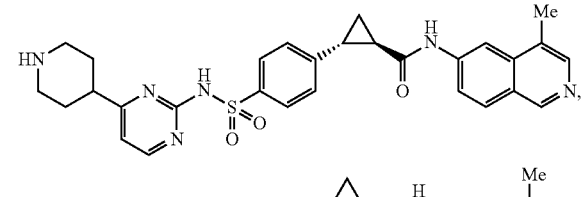
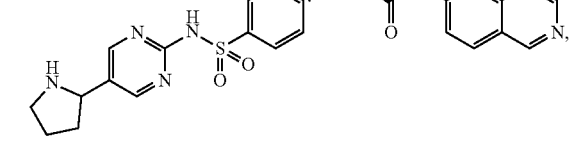
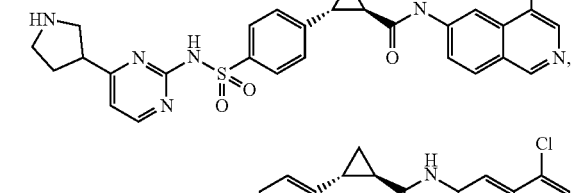
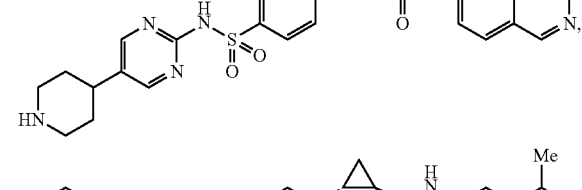
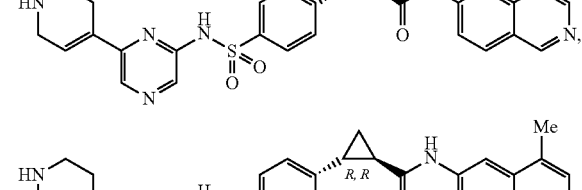
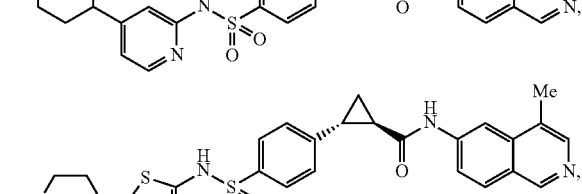
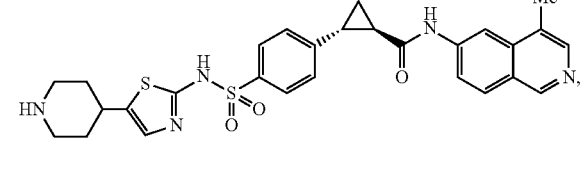

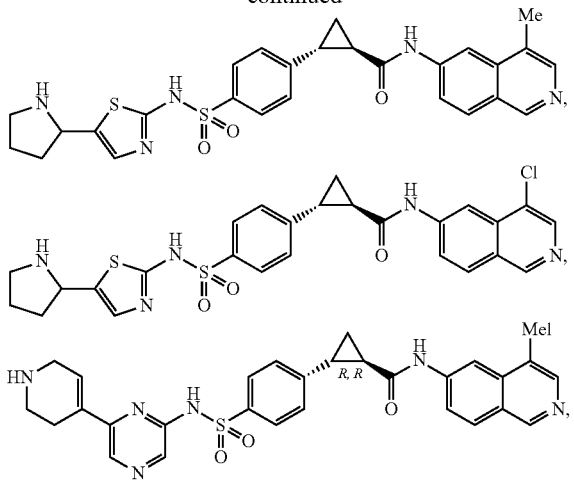

or a pharmaceutically acceptable salt thereof.

17. A pharmaceutical composition, comprising the compound of claim 1 and a pharmaceutically acceptable carrier.

18. A pharmaceutical composition, comprising the compound of claim 2 and a pharmaceutically acceptable carrier.

19. A pharmaceutical composition, comprising the compound of claim 3 and a pharmaceutically acceptable carrier.

20. A pharmaceutical composition, comprising the compound of claim 4 and a pharmaceutically acceptable carrier.

21. A pharmaceutical composition, comprising the compound of claim 5 and a pharmaceutically acceptable carrier.

22. A pharmaceutical composition, comprising the compound of claim 6 and a pharmaceutically acceptable carrier.

23. A pharmaceutical composition, comprising the compound of claim 7 and a pharmaceutically acceptable carrier.

24. A pharmaceutical composition, comprising the compound of claim 8 and a pharmaceutically acceptable carrier.

25. A pharmaceutical composition, comprising the compound of claim 9 and a pharmaceutically acceptable carrier.

26. A pharmaceutical composition, comprising the compound of claim 10 and a pharmaceutically acceptable carrier.

27. A pharmaceutical composition, comprising the compound of claim 11 and a pharmaceutically acceptable carrier.

28. A pharmaceutical composition, comprising the compound of claim 12 and a pharmaceutically acceptable carrier.

29. A pharmaceutical composition, comprising the compound of claim 13 and a pharmaceutically acceptable carrier.

30. A pharmaceutical composition, comprising the compound of claim 14 and a pharmaceutically acceptable carrier.

31. A pharmaceutical composition, comprising the compound of claim 15 and a pharmaceutically acceptable carrier.

32. A pharmaceutical composition, comprising the compound of claim 16 and a pharmaceutically acceptable carrier.

* * * * *